United States Patent
Sun et al.

(10) Patent No.: US 9,856,219 B2
(45) Date of Patent: *Jan. 2, 2018

(54) SUBSTITUTED QUINOLINE COMPOUNDS AS S-NITROSOGLUTATHIONE REDUCTASE INHIBITORS

(71) Applicant: Nivalis Therapeutics, Inc., Boulder, CO (US)

(72) Inventors: Xicheng Sun, Broomfield, CO (US); Jian Qiu, Longmont, CO (US); Adam Stout, Ann Arbor, MI (US)

(73) Assignee: Nivalis Therapeutics, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/228,088

(22) Filed: Aug. 4, 2016

(65) Prior Publication Data

US 2016/0340312 A1   Nov. 24, 2016

Related U.S. Application Data

(63) Continuation of application No. 15/097,378, filed on Apr. 13, 2016, now Pat. No. 9,433,618, which is a continuation of application No. 14/817,329, filed on Aug. 4, 2015, now Pat. No. 9,315,462, which is a continuation of application No. 14/540,216, filed on Nov. 13, 2014, now Pat. No. 9,139,528, which is a continuation of application No. 13/824,430, filed as application No. PCT/US2011/055200 on Oct. 7, 2011, now Pat. No. 8,921,562.

(60) Provisional application No. 61/391,225, filed on Oct. 8, 2010, provisional application No. 61/423,805, filed on Dec. 16, 2010.

(51) Int. Cl.
| | |
|---|---|
| C07D 215/20 | (2006.01) |
| C07D 215/46 | (2006.01) |
| C07D 215/00 | (2006.01) |
| C07D 215/42 | (2006.01) |
| C07D 215/54 | (2006.01) |
| C07D 215/60 | (2006.01) |
| C07D 401/04 | (2006.01) |
| C07D 401/10 | (2006.01) |
| C07D 409/04 | (2006.01) |
| C07D 409/14 | (2006.01) |
| C07D 413/10 | (2006.01) |
| C07D 417/10 | (2006.01) |
| A61K 31/47 | (2006.01) |
| A61K 31/4706 | (2006.01) |
| A61K 31/4709 | (2006.01) |

(52) U.S. Cl.
CPC ........... *C07D 215/20* (2013.01); *A61K 31/47* (2013.01); *A61K 31/4706* (2013.01); *A61K 31/4709* (2013.01); *C07D 215/00* (2013.01); *C07D 215/42* (2013.01); *C07D 215/46* (2013.01); *C07D 215/54* (2013.01); *C07D 215/60* (2013.01); *C07D 401/04* (2013.01); *C07D 401/10* (2013.01); *C07D 409/04* (2013.01); *C07D 409/14* (2013.01); *C07D 413/10* (2013.01); *C07D 417/10* (2013.01)

(58) Field of Classification Search
None
See application file for complete search history.

(56) References Cited

U.S. PATENT DOCUMENTS

| | | | |
|---|---|---|---|
| 5,480,883 A | 1/1996 | Spada et al. | |
| 5,646,153 A | 7/1997 | Spada et al. | |
| 5,795,889 A | 8/1998 | Spada et al. | |
| 5,882,546 A | 3/1999 | Manero et al. | |
| 5,911,913 A | 6/1999 | Manero et al. | |
| 6,180,632 B1 | 1/2001 | Myers et al. | |
| 7,674,809 B2 | 3/2010 | Makovec et al. | |
| 8,546,392 B2 | 10/2013 | Hartmann et al. | |
| 8,785,643 B2 | 7/2014 | Sun et al. | |
| 8,921,562 B2 | 12/2014 | Sun et al. | |
| 9,012,646 B2 | 4/2015 | Sun et al. | |
| 9,139,528 B2 | 9/2015 | Sun et al. | |
| 9,221,810 B2 | 12/2015 | Sun et al. | |
| 9,315,462 B2 | 4/2016 | Sun et al. | |
| 9,364,481 B2 | 6/2016 | Sun et al. | |
| 9,433,618 B2 | 9/2016 | Sun et al. | |
| 2002/0128205 A1 | 9/2002 | Stamler et al. | |
| 2002/0151544 A1 | 10/2002 | Hayakawa et al. | |
| 2003/0088105 A1 | 5/2003 | Krich et al. | |
| 2005/0009865 A1 | 1/2005 | Kudo et al. | |
| 2005/0014697 A1 | 1/2005 | Stamler et al. | |
| 2005/0187166 A1 | 8/2005 | Stamler et al. | |
| 2005/0260126 A1 | 11/2005 | Kudo et al. | |

(Continued)

FOREIGN PATENT DOCUMENTS

| | | |
|---|---|---|
| CN | 101068551 A | 11/2007 |
| EP | 0058822 | 9/1982 |
| EP | 1277738 A1 | 1/2003 |
| EP | 1683523 A1 | 7/2006 |
| JP | 2007-504281 A | 3/2007 |

(Continued)

OTHER PUBLICATIONS

Bateman et al. (Sep. 29, 2008) "Human carbonyl reductase is an S-nitrosoglutathione reductase" J Biol Chem, 283 p. 35756-35762.
Bowman et al. (2007) J. Am. Chem 129:3634-3640 "Protein Flexibility and Species Specificity in Structure-Based Drug Discovery: Dihydrofolate Reductase as a Test System" with Supplement pp. S2-S34.
Branchini, B et al, (1989) "Naphthyl- and Quinolylluciferin: Green and Red Light Emitting Firefly Luciferin Analogues" Photochemistry and Photobiology, 49(5), 689-95.

(Continued)

*Primary Examiner* — Heidi Reese
(74) *Attorney, Agent, or Firm* — Swanson & Bratschun, L.L.C.

(57) ABSTRACT

The present invention is directed to novel quinoline compounds useful as S-nitrosoglutathione reductase (GSNOR) inhibitors, pharmaceutical compositions comprising such compounds, and methods of making and using the same.

14 Claims, No Drawings

(56) References Cited

U.S. PATENT DOCUMENTS

| | | |
|---|---|---|
| 2006/0018825 A1 | 1/2006 | Kudo et al. |
| 2007/0054903 A1 | 3/2007 | Kim et al. |
| 2007/0293492 A1 | 12/2007 | DeVita et al. |
| 2008/0103308 A1 | 5/2008 | Ragini et al. |
| 2009/0029987 A1 | 1/2009 | Wong et al. |
| 2010/0035887 A1 | 2/2010 | Ricciardi |
| 2010/0113508 A1 | 5/2010 | Binch et al. |
| 2010/0144733 A1 | 6/2010 | Doyle et al. |
| 2010/0204234 A1 | 8/2010 | Hartmann et al. |
| 2010/0286174 A1 | 11/2010 | Stamler et al. |
| 2013/0178499 A1 | 7/2013 | Sun et al. |
| 2013/0261122 A1 | 10/2013 | Sun et al. |
| 2013/0261123 A1 | 10/2013 | Sun et al. |
| 2014/0094465 A1 | 4/2014 | Sun et al. |
| 2014/0329821 A1 | 11/2014 | Sun et al. |
| 2015/0080429 A1 | 3/2015 | Sun et al. |
| 2015/0183774 A1 | 7/2015 | Sun et al. |
| 2015/0336897 A1 | 11/2015 | Sun et al. |
| 2016/0067254 A1 | 3/2016 | Sun et al. |
| 2016/0220556 A1 | 8/2016 | Sun et al. |
| 2016/0279117 A1 | 9/2016 | Sun et al. |

FOREIGN PATENT DOCUMENTS

| | | |
|---|---|---|
| JP | 2008-521905 A | 6/2008 |
| JP | 2013-519680 A | 5/2013 |
| WO | WO 97-48694 | 12/1997 |
| WO | WO 98-54158 | 12/1998 |
| WO | WO 99-38845 | 8/1999 |
| WO | WO 01/83456 | 11/2001 |
| WO | WO 02-28841 | 4/2002 |
| WO | WO 02-060876 | 8/2002 |
| WO | WO 03-016292 | 2/2003 |
| WO | WO 2004-080170 | 9/2004 |
| WO | WO 2004/103973 A1 | 12/2004 |
| WO | WO 2005-063712 | 7/2005 |
| WO | WO 2005-118580 | 12/2005 |
| WO | WO 2006-004722 | 1/2006 |
| WO | WO 2006-034491 A2 | 3/2006 |
| WO | WO 2006-060390 A1 | 6/2006 |
| WO | WO 2006-127329 | 11/2006 |
| WO | WO 2006-130551 | 12/2006 |
| WO | WO 2007-016525 A2 | 2/2007 |
| WO | WO 2008-032105 | 3/2008 |
| WO | WO 2008-069976 | 6/2008 |
| WO | WO 2008-144865 | 12/2008 |
| WO | WO 2008-157500 | 12/2008 |
| WO | WO 2009-007457 | 1/2009 |
| WO | WO 2009-076665 | 6/2009 |
| WO | WO 2010-018458 | 2/2010 |
| WO | WO 2010-019903 A1 | 2/2010 |
| WO | WO 2010-019905 A1 | 2/2010 |
| WO | WO 2010-019909 A1 | 2/2010 |
| WO | WO 2010-107476 | 9/2010 |
| WO | WO 2011-100433 A1 | 8/2011 |
| WO | WO 2012-048181 | 4/2012 |
| WO | WO 2012-083165 | 6/2012 |
| WO | WO 2012-083171 | 6/2012 |
| WO | WO 2012-170371 | 12/2012 |

OTHER PUBLICATIONS

Bridges et al. (1968) "The Fluorescence of Indoles and Analine Derivatives" Biochem. J. 107:225-237.

De Belder et al. (May 1994) "Effects of S-nitroso-glutathione in the human forearm circulation; evidence for selective inhibition of platelet activation", Cardiovasc Res., 28(5):691-694.

De Jesus-Berrios et al. (Nov. 2003) "Enzymes that Counteract Nitrosative Stress Promot Fungal Virulence", Curr. Biol., 13:1963-1968.

EP Search Report dated Jun. 19, 2015 in EP application serial No. EP 11849278.4.

EP Search Report dated Jun. 26, 2014 in EP application serial No. 11831651.2.

EP Search Report dated Nov. 15, 2015 in EP application serial No. EP 15180449.9.

Foster et al. (Apr. 2003) "S-nitrosylation in health and disease", Trends in Molecular Medicine, 9(4):160-168.

Frotscher et al. (2008) "Design, Synthesis, and Biological Evaluation of (Hydroxyphenyl)naphthalene and -quinoline Derivatives: Potent and Selective Nonsteroidal Inhibitors of 17β-Hydroxysteroid Dehydrogenase Type 1 (17β-HSD1) for the Treatment of Estrogen-Dependent Diseases ", J. Med. Che. 51(7):2158-2169.

Gaston et al. (Dec. 1993) "Endogenous nitrogen oxides and bronchodilator S-nitrosolthiols in human airways", Proc. Natl. Acad. Sci. USA, 90:10957-10961.

Georgii et al. (2011) "Topical S-nitrosoglutathione-Releasing Hydrogel Improves Healing of Rat Ischaemic Wounds", J Tissue Eng Regen Med, 5:612-619.

Haq et al. (2007) "S-nitrosoglutathione Prevents Interphotoreceptor Retinoid-Binding Protein (IRBP[161-180])-Induced Experimental Autoimmune Uveitis" J Ocular Pharm and Therapeutics, 23(3):221-231.

International Preliminary Report on Patentability mailed in PCT/US2011/055200 dated Apr. 18, 2013.

International Preliminary Report on Patentability mailed in PCT/US2011/065490 dated Jun. 27, 2013.

International Search Report and Written Opinion mailed in PCT/US2011/055200 dated Mar. 16, 2012.

International Search Report and Written Opinion mailed in PCT/US2011/065490 dated May 2, 2012.

Jensen et al. (1998) "S-Nitrosoglutathione is a substrate for rat alcohol dehydrognease class III isoenzyme", Biochem J., 331:659-668.

Kaposzta et al. (2002) "S-Nitrosoglutathione Reduces Asymptomatic Embolization After Carotid Angioplasty", Circulation,106(24):3057-3062.

Kouznetsov et al.. (2005) "Recent Progress in the Synthesis of Quinolines" Current Organic Chemistry 9:141-161.

Lee (2008), "Acetaminophen-related Acute Liver Failure in the United States" Hepatology Research, 38 (Suppl. 1): S3-S8.

Lima et al. (2010), "S-Nitrosylation in Cardiovascular Signaling", Circ Res. 106(4):633-646.

Lipton et al. (Sep. 2001) "S-Nitrosothiols signal the ventilatory response to hypoxia", Nature, 413:171-174.

Liu et al. (Feb. 2004) "Essential Roles of S-Nitrosothiols in Vascular Homeostatsis and Endotoxic Shock", Cell, 116(4):617-628.

Liu et al. (Mar. 2001) "A metabolic enzyme for S-nitrosothiol conserved from bacterial to humans", Nature, 410:490-494.

Madapa et al (2008) "Advances in the synthesis of quinoline and quinoline-annulated ring systems" Current Organic Chemistry 12:1116-1183.

Mphahlele (Jan. 2010) "Synthesis of 2-Arylquinolin-4(1H)-ones and Their Transformation to N-Alkylated and O-Alkylated Derivatives" Journal of Heterocyclic Chemistry 43(2):255-260.

Prince et al. (2010) "The Nitric Oxide Donor S-Nitrosoglutathione Reduces Apoptotic Primary Liver Cell Loss in a Three-Dimensional Perfusion Bioreactor Culture Model Developed for Liver Support" Tissue Eng 16(3):861-866.

Que et al. (Jun. 2005) "Protection from Experimental Asthma by an Endogenous Bronchodilator", Science, 308(5728):1618-1621.

Sandelier (2008); downloaded from the internet: http://www.dtic.mil/gni-bin/GetTRDoc?AD=ADA486097&Location=U2&doc=GetTRDoc.pdf on Feb. 13, 2012). Tandem reduction cyclization of 0-nitrophenyl propargyl alcohols—A novel synthesis of 2-& 2,4-disubstituted quinolines and application to the synthesis of streponigrim, UMI No. 3324767.

Sanghani et al. (2000) "Kinetic Mechanism of Human Glutathioone-Dependent Formaldehyde Dehydrogenase", Biochemistry,39:10720-10729.

Sanghani et al. (2002) "Human Glutathione-Dependent Formaldehyde Dehydrognease. Structures of Apo, Binary, and Inhibitory Ternary Complexes", Biochemistry,41:10778-10786.

(56) References Cited

OTHER PUBLICATIONS

Sanghani et al. (Jul. 11,2009) Kinetic and Cellular Characterization of Novel Inhibitors of S-Nitrosogluthathione Reductase, *J. Biol. Chem.* 284:24354-24362.
Silverman et al. (2004) "The Organic Chemistry of Drug Design and Drug Action" Elsevier pp. 29-32.
Smith et al. (1955) "Studies in detoxication. 65. The metabolism of quinoline. New metabolites of quinoline, with observations on the metabolism of 3-, 5-, and 6-hydroxyquinoline and 2,4-dihydroxyquinoline" Biochem. J. 60(2)284-290.
Staab et al. (2008) "Dual functions of alcohol dehydrogenase 3: implications with focus on formaldehyde dehydrogenase and S-nitroglutathione reductase activities", *Cell Mol. Life Sci*, 65:3950-3960.
Staab et al. (Jun. 15, 2009) "Medium-chain fatty acids and glutathione derivatives as inhibitors of S-nitrosoglutathione reduction mediated by alcohol dehydrogenase 3", Chemico-Biological Interactions 180(1):113-118.
Stamler et al. (Aug. 1992) "Nitric oxide circulates in mammalian plasma primarily as an S-nitrose adduct of serium albumin", *Proc. Natl. Acad. Sci. USA*, 89:7674-7677.
Tanaka et al. (2002) "Crystal Structure of Formaldehyde Dehydrogenase from Pseudomonas putida: the Structural Origin of the Tightly Bound Cofactor in Nicotinoprotein Dehydrogenases" J. Mol. Biol. 324:519-533.
Uotila and Koivusalo (1989) Coenzymes and Cofactors vol. 3: Glutathione, part A., D. Dolphin, ed. pp. 517-551 (New York, John Wiley & Sons).
Zaman et al. (2001) "S-Nitrosoglutathione Increases Cystic Fibrosis Transmembrane Regulator Maturation", *Biochem Biophys Res Commun.*, 284:65-70.

SUBSTITUTED QUINOLINE COMPOUNDS AS S-NITROSOGLUTATHIONE REDUCTASE INHIBITORS

RELATED APPLICATIONS

The application is a continuation of U.S. application Ser. No. 15/097,378, filed Apr. 13, 2016. U.S. application Ser. No. 15/097,378 is a continuation of U.S. application Ser. No. 14/817,329, filed Aug. 4, 2015, now U.S. Pat. No. 9,315,462. U.S. application Ser. No. 14/817,329 is a continuation of U.S. application Ser. No. 14/540,216, filed Nov. 13, 2014, now U.S. Pat. No. 9,139,528. U.S. application Ser. No. 14/540,216 is a continuation application of U.S. application Ser. No. 13/824,430, filed Mar. 18, 2013, now U.S. Pat. No. 8,921,562. U.S. application Ser. No. 13/824,430 is a 35 U.S.C. §371 national phase application of International Application Serial No. PCT/US2011/055200, filed Oct. 7, 2011 (WO 2012/048181). International Application Serial No. PCT/US2011/055200 claims priority to U.S. Provisional Application Ser. No. 61/391,225, filed Oct. 8, 2010 and U.S. Provisional Application Ser. No. 61/423,805, filed Dec. 16, 2010. Each of these applications is incorporated hereby by reference in its entirety.

FIELD OF THE INVENTION

The present invention is directed to novel quinoline compounds, pharmaceutical compositions comprising such compounds, and methods of making and using the same. These compounds are useful as inhibitors of S-nitrosoglutathione reductase (GSNOR).

BACKGROUND

The chemical compound nitric oxide is a gas with chemical formula NO. NO is one of the few gaseous signaling molecules known in biological systems, and plays an important role in controlling various biological events. For example, the endothelium uses NO to signal surrounding smooth muscle in the walls of arterioles to relax, resulting in vasodilation and increased blood flow to hypoxic tissues. NO is also involved in regulating smooth muscle proliferation, platelet function, and neurotransmission, and plays a role in host defense. Although NO is highly reactive and has a lifetime of a few seconds, it can both diffuse freely across membranes and bind to many molecular targets. These attributes make NO an ideal signaling molecule capable of controlling biological events between adjacent cells and within cells.

NO is a free radical gas, which makes it reactive and unstable, thus NO is short lived in vivo, having a half life of 3-5 seconds under physiologic conditions. In the presence of oxygen, NO can combine with thiols to generate a biologically important class of stable NO adducts called S-nitrosothiols (SNO's). This stable pool of NO has been postulated to act as a source of bioactive NO and as such appears to be critically important in health and disease, given the centrality of NO in cellular homeostasis (Stamler et al., *Proc. Natl. Acad. Sci. USA*, 89:7674-7677 (1992)). Protein SNO's play broad roles in the function of cardiovascular, respiratory, metabolic, gastrointestinal, immune, and central nervous system (Foster et al., *Trends in Molecular Medicine*, 9 (4):160-168, (2003)). One of the most studied SNO's in biological systems is S-nitrosoglutathione (GSNO) (Gaston et al., *Proc. Natl. Acad. Sci. USA* 90:10957-10961 (1993)), an emerging key regulator in NO signaling since it is an efficient trans-nitrosating agent and appears to maintain an equilibrium with other S-nitrosated proteins (Liu et al., *Nature*, 410:490-494 (2001)) within cells. Given this pivotal position in the NO-SNO continuum, GSNO provides a therapeutically promising target to consider when NO modulation is pharmacologically warranted.

In light of this understanding of GSNO as a key regulator of NO homeostasis and cellular SNO levels, studies have focused on examining endogenous production of GSNO and SNO proteins, which occurs downstream from the production of the NO radical by the nitric oxide synthetase (NOS) enzymes. More recently there has been an increasing understanding of enzymatic catabolism of GSNO which has an important role in governing available concentrations of GSNO and consequently available NO and SNO's.

Central to this understanding of GSNO catabolism, researchers have recently identified a highly conserved S-nitrosoglutathione reductase (GSNOR) (Jensen et al., *Biochem J.*, 331:659-668 (1998); Liu et al., (2001)). GSNOR is also known as glutathione-dependent formaldehyde dehydrogenase (GSH-FDH), alcohol dehydrogenase 3 (ADH-3) (Uotila and Koivusalo, *Coenzymes and Cofactors*, D. Dolphin, ed. pp. 517-551 (New York, John Wiley & Sons, (1989)), and alcohol dehydrogenase 5 (ADH-5). Importantly GSNOR shows greater activity toward GSNO than other substrates (Jensen et al., (1998); Liu et al., (2001)) and appears to mediate important protein and peptide denitrosating activity in bacteria, plants, and animals. GSNOR appears to be the major GSNO-metabolizing enzyme in eukaryotes (Liu et al., (2001)). Thus, GSNO can accumulate in biological compartments where GSNOR activity is low or absent (e.g., airway lining fluid) (Gaston et al., (1993)).

Yeast deficient in GSNOR accumulate S-nitrosylated proteins which are not substrates of the enzyme, which is strongly suggestive that GSNO exists in equilibrium with SNO-proteins (Liu et al., (2001)). Precise enzymatic control over ambient levels of GSNO and thus SNO-proteins raises the possibility that GSNO/GSNOR may play roles across a host of physiological and pathological functions including protection against nitrosative stress wherein NO is produced in excess of physiologic needs. Indeed, GSNO specifically has been implicated in physiologic processes ranging from the drive to breathe (Lipton et al., *Nature*, 413:171-174 (2001)) to regulation of the cystic fibrosis transmembrane regulator (Zaman et al., *Biochem Biophys Res Commun*, 284:65-70 (2001)), to regulation of vascular tone, thrombosis, and platelet function (de Belder et al., *Cardiovasc Res.*; 28(5):691-4 (1994)), Z. Kaposzta, et al., *Circulation;* 106 (24): 3057-3062, (2002)) as well as host defense (de Jesus-Berrios et al., *Curr. Biol.*, 13:1963-1968 (2003)). Other studies have found that GSNOR protects yeast cells against nitrosative stress both in vitro (Liu et al., (2001)) and in vivo (de Jesus-Berrios et al., (2003)).

Collectively, data suggest GSNO as a primary physiological ligand for the enzyme S-nitrosoglutathione reductase (GSNOR), which catabolizes GSNO and consequently reduces available SNO's and NO in biological systems (Liu et al., (2001)), (Liu et al., *Cell,* 116(4), 617-628 (2004)), and (Que et al., *Science,* 308, (5728):1618-1621 (2005)). As such, this enzyme plays a central role in regulating local and systemic bioactive NO. Since perturbations in NO bioavailability has been linked to the pathogenesis of numerous disease states, including hypertension, atherosclerosis, thrombosis, asthma, gastrointestinal disorders, inflammation, and cancer, agents that regulate GSNOR activity are candidate therapeutic agents for treating diseases associated with NO imbalance.

Nitric oxide (NO), S-nitrosoglutathione (GSNO), and S-nitrosoglutathione reductase (GSNOR) regulate normal lung physiology and contribute to lung pathophysiology. Under normal conditions, NO and GSNO maintain normal lung physiology and function via their anti-inflammatory and bronchodilatory actions. Lowered levels of these mediators in pulmonary diseases such as asthma, chronic obstructive pulmonary disease (COPD) may occur via up-regulation of GSNOR enzyme activity. These lowered levels of NO and GSNO, and thus lowered anti-inflammatory capabilities, are key events that contribute to pulmonary diseases and which can potentially be reversed via GSNOR inhibition.

S-nitrosoglutathione (GSNO) has been shown to promote repair and/or regeneration of mammalian organs, such as the heart (Lima et al., 2010), blood vessels (Lima et al., 2010) skin (Georgii et al., 2010), eye or ocular structures (Haq et al., 2007) and liver (Prince et al., 2010). S-nitrosoglutathione reductase (GSNOR) is the major catabolic enzyme of GSNO. Inhibition of GSNOR is thought to increase endogenous GSNO.

Inflammatory bowel diseases (IBD's), including Crohn's and ulcerative colitis, are chronic inflammatory disorders of the gastrointestinal (GI) tract, in which NO, GSNO, and GSNOR can exert influences. Under normal conditions, NO and GSNO function to maintain normal intestinal physiology via anti-inflammatory actions and maintenance of the intestinal epithelial cell barrier. In IBD, reduced levels of GSNO and NO are evident and likely occur via up-regulation of GSNOR activity. The lowered levels of these mediators contribute to the pathophysiology of IBD via disruption of the epithelial barrier via dysregulation of proteins involved in maintaining epithelial tight junctions. This epithelial barrier dysfunction, with the ensuing entry of microorganisms from the lumen, and the overall lowered anti-inflammatory capabilities in the presence of lowered NO and GSNO, are key events in IBD progression that can be potentially influenced by targeting GSNOR.

Cell death is the crucial event leading to clinical manifestation of hepatotoxicity from drugs, viruses and alcohol. Glutathione (GSH) is the most abundant redox molecule in cells and thus the most important determinant of cellular redox status. Thiols in proteins undergo a wide range of reversible redox modifications during times of exposure to reactive oxygen and reactive nitrogen species, which can affect protein activity. The maintenance of hepatic GSH is a dynamic process achieved by a balance between rates of GSH synthesis, GSH and GSSG efflux, GSH reactions with reactive oxygen species and reactive nitrogen species and utilization by GSH peroxidase. Both GSNO and GSNOR play roles in the regulation of protein redox status by GSH.

Acetaminophen overdoses are the leading cause of acute liver failure (ALF) in the United States, Great Britain and most of Europe. More than 100,000 calls to the U.S. Poison Control Centers, 56,000 emergency room visits, 2600 hospitalizations, nearly 500 deaths are attributed to acetaminophen in this country annually. Approximately, 60% recover without needing a liver transplant, 9% are transplanted and 30% of patients succumb to the illness. The acetaminophen-related death rate exceeds by at least three-fold the number of deaths due to all other idiosyncratic drug reactions combined (Lee, Hepatol Res 2008; 38 (Suppl. 1):S3-S8).

Liver transplantation has become the primary treatment for patients with fulminant hepatic failure and end-stage chronic liver disease, as well as certain metabolic liver diseases. Thus, the demand for transplantation now greatly exceeds the availability of donor organs. It has been estimated that more than 18 000 patients are currently registered with the United Network for Organ Sharing (UNOS) and that an additional 9000 patients are added to the liver transplant waiting list each year, yet less than 5000 cadaveric donors are available for transplantation.

Currently, there is a great need in the art for diagnostics, prophylaxis, ameliorations, and treatments for medical conditions relating to increased NO synthesis and/or increased NO bioactivity. In addition, there is a significant need for novel compounds, compositions, and methods for preventing, ameliorating, or reversing other NO-associated disorders. The present invention satisfies these needs.

SUMMARY

The present invention provides novel quinoline compounds. These compounds are useful as S-nitrosoglutathione reductase ("GSNOR") inhibitors. The invention encompasses pharmaceutically acceptable salts, stereoisomers, prodrugs, metabolites, and N-oxides of the described compounds. Also encompassed by the invention are pharmaceutical compositions comprising at least one compound of the invention and at least one pharmaceutically acceptable carrier.

The compositions of the present invention can be prepared in any suitable pharmaceutically acceptable dosage form.

The present invention provides a method for inhibiting GSNOR in a subject in need thereof. Such a method comprises administering a therapeutically effective amount of a pharmaceutical composition comprising at least one GSNOR inhibitor or a pharmaceutically acceptable salt, stereoisomer, prodrug, metabolite or N-oxide thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a disorder ameliorated by NO donor therapy in a subject in need thereof. Such a method comprises administering a therapeutically effective amount of a pharmaceutical composition comprising at least one GSNOR inhibitor or a pharmaceutically acceptable salt, stereoisomer, prodrug, metabolite, or N-oxide thereof, in combination with at least one pharmaceutically acceptable carrier. The GSNOR inhibitor can be a novel compound according to the invention, or it can be a known compound which previously was not known to be an inhibitor of GSNOR.

The present invention also provides a method of treating a cell proliferative disorder in a subject in need thereof. Such a method comprises administering a therapeutically effective amount of a pharmaceutical composition comprising at least one GSNOR inhibitor or a pharmaceutically acceptable salt, stereoisomer, prodrug, metabolite, or N-oxide thereof, in combination with at least one pharmaceutically acceptable carrier. The GSNOR inhibitor can be a novel compound according to the invention, or it can be a known compound which previously was not known to be an inhibitor of GSNOR.

The methods of the invention encompass administration with one or more secondary active agents. Such administration can be sequential or in a combination composition.

Although methods and materials similar or equivalent to those described herein can be used in the practice or testing of the present invention, suitable methods and materials are described below. All publicly available publications, patent applications, patents, and other references mentioned herein are incorporated by reference in their entirety. In the case of conflict, the present specification, including definitions, will control.

Both the foregoing summary and the following detailed description are exemplary and explanatory and are intended to provide further details of the compositions and methods as claimed. Other objects, advantages, and novel features will be readily apparent to those skilled in the art from the following detailed description.

DETAILED DESCRIPTION

A. Overview of the Invention

Until recently, S-nitrosoglutathione reductase (GSNOR) was known to oxidize the formaldehyde glutathione adduct, S-hydroxymethylglutathione. GSNOR has since been identified in a variety of bacteria, yeasts, plants, and animals and is well conserved. The proteins from *E. coli, S. cerevisiae* and mouse macrophages share over 60% amino acid sequence identity. GSNOR activity (i.e., decomposition of GSNO when NADH is present as a required cofactor) has been detected in *E. coli*, in mouse macrophages, in mouse endothelial cells, in mouse smooth muscle cells, in yeasts, and in human HeLa, epithelial, and monocyte cells. Human GSNOR nucleotide and amino acid sequence information can be obtained from the National Center for Biotechnology Information (NCBI) databases under Accession Nos. M29872, NM_000671. Mouse GSNOR nucleotide and amino acid sequence information can be obtained from NCBI databases under Accession Nos. NM_007410. In the nucleotide sequence, the start site and stop site are underlined. CDS designates coding sequence. SNP designates single nucleotide polymorphism. Other related GSNOR nucleotide and amino acid sequences, including those of other species, can be found in U.S. Patent Application 2005/0014697.

In accord with the present invention, GSNOR has been shown to function in vivo and in vitro to metabolize S-nitrosoglutathione (GSNO) and protein S-nitrosothiols (SNOs) to modulate NO bioactivity, by controlling the intracellular levels of low mass NO donor compounds and preventing protein nitrosylation from reaching toxic levels.

Based on this, it follows that inhibition of this enzyme potentiates bioactivity in diseases in which NO donor therapy is indicated, inhibits the proliferation of pathologically proliferating cells, and increases NO bioactivity in diseases where this is beneficial.

The present invention provides pharmaceutical agents that are potent inhibitors of GSNOR. In particular, provided are substituted quinoline analogs having the structures depicted below (Formula I), or a pharmaceutically acceptable salt, stereoisomer, prodrug, metabolite, or N-oxide thereof.

Formula I

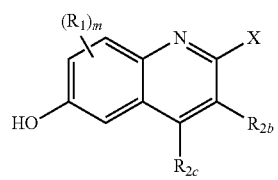

wherein
m is selected from the group consisting of 0, 1, 2, or 3;
$R_1$ is independently selected from the group consisting of chloro, fluoro, bromo, cyano, and methoxy;

$R_{2b}$ and $R_{2c}$ are independently selected from the group consisting of hydrogen, halogen, $C_1$-$C_3$ alkyl, fluorinated $C_1$-$C_3$ alkyl, cyano, $C_1$-$C_3$ alkoxy, and $N(CH_3)_2$;
X is selected from the group consisting of

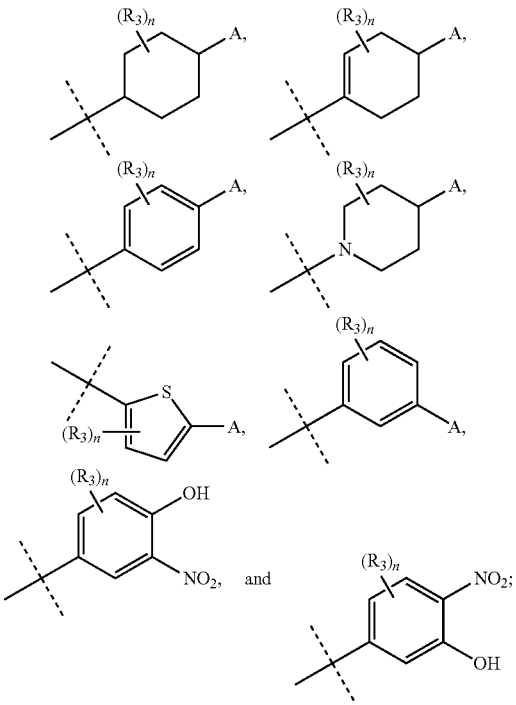

n is selected from the group consisting of 0, 1, and 2;
$R_3$ is independently selected from the group consisting of halogen, $C_1$-$C_3$ alkyl, fluorinated $C_1$-$C_3$ alkyl, cyano, hydroxy, $C_1$-$C_3$ alkoxy, and $NR_4R_{4'}$ where $R_4$ and $R_{4'}$ are independently selected from the group consisting of $C_1$-$C_3$ alkyl, or $R_4$ when taken together with $R_{4'}$ form a ring with 3 to 6 members; and
A is selected from the group consisting of

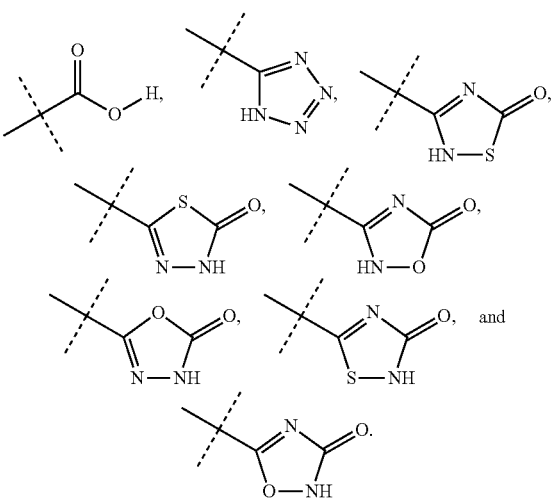

As used in this context, the term "analog" refers to a compound having similar chemical structure and function as compounds of Formula I that retains the quinoline ring.

Some quinoline analogs of the invention can also exist in various isomeric forms, including configurational, geometric, and conformational isomers, as well as existing in various tautomeric forms, particularly those that differ in the point of attachment of a hydrogen atom. As used herein, the term "isomer" is intended to encompass all isomeric forms of a compound including tautomeric forms of the compound.

Illustrative compounds having asymmetric centers can exist in different enantiomeric and diastereomeric forms. A compound can exist in the form of an optical isomer or a diastereomer. Accordingly, the invention encompasses compounds in the forms of their optical isomers, diastereomers and mixtures thereof, including racemic mixtures.

It should be noted that if there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of the described compound.

B. S-Nitrosoglutathione Reductase Inhibitors

1. Inventive Compounds

In one of its aspects the present invention provides compounds having the structure shown in Formula I, or a pharmaceutically acceptable salt, stereoisomer, prodrug, metabolite, or N-oxide thereof:

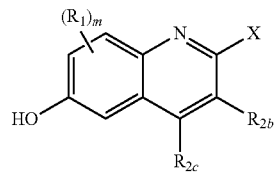

Formula I wherein
m is selected from the group consisting of 0, 1, 2, or 3;
$R_1$ is independently selected from the group consisting of chloro, fluoro, bromo, cyano, and methoxy;
$R_{2b}$ and $R_{2c}$ are independently selected from the group consisting of hydrogen, halogen, $C_1$-$C_3$ alkyl, fluorinated $C_1$-$C_3$ alkyl, cyano, $C_1$-$C_3$ alkoxy, and $N(CH_3)_2$;
X is selected from the group consisting of

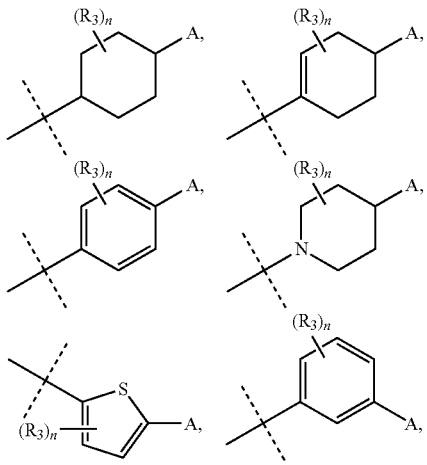

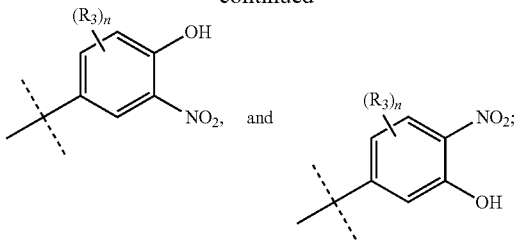

n is selected from the group consisting of 0, 1, and 2;
$R_3$ is independently selected from the group consisting of halogen, $C_1$-$C_3$ alkyl, fluorinated $C_1$-$C_3$ alkyl, cyano, hydroxy, $C_1$-$C_3$ alkoxy, and $NR_4R_{4'}$ where $R_4$ and $R_{4'}$ are independently selected from the group consisting of $C_1$-$C_3$ alkyl, or $R_4$ when taken together with $R_{4'}$ form a ring with 3 to 6 members; and
A is selected from the group consisting of

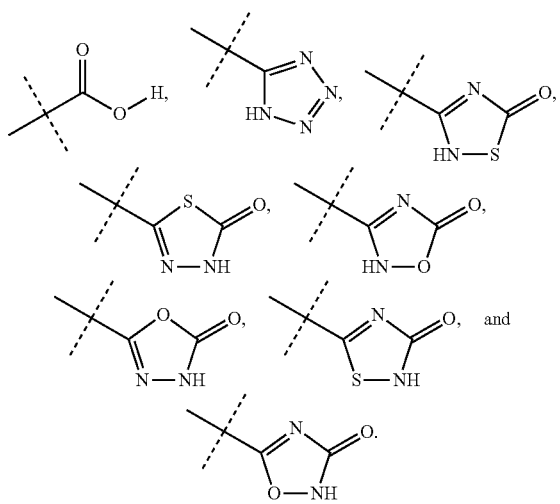

In a further aspect of the invention, $R_1$ is independently selected from the group consisting of chloro, fluoro, and bromo; $R_3$ is independently selected from the group consisting of halogen, $C_1$-$C_3$ alkyl, fluorinated $C_1$-$C_3$ alkyl, cyano, $C_1$-$C_3$ alkoxy, and $NR_4R_{4'}$ where $R_4$ and $R_{4'}$ are independently selected from the group consisting of $C_1$-$C_3$ alkyl, or $R_4$ when taken together with $R_{4'}$ form a ring with 3 to 6 members; and X is selected from the group consisting of

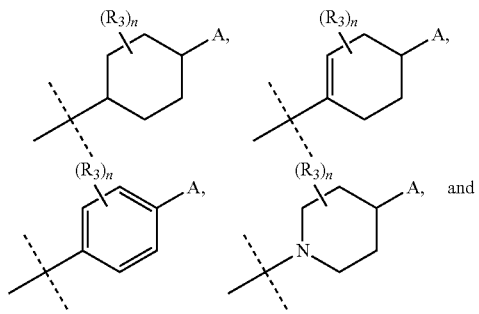

-continued

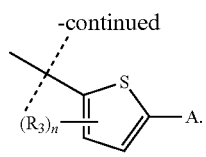

In a further aspect of the invention, $R_3$ is independently selected from the group consisting of halogen, $C_1$-$C_3$ alkyl, fluorinated $C_1$-$C_3$ alkyl, cyano, $C_1$-$C_3$ alkoxy, and $NR_4R_{4'}$ where $R_4$ and $R_{4'}$ are methyl, or alternatively together with the said N form the ring aziridin-1-yl or morpholino.

In a further aspect of the invention, m is selected from the group consisting of 0 and 1; $R_{2b}$ and $R_{2c}$ are independently selected from the group consisting of hydrogen, chloro, fluoro, methyl, trifluoromethyl, cyano, methoxy, and $N(CH_3)_2$; n is selected from the group consisting of 0 and 1; and $R_3$ is independently selected from the group consisting of fluoro, chloro, bromo, methyl, trifluoromethyl, cyano, hydroxy, methoxy, and $N(CH_3)_2$.

In a further aspect of the invention, X is

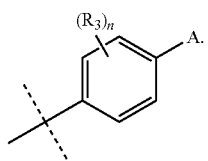

In a further aspect of the invention, A is COOH.
In a further aspect of the invention, suitable compounds of Formula I include, but are not limited to:
4-(6-hydroxy-3-methylquinolin-2-yl)benzoic acid;
2-(4-(1H-tetrazol-5-yl)phenyl)-3-methylquinolin-6-ol;
4-(6-hydroxyquinolin-2-yl)benzoic acid;
2-(4-(1H-tetrazol-5-yl)phenyl)quinolin-6-ol;
1-(6-hydroxyquinolin-2-yl)piperidine-4-carboxylic acid;
(1r,4r)-4-(6-hydroxyquinolin-2-yl)cyclohexanecarboxylic acid;
(1s,4s)-4-(6-hydroxyquinolin-2-yl)cyclohexanecarboxylic acid;
3-chloro-4-(6-hydroxyquinolin-2-yl)benzoic acid;
2-chloro-4-(6-hydroxyquinolin-2-yl)benzoic acid;
2-fluoro-4-(6-hydroxyquinolin-2-yl)benzoic acid;
2-(4-(2H-tetrazol-5-yl)phenyl)-4-chloroquinolin-6-ol;
3-(4-(6-hydroxyquinolin-2-yl)phenyl)-1,2,4-oxadiazol-5 (2H)-one;
3-fluoro-4-(6-hydroxyquinolin-2-yl)benzoic acid;
4-(6-hydroxyquinolin-2-yl)-3-methoxybenzoic acid;
5-(6-hydroxyquinolin-2-yl)thiophene-2-carboxylic acid;
4-(6-hydroxyquinolin-2-yl)cyclohex-3-enecarboxylic acid;
4-(3-fluoro-6-hydroxyquinolin-2-yl)benzoic acid;
4-(4-chloro-3-fluoro-6-hydroxyquinolin-2-yl)benzoic acid;
4-(3-chloro-6-hydroxyquinolin-2-yl)benzoic acid;
3-(2-fluoro-4-(6-hydroxyquinolin-2-yl)phenyl)-1,2,4-oxadiazol-5(4H)-one;
3-(3-fluoro-4-(6-hydroxyquinolin-2-yl)phenyl)-1,2,4-oxadiazol-5(4H)-one;
4-(4-chloro-6-hydroxyquinolin-2-yl)benzoic acid;
2-(2-chloro-4-(2H-tetrazol-5-yl)phenyl)quinolin-6-ol;
5-(4-(6-hydroxyquinolin-2-yl)phenyl)-1,3,4-oxadiazol-2 (3H)-one;
3-(dimethylamino)-4-(6-hydroxyquinolin-2-yl)benzoic acid;
4-(4-fluoro-6-hydroxyquinolin-2-yl)benzoic acid;
4-(6-hydroxyquinolin-2-yl)-3-methylbenzoic acid;
4-(3-chloro-6-hydroxyquinolin-2-yl)-3-fluorobenzoic acid;
3-(4-(6-hydroxyquinolin-2-yl)phenyl)-1,2,4-thiadiazol-5 (2H)-one;
4-(6-hydroxyquinolin-2-yl)-3-(trifluoromethyl)benzoic acid;
4-(6-hydroxy-3-(trifluoromethyl)quinolin-2-yl)benzoic acid;
2-(4-carboxyphenyl)-6-hydroxyquinoline 1-oxide;
5-(4-(6-hydroxyquinolin-2-yl)phenyl)-1,3,4-thiadiazol-2 (3H)-one;
5-(4-(6-hydroxyquinolin-2-yl)phenyl)-1,2,4-oxadiazol-3 (2H)-one;
(1r,4r)-4-(3-chloro-6-hydroxyquinolin-2-yl)cyclohexanecarboxylic acid;
(1s,4s)-4-(3-chloro-6-hydroxyquinolin-2-yl)cyclohexanecarboxylic acid;
3-chloro-4-(4-fluoro-6-hydroxyquinolin-2-yl)benzoic acid;
2-(5-(2H-tetrazol-5-yl)thiophen-2-yl)quinolin-6-ol;
5-(4-(6-hydroxyquinolin-2-yl)phenyl)-1,2,4-thiadiazol-3 (2H)-one;
3-fluoro-4-(4-fluoro-6-hydroxyquinolin-2-yl)benzoic acid;
1-(6-hydroxy-3-(trifluoromethyl)quinolin-2-yl)piperidine-4-carboxylic acid;
4-(5-chloro-6-hydroxyquinolin-2-yl)benzoic acid;
(1r,4r)-4-(6-hydroxy-3-(trifluoromethyl)quinolin-2-yl)cyclohexanecarboxylic acid;
(1s,4s)-4-(6-hydroxy-3-(trifluoromethyl)quinolin-2-yl)cyclohexanecarboxylic acid;
4-(5-bromo-6-hydroxyquinolin-2-yl)benzoic acid;
3-bromo-4-(6-hydroxyquinolin-2-yl)benzoic acid;
4-(4-(dimethylamino)-6-hydroxyquinolin-2-yl)benzoic acid;
4-(4-fluoro-6-hydroxyquinolin-2-yl)-3-methoxybenzoic acid;
3-cyano-4-(6-hydroxyquinolin-2-yl)benzoic acid;
2-(4-carboxy-2-chlorophenyl)-6-hydroxyquinoline 1-oxide;
4-(4-amino-6-hydroxyquinolin-2-yl)benzoic acid;
4-(3-cyano-6-hydroxyquinolin-2-yl)benzoic acid;
4-(5-fluoro-6-hydroxyquinolin-2-yl)benzoic acid;
4-(8-fluoro-6-hydroxyquinolin-2-yl)benzoic acid;
3-hydroxy-4-(6-hydroxyquinolin-2-yl)benzoic acid; and
3-fluoro-4-(5-fluoro-6-hydroxyquinolin-2-yl)benzoic acid.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

It is to be understood that isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

2. Representative Compounds

Examples 1-56 list representative novel quinoline analogs of Formula I. The synthetic methods that can be used to prepare each compound are detailed in Examples 1-56, with reference to the synthetic schemes depicted before Example 1, and reference to intermediates described in Example 57. Supporting mass spectrometry data and/or proton NMR data for each compound is also included in Examples 1-56. GSNOR inhibitor activity was determined by the assay described in Example 58 and $IC_{50}$ values were obtained. GSNOR inhibitor compounds in Examples 1-56 had an $IC_{50}$ of about <10 µM. GSNOR inhibitor compounds in Examples 1-4, 6, 8, 10-14, 16-35, 37-43, 45-50, and 52-56 had an $IC_{50}$ of about <0.5 µM. GSNOR inhibitor compounds in Examples 1-4, 8, 10-14, 17-28, 30, 31, 37, 40-41, 43, 46, 48-49, and 52-56 had an $IC_{50}$ of about <0.1 µM.

C. Definitions

As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The term "acyl" includes compounds and moieties that contain the acetyl radical ($CH_3CO$—) or a carbonyl group to which a straight or branched chain lower alkyl residue is attached.

The term "alkyl" as used herein refers to a straight or branched chain, saturated hydrocarbon having the indicated number of carbon atoms. For example, ($C_1$-$C_6$) alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein.

The term "alkenyl" as used herein refers to a straight or branched chain unsaturated hydrocarbon having the indicated number of carbon atoms and at least one double bond. Examples of a ($C_2$-$C_8$) alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein.

The term "alkynyl" as used herein refers to a straight or branched chain unsaturated hydrocarbon having the indicated number of carbon atoms and at least one triple bond. Examples of a ($C_2$-$C_8$) alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne, and 4-octyne. An alkynyl group can be unsubstituted or optionally substituted with one or more substituents as described herein.

The term "alkoxy" as used herein refers to an —O-alkyl group having the indicated number of carbon atoms. For example, a ($C_1$-$C_6$) alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aminoalkyl" as used herein, refers to an alkyl group (typically one to six carbon atoms) wherein one or more of the $C_1$-$C_6$ alkyl group's hydrogen atoms is replaced with an amine of formula —N($R^c$)$_2$, wherein each occurrence of $R^c$ is independently —H or ($C_1$-$C_6$) alkyl. Examples of aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2CH_2N$ ($CH_3$)$_2$, t-butylaminomethyl, isopropylaminomethyl, and the like.

The term "aryl" as used herein refers to a 5- to 14-membered monocyclic, bicyclic, or tricyclic aromatic ring system. Examples of an aryl group include phenyl and naphthyl. An aryl group can be unsubstituted or optionally substituted with one or more substituents as described herein below. Examples of aryl groups include phenyl or aryl heterocycles such as, pyrrole, furan, thiophene, thiazole, isothiazole, imidazole, triazole, tetrazole, pyrazole, oxazole, isoxazole, pyridine, pyrazine, pyridazine, and pyrimidine, and the like.

As used herein, the term "bioactivity" indicates an effect on one or more cellular or extracellular process (e.g., via binding, signaling, etc.) which can impact physiological or pathophysiological processes.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxy" or "carboxyl" means a —COOH group or carboxylic acid.

"Acidic moiety" as used herein is defined as a carboxylic acid or a carboxylic acid bioisostere. Bioisosteres are substituents or groups with similar physical or chemical properties which produce broadly similar biological properties to a chemical compound. For a review of bioisosteres, see *J. Med. Chem*, 2011, 54, 2529-2591. Examples of "acidic moiety" include but are not limited to

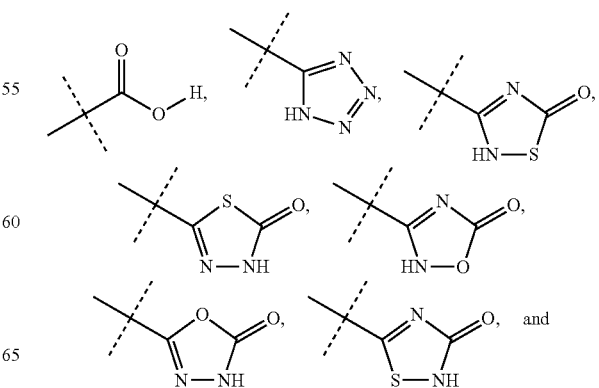

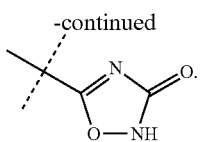

"Pharmacophore" is defined as "a set of structural features in a molecule that is recognized at a receptor site and is responsible for that molecule's biological activity" (Gund, Prog. Mol. Subcell. Biol., 5: pp 117-143 (1977)).

The term "$C_m$-$C_n$" means "m" number of carbon atoms to "n" number of carbon atoms. For example, the term "$C_1$-$C_6$" means one to six carbon atoms ($C_1$, $C_2$, $C_3$, $C_4$, $C_5$, or $C_6$). The term "$C_2$-$C_6$" includes two to six carbon atoms ($C_2$, $C_3$, $C_4$, $C_5$, or $C_6$). The term "$C_3$-$C_6$" includes three to six carbon atoms ($C_3$, $C_4$, $C_5$, or $C_6$).

The term "cycloalkyl" as used herein refers to a 3- to 14-membered saturated or unsaturated non-aromatic monocyclic, bicyclic, or tricyclic hydrocarbon ring system. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, tetrahydroheptalene, (1s,3s)-bicyclo[1.1.0]butane, bicyclo[1.1.1]pentane, bicyclo[2.1.1]hexane, Bicyclo[2.2.1]heptane, bicyclo[2.2.2]octane, bicyclo[3.1.1]heptane, bicyclo[3.2.1]octane, bicyclo[3.3.1]nonane, bicyclo[3.3.2]decane, bicyclo [3.3.]undecane, bicyclo[4.2.2]decane, and bicyclo[4.3.1]decane. A cycloalkyl group can be unsubstituted or optionally substituted with one or more substituents as described herein below.

The term "halogen" includes fluorine, bromine, chlorine, iodine, etc.

The term "haloalkyl," as used herein, refers to a $C_1$-$C_6$ alkyl group wherein from one or more of the $C_1$-$C_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroalkyl," by itself or in combination with another term, means, unless otherwise stated, a stable straight or branched chain alkyl, or combinations thereof, consisting of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N, and S can be placed at any position of the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, and —$CH_2$—CH=N—$OCH_3$. Up to two heteroatoms can be consecutive, for example, —$CH_2$—NH—$OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$.

To further illustrate the definition of a heteroalkyl group, where the heteroatom is oxygen, a heteroalkyl group can be an oxyalkyl group. For instance, ($C_2$-$C_5$) oxyalkyl is meant to include, for example —$CH_2$—O—$CH_3$ (a $C_3$-oxyalkyl group with two carbon atoms and one oxygen replacing a carbon atom), —$CH_2CH_2CH_2CH_2OH$, —$OCH_2CH_2OCH_2CH_2OH$, —$OCH_2CH(OH)CH_2OH$, and the like.

The term "heteroaryl" as used herein refers to an aromatic heterocycle ring of 5 to 14 members and having at least one heteroatom selected from nitrogen, oxygen, and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thienyl, benzothienyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl and oxazolyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" refers to 3- to 14-membered ring systems which are either saturated, unsaturated, or aromatic, and which contains from 1 to 4 heteroatoms independently selected from nitrogen, oxygen, and sulfur, and wherein the nitrogen and sulfur heteroatoms can be optionally oxidized, and the nitrogen heteroatom can be optionally quaternized, including monocyclic, bicyclic, and tricyclic ring systems. The bicyclic and tricyclic ring systems may encompass a heterocycle or heteroaryl fused to a benzene ring. The heterocycle can be attached via any heteroatom or carbon atom, where chemically acceptable. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thienyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl. A heterocycle group can be unsubstituted or optionally substituted with one or more substituents as described herein below.

The term "heterocycloalkyl," by itself or in combination with other terms, represents, unless otherwise stated, cyclic versions of "heteroalkyl." Additionally, a heteroatom can occupy the position at which the heterocycle is attached to the remainder of the molecule. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "hydroxyalkyl," as used herein, refers to an alkyl group having the indicated number of carbon atoms wherein one or more of the hydrogen atoms in the alkyl group is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

The term "hydroxy" or "hydroxyl" includes groups with an —OH or —O$^-$.

As used herein, N-oxide, or amine oxide, refers to a compound derived from a tertiary amine by the attachment of one oxygen atom to the nitrogen atom, R$_3$N$^+$—O$^-$. By extension the term includes the analogous derivatives of primary and secondary amines.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. In some embodiments, a stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

As used herein, "protein" is used synonymously with "peptide," "polypeptide," or "peptide fragment". A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, "modulate" is meant to refer to an increase or decrease in the levels of a peptide or a polypeptide, or to increase or decrease the stability or activity of a peptide or a polypeptide. The term "inhibit" is meant to refer to a decrease in the levels of a peptide or a polypeptide or to a decrease in the stability or activity of a peptide or a polypeptide. In preferred embodiments, the peptide which is modulated or inhibited is S-nitrosoglutathione (GSNO) or protein S-nitrosothiols (SNOs).

As used here, the terms "nitric oxide" and "NO" encompass uncharged nitric oxide and charged nitric oxide species, particularly including nitrosonium ion (NO$^+$) and nitroxyl ion (NO$^-$). The reactive form of nitric oxide can be provided by gaseous nitric oxide. Compounds having the structure X—NO$_y$, wherein X is a nitric oxide releasing, delivering, or transferring moiety, including any and all such compounds which provide nitric oxide to its intended site of action in a form active for their intended purpose, and Y is 1 or 2.

Repair" means recovering of structural integrity and normal physiologic function. By way of example, the oral and upper airway respiratory epithelium can repair damage done by thermal injury or viral infection.

"Regeneration" means the ability of an organ to enter non-malignant cellular, vascular and stromal growth to restore functional organ tissue. By way of example, wound healing involves regeneration of tissue and organs (e.g. skin, gastric and intestinal mucosa), as does bone following fracture, and the liver following partial surgical removal and exposure to infectious or toxic insult.

As utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

A "pharmaceutically acceptable salt" or "salt" of a compound of the invention is a product of the disclosed compound that contains an ionic bond, and is typically produced by reacting the disclosed compound with either an acid or a base, suitable for administering to a subject. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, and K, alkali earth metal salts such as Mg or Ca, or organic amine salts.

A "pharmaceutical composition" is a formulation comprising the disclosed compounds in a form suitable for administration to a subject. A pharmaceutical composition of the invention is preferably formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

Substituents for the groups referred to as alkyl, heteroalkyl, alkylene, alkenyl, alkynyl, cycloalkyl, heterocycloalkyl, cycloalkenyl, and heterocycloalkenyl can be selected from a variety of groups including —OR$^{d'}$, =O, =NR$^{d'}$, =N—OR$^{d'}$, —NR$^{d'}$R$^{d''}$, —SR$^{d'}$, -halo, —SiR$^{d'}$R$^{d''}$R$^{d'''}$, —OC(O)R$^{d'}$, —C(O)R$^{d'}$, —CO$_2$R$^{d'}$, —CONR$^{d'}$R$^{d''}$, —OC(O)NR$^{d'}$R$^{d''}$, —NR$^{d''}$C(O)R$^{d'}$, —NR$^{d''}$C(O)NR$^{d'}$R$^{d''}$, —NR$^{d'''}$SO$_2$NR$^{d'}$R$^{d''}$, —NR$^{d''}$CO$_2$R$^{d'}$, —NHC(NH$_2$)=NH, —NR$^{a'}$C(NH$_2$)=NH, —NHC(NH$_2$)=NR$^{d'}$, —S(O)R$^{d'}$, —SO$_2$R$^{d'}$, —SO$_2$NR$^{d'}$R$^{d''}$, —NR$^{d'''}$SO$_2$R$^{d'}$, —CN, and —NO$_2$, in a number ranging from zero to three, with those groups having zero, one or two substituents being exemplary.

R$^{d'}$, R$^{d''}$, and R$^{d'''}$ each independently refer to hydrogen, unsubstituted (C$_1$-C$_8$)alkyl, unsubstituted hetero(C$_1$-C$_8$) alkyl, unsubstituted aryl, and aryl substituted with one to three substituents selected from -halo, unsubstituted alkyl, unsubstituted alkoxy, unsubstituted thioalkoxy, and unsubstituted aryl (C$_1$-C$_4$)alkyl. When R$^{d'}$ and R$^{d''}$ are attached to the same nitrogen atom, they can be combined with the nitrogen atom to form a 5-, 6-, or 7-membered ring. For example, —NR$^{d'}$R$^{d''}$ can represent 1-pyrrolidinyl or 4-morpholinyl.

Typically, an alkyl or heteroalkyl group will have from zero to three substituents, with those groups having two or fewer substituents being exemplary of the present invention.

An alkyl or heteroalkyl radical can be unsubstituted or monosubstituted. In some embodiments, an alkyl or heteroalkyl radical will be unsubstituted.

Exemplary substituents for the alkyl and heteroalkyl radicals include, but are not limited to —$OR^{d'}$, =O, =$NR^{d'}$, =N—$OR^{d'}$, —$NR^{d'}R^{d''}$, —$SR^{d'}$, -halo, —$SiR^{d'}R^{d''}R^{d'''}$, —OC(O)$R^{d'}$, —C(O)$R^{d'}$, —$CO_2R^{d'}$, —CONR$^{d'}R^{d''}$, —OC(O)NR$^{d'}R^{d''}$, —NR$^{d''}$C(O)$R^{d'}$, —NR$^{d''}$C(O)NR$^{d'}R^{d''}$, —NR$^{d'''}SO_2NR^{d'}R^{d''}$, —NR$^{d''}CO_2R^{d'}$, —NHC(NH$_2$)=NH, —NR$^{a'}$C(NH$_2$)=NH, —NHC(NH$_2$)=NR$^{d'}$, —S(O)$R^{d'}$, —$SO_2R^{d'}$, —$SO_2NR^{d'}R^{d''}$, —NR$^{d''}SO_2R^{d'}$, —CN, and —$NO_2$, where $R^{d'}$, $R^{d''}$, and $R^{d'''}$ are as defined above. Typical substituents can be selected from: —$OR^{d'}$, =O, —$NR^{d'}R^{d''}$, -halo, —OC(O)$R^{d'}$, —$CO_2R^{d'}$, —C(O)NR$^{d'}R^{d''}$, —OC(O)NR$^{d'}R^{d''}$, —NR$^{d''}$C(O)$R^{d'}$, —NR$^{d''}CO_2R^{d'}$, —NR$^{d'''}SO_2NR^{d'}R^{d''}$, —$SO_2R^{d'}$, —$SO_2NR^{d'}R^{d''}$, —NR$^{d''}SO_2R^{d'}$, —CN, and —$NO_2$.

Similarly, substituents for the aryl and heteroaryl groups are varied and selected from: -halo, —$OR^{e'}$, —OC(O)$R^{e'}$, —NR$^{e'}R^{e''}$, —$SR^{e'}$, —$R^{e'}$, —CN, —$NO_2$, —$CO_2R^{e'}$, —C(O)NR$^{e'}R^{e''}$, —C(O)$R^{e'}$, —OC(O)NR$^{e'}R^{e''}$, —NR$^{e''}$C(O)$R^{e'}$, —NR$^{e''}CO_2R^{e'}$, —NR$^{e'''}$C(O)NR$^{e'}R^{e''}$, —NR$^{e'''}SO_2NR^{e'}R^{e''}$, —NHC(NH$_2$)=NH, —NR$^{e'}$C(NH$_2$)=NH, —NH—C(NH$_2$)=NR$^{e'}$, —S(O)$R^{e'}$, —$SO_2R^{e'}$, —$SO_2NR^{e'}R^{e''}$, —NR$^{e''}SO_2R^{e'}$, —$N_3$, —CH(Ph)$_2$, perfluoroalkoxy, and perfluoro($C_1$-$C_4$)alkyl, in a number ranging from zero to the total number of open valences on the aromatic ring system.

$R^{e'}$, $R^{e''}$ and $R^{e'''}$ are independently selected from hydrogen, unsubstituted ($C_1$-$C_8$) alkyl, unsubstituted hetero($C_1$-$C_8$) alkyl, unsubstituted aryl, unsubstituted heteroaryl, unsubstituted aryl($C_1$-$C_4$) alkyl, and unsubstituted aryloxy ($C_1$-$C_4$) alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Two of the substituents on adjacent atoms of an aryl or heteroaryl ring in an aryl or heteroaryl group as described herein may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -J-(CH$_2$)$_r$—K—, wherein J and K are independently —CH$_2$—, —O—, —NH—, —S—, —S(O)—, —S(O)$_2$—, —S(O)$_2$NR$^{f'}$—, or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR$^{f'}$—, —S—, —S(O)—, —S(O)$_2$—, or —S(O)$_2$NR$^{a'}$—. The substituent $R^{f'}$ in —NR$^{f'}$— and —S(O)$_2$NR$^{f'}$— is selected from hydrogen or unsubstituted ($C_1$-$C_6$) alkyl.

"Stable compound" and "stable structure" are meant to indicate a compound that is sufficiently robust to survive isolation to a useful degree of purity from a reaction mixture, and formulation into an efficacious therapeutic agent.

As used herein the term "therapeutically effective amount" generally means the amount necessary to ameliorate at least one symptom of a disorder to be prevented, reduced, or treated as described herein. The phrase "therapeutically effective amount" as it relates to the GSNOR inhibitors of the present invention shall mean the GSNOR inhibitor dosage that provides the specific pharmacological response for which the GSNOR inhibitor is administered in a significant number of subjects in need of such treatment. It is emphasized that a therapeutically effective amount of a GSNOR inhibitor that is administered to a particular subject in a particular instance will not always be effective in treating the conditions/diseases described herein, even though such dosage is deemed to be a therapeutically effective amount by those of skill in the art.

The term "biological sample" includes, but is not limited to, samples of blood (e.g., serum, plasma, or whole blood), urine, saliva, sweat, breast milk, vaginal secretions, semen, hair follicles, skin, teeth, bones, nails, or other secretions, body fluids, tissues, or cells. In accordance with the invention, the levels of the GSNOR in the biological sample can be determined by the methods described in U.S. Patent Application Publication No. 2005/0014697.

D. Pharmaceutical Compositions

The invention encompasses pharmaceutical compositions comprising at least one compound of the invention described herein and at least one pharmaceutically acceptable carrier. Suitable carriers are described in "Remington: The Science and Practice, Twentieth Edition," published by Lippincott Williams & Wilkins, which is incorporated herein by reference. Pharmaceutical compositions according to the invention may also comprise one or more non-inventive compound active agents.

The pharmaceutical compositions of the invention can comprise novel compounds described herein, the pharmaceutical compositions can comprise known compounds which previously were not known to have GSNOR inhibitor activity, or a combination thereof.

The compounds of the invention can be utilized in any pharmaceutically acceptable dosage form, including, but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the compounds of the invention described herein can be formulated: (a) for administration selected from the group consisting of oral, pulmonary, intravenous, intra-arterial, intrathecal, intra-articular, rectal, ophthalmic, colonic, parenteral, otic, intracisternal, intravaginal, intraperitoneal, local, buccal, nasal, and topical administration; (b) into a dosage form selected from the group consisting of liquid dispersions, gels, aerosols, ointments, creams, tablets, sachets, and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

For respiratory infections, an inhalation formulation can be used to achieve high local concentrations. Formulations suitable for inhalation include dry power or aerosolized or vaporized solutions, dispersions, or suspensions capable of being dispensed by an inhaler or nebulizer into the endobronchial or nasal cavity of infected patients to treat upper and lower respiratory bacterial infections.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol, or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates, or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes, or multiple dose vials made of glass or plastic.

Pharmaceutical compositions suitable for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.), or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent in the required amount in an appropriate solvent with one or a combination of ingredients enumerated above, as required, followed by filtered sterilization. Generally, dispersions are prepared by incorporating at least one compound of the invention into a sterile vehicle that contains a basic dispersion medium and any other required ingredient. In the case of sterile powders for the preparation of sterile injectable solutions, exemplary methods of preparation include vacuum drying and freeze-drying, both of which yield a powder of a compound of the invention plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the compound of the invention can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the compounds of the invention are prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the compounds of the invention may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of the compound of the invention calculated to produce the desired therapeutic effect in association with the required pharmaceutical carrier. The specification for the dosage unit forms of the invention are dictated by and directly dependent on the unique characteristics of the compound of the invention and the particular therapeutic effect to be achieved, and the limitations inherent in the art of compounding such an active agent for the treatment of individuals.

Pharmaceutical compositions according to the invention comprising at least one compound of the invention can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as Avicel® PH101 and Avicel® PH102, silicified microcrystalline cellulose (ProSolv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, such as Aerosil® 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet® (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

E. Kits Comprising the Compositions of the Invention

The present invention also encompasses kits comprising the compositions of the invention. Such kits can comprise, for example, (1) at least one compound of the invention; and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial, or similar apparatus for holding and/or mixing the kit components; and (3) delivery apparatus, such as an inhaler, nebulizer, syringe, etc.

F. Methods of Preparing Compounds of the Invention

The compounds of the invention can readily be synthesized using known synthetic methodologies or via a modification of known synthetic methodologies. As would be readily recognized by a skilled artisan, the methodologies described below allow the synthesis of quinolines having a variety of substituents. Exemplary synthetic methods are described in the Examples section below.

If needed, further purification and separation of enantiomers and diastereomers can be achieved by routine procedures known in the art. Thus, for example, the separation of enantiomers of a compound can be achieved by the use of chiral HPLC and related chromatographic techniques. Diastereomers can be similarly separated. In some instances, however, diastereomers can simply be separated physically, such as, for example, by controlled precipitation or crystallization.

The process of the invention, when carried out as prescribed herein, can be conveniently performed at temperatures that are routinely accessible in the art. In one embodiment, the process is performed at a temperature in the range of about 25° C. to about 110° C. In another embodiment, the temperature is in the range of about 40° C. to about 100° C. In yet another embodiment, the temperature is in the range of about 50° C. to about 95° C.

Synthetic steps that require a base are carried out using any convenient organic or inorganic base. Typically, the base is not nucleophilic. Thus, in one embodiment, the base is selected from carbonates, phosphates, hydroxides, alkoxides, salts of disilazanes, and tertiary amines.

The process of the invention, when performed as described herein, can be substantially complete after several minutes to after several hours depending upon the nature and quantity of reactants and reaction temperature. The determination of when the reaction is substantially complete can be conveniently evaluated by ordinary techniques known in the art such as, for example, HPLC, LCMS, TLC, and $^1$H NMR.

G. Methods of Treatment

The invention encompasses methods of preventing or treating (e.g., alleviating one or more symptoms of) medical conditions through use of one or more of the disclosed compounds. The methods comprise administering a therapeutically effective amount of a compound of the invention to a patient in need. The compositions of the invention can also be used for prophylactic therapy.

The compound of the invention used in the methods of treatment according to the invention can be: (1) a novel compound described herein, or a pharmaceutically acceptable salt thereof, a stereoisomer thereof, a prodrug thereof, a metabolite thereof, or an N-oxide thereof; (2) a compound which was known prior to the present invention, but wherein it was not known that the compound is a GSNOR inhibitor, or a pharmaceutically acceptable salt thereof, a stereoisomer thereof, a prodrug thereof, a metabolite thereof, or an N-oxide thereof; or (3) a compound which was known prior to the present invention, and wherein it was known that the compound is a GSNOR inhibitor, but wherein it was not known that the compound is useful for the methods of treatment described herein, or a pharmaceutically acceptable salt, a stereoisomer, a prodrug, a metabolite, or an N-oxide thereof.

The patient can be any animal, domestic, livestock, or wild, including, but not limited to cats, dogs, horses, pigs, and cattle, and preferably human patients. As used herein, the terms patient and subject may be used interchangeably.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition, or disorder. More specifically, "treating" includes reversing, attenuating, alleviating, minimizing, suppressing, or halting at least one deleterious symptom or effect of a disease (disorder) state, disease progression, disease causative agent (e.g., bacteria or viruses), or other abnormal condition. Treatment is continued as long as symptoms and/or pathology ameliorate.

In general, the dosage, i.e., the therapeutically effective amount, ranges from 1 µg/kg to 10 g/kg and often ranges from 10 µg/kg to 1 g/kg or 10 µg/kg to 100 mg/kg body weight of the subject being treated, per day.

H. GSNOR Uses

In subjects with deleteriously high levels of GSNOR or GSNOR activity, modulation may be achieved, for example, by administering one or more of the disclosed compounds that disrupts or down-regulates GSNOR function, or decreases GSNOR levels. These compounds may be administered with other GSNOR inhibitor agents, such as anti-GSNOR antibodies or antibody fragments, GSNOR antisense, iRNA, or small molecules, or other inhibitors, alone or in combination with other agents as described in detail herein.

The present invention provides a method of treating a subject afflicted with a disorder ameliorated by NO donor therapy. Such a method comprises administering to a subject a therapeutically effective amount of a GSNOR inhibitor.

The disorders can include pulmonary disorders associated with hypoxemia and/or smooth muscle constriction in the lungs and airways and/or lung infection and/or lung inflammation and/or lung injury (e.g., pulmonary hypertension, ARDS, asthma, pneumonia, pulmonary fibrosis/interstitial lung diseases, cystic fibrosis, COPD); cardiovascular disease and heart disease (e.g., hypertension, ischemic coronary syndromes, atherosclerosis, heart failure, glaucoma); diseases characterized by angiogenesis (e.g., coronary artery disease); disorders where there is risk of thrombosis occurring; disorders where there is risk of restenosis occurring; inflammatory diseases (e.g., AIDS related dementia, inflammatory bowel disease (IBD), Crohn's disease, colitis, and psoriasis); functional bowel disorders (e.g., irritable bowel syndrome (IBS)); diseases where there is risk of apoptosis occurring (e.g., heart failure, atherosclerosis, degenerative neurologic disorders, arthritis, and liver injury (e.g., drug induced, ischemic or alcoholic)); impotence; sleep apnea; diabetic wound healing; cutaneous infections; treatment of psoriasis; obesity caused by eating in response to craving for food; stroke; reperfusion injury (e.g., traumatic muscle injury in heart or lung or crush injury); and disorders where preconditioning of heart or brain for NO protection against subsequent ischemic events is beneficial, central nervous system (CNS) disorders (e.g., anxiety, depression, psychosis, and schizophrenia); and infections caused by bacteria (e.g., tuberculosis, *C. difficile* infections, among others).

In one embodiment, the disorder is liver injury. Liver injury can include, for example, acute liver toxicity. Acute liver toxicity can result in acute liver failure. Acute liver failure (ALF) is an uncommon but potentially lethal drug-related adverse effect that often leads to liver transplantation (LT) or death. Acetaminophen is the most common cause of acute liver toxicity and acute liver failure, although acute liver toxicity can be clue to other agents, such as alcohol and other drugs. Regardless of whether it occurs as a result of a single overdose or after repeated supratherapeutic ingestion, the progression of acetaminophen poisoning can be categorized into four stages: preclinical toxic effects (a normal serum alanine aminotransferase concentration), hepatic injury (an elevated alanine aminotransferase concentration), hepatic failure (hepatic injury with hepatic encephalopathy), and recovery. As long as sufficient glutathione is present, the liver is protected from injury. Overdoses of acetaminophen (either a single large ingestion or repeated supratherapeutic ingestion) can deplete hepatic glutathione stores and allow liver injury to occur. Compounds of the invention are capable of treating and/or preventing liver injury and/or acute liver toxicity. In this embodiment, appropriate amounts of compounds of the present invention are an amount sufficient to treat and/or prevent liver injury and can be determined without undue experimentation by preclinical and/or clinical trials. In one embodiment, the amount to treat is at least 0.001 mg/kg, at least 0.002 mg/kg, at least 0.003 mg/kg, at least 0.004 mg/kg, at least 0.005 mg/kg, at least 0.006 mg/kg, at least 0.007 mg/kg, at least 0.008 mg/kg, at least 0.009 mg/kg, at least 0.01 mg/kg, at least 0.02 mg/kg, at least 0.03 mg/kg, at least 0.04 mg/kg, at least 0.05 mg/kg, at least at least 0.06 mg/kg, at least 0.07 mg/kg, at least 0.08 mg/kg, at least 0.09 mg/kg, at least 0.1 mg/kg, at least 0.2 mg/kg, at least 0.3 mg/kg, at least 0.4 mg/kg, at least 0.5 mg/kg, at least 0.6 mg/kg, at least 0.7 mg/kg, at least 0.8 mg/kg, at least 0.9 mg/kg, at least 1 mg/kg, at least 1.5 mg/kg, at least 2 mg/kg, at least 2.5 mg/kg, at least 3 mg/kg, at least 3.5 mg/kg, at least 4 mg/kg, at least 4.5 mg/kg, at least 5 mg/kg, at least 6 mg/kg, at least 7 mg/kg, at least 8 mg/kg, at least 9 mg/kg, at least 10 mg/kg, at least 15 mg/kg, at least 20 mg/kg, at least 30 mg/kg, at least 40 mg/kg, at least 50 mg/kg, at least 60 mg/kg, at least 70 mg/kg, at least 80 mg/kg, at least 90 mg/kg, at least 100 mg/kg. The dosing can be hourly, four times, twice, or once daily, or four times, twice, or once per week, or weekly, or every other week, every third week, or monthly.

In one embodiment, the disorder is trauma (including surgery and thermal), infectious, toxic, aging, and ischemic damage to organs of known regenerative capacity, such as skin, gastric mucosa, airway epithelial and cartilaginous structures, liver, neuronal structures such as the spinal cord, bone marrow and bone. We have shown that inhibition of GSNOR by the use of highly specific small molecules treats, repairs, and promotes regeneration of mammalian tissue. By way of example, small molecule inhibitors are effective in treating, and promoting repair and regeneration of mammalian lung tissue damaged by instillation of a chemical agent known to cause severe lung injury (porcine pancreatic elastase) (Blonder et al., ATS 2011 abstract reference). In this embodiment, appropriate amounts of compounds of the present invention are an amount sufficient to regenerate tissue/organs and can be determined without undue experimentation by preclinical and/or clinical trials.

In one embodiment the disorder is trauma (including surgery and thermal), infectious, toxic, aging, and ischemic damage to organs of not commonly known to have regenerative capacity. Examples include regeneration of: the heart, the lung, the kidney, the central nervous system, the peripheral nervous system, peripheral vascular tissue, liver, pancreas, adrenal gland, thyroid, testes, ovary, retina, tongue, bone, bladder, esophagus, larynx, thymus, spleen, cartilaginous structures of the head, and cartilaginous structures of the joints. In this embodiment, appropriate amounts of compounds of the present invention are an amount sufficient to regenerate tissue/organs and can be determined without undue experimentation by preclinical and/or clinical trials.

In one embodiment ex and in vivo implantation and regeneration of organs and structures, including stem cells. In this embodiment, appropriate amounts of compounds of the present invention are an amount sufficient to regenerate tissue/organs and can be determined without undue experimentation by preclinical and/or clinical trials.

In one embodiment, the compounds of the present invention or a pharmaceutically acceptable salt thereof, or a prodrug, stereoisomer, metabolite, or N-oxide thereof, can be administered in combination with an NO donor. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFκB. NO donors including S-nitroso, O-nitroso, C-nitroso, and N-nitroso compounds and nitro derivatives thereof and metal NO complexes, but not excluding other NO bioactivity generating compounds, useful herein are described in "Methods in Nitric Oxide Research," Feelisch et al. eds., pages 71-115 (J. S., John Wiley & Sons, New York, 1996), which is incorporated herein by reference. NO donors which are C-nitroso compounds where nitroso is attached to a tertiary carbon which are useful herein include those described in U.S. Pat. No. 6,359,182 and in WO 02/34705. Examples of S-nitroso compounds, including S-nitrosothiols useful herein, include, for example, S-nitrosoglutathione, S-nitroso-N-acetylpenicillamine, S-nitroso-cysteine and ethyl ester thereof, S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin. Examples of other NO donors useful herein are sodium nitroprusside (nipride), ethyl nitrite, isosorbide, nitroglycerin, SIN 1 which is molsidomine, furoxamines, N-hydroxy (N-nitrosamine), and perfluorocarbons that have been saturated with NO or a hydrophobic NO donor.

The combination of a GSNOR inhibitor with R(+) enantiomer of amlodipine, a known NO releaser (Zhang at al., *J. Cardiovasc. Pharm.* 39: 208-214 (2002)) is also an embodiment of the present invention.

The present invention also provides a method of treating a subject afflicted with pathologically proliferating cells where the method comprises administering to said subject a therapeutically effective amount of an inhibitor of GSNOR. The inhibitors of GSNOR are the compounds as defined above, or a pharmaceutically acceptable salt thereof, or a stereoisomer, prodrug, metabolite, or N-oxide thereof, in combination with a pharmaceutically acceptable carrier. Treatment is continued as long as symptoms and/or pathology ameliorate.

In another embodiment, the pathologically proliferating cells can be pathologically proliferating microbes. The microbes involved can be those where GSNOR is expressed to protect the microbe from nitrosative stress or where a host cell infected with the microbe expresses the enzyme, thereby protecting the microbe from nitrosative stress. The term "pathologically proliferating microbes" is used herein to mean pathologic microorganisms including, but not limited to, pathologic bacteria, pathologic viruses, pathologic Chlamydia, pathologic protozoa, pathologic Rickettsia, pathologic fungi, and pathologic mycoplasmata. More detail on the applicable microbes is set forth at columns 11 and 12 of U.S. Pat. No. 6,057,367. The term "host cells infected with pathologic microbes" includes not only mammalian cells infected with pathologic viruses but also mammalian cells containing intracellular bacteria or protozoa, e.g., macrophages containing *Mycobacterium tuberculosis, Mycobacterium leper* (leprosy), or *Salmonella typhi* (typhoid fever).

In another embodiment, the pathologically proliferating cells can be pathologic helminths. The term "pathologic helminths" is used herein to refer to pathologic nematodes, pathologic trematodes and pathologic cestodes. More detail on the applicable helminths is set forth at column 12 of U.S. Pat. No. 6,057,367.

In another embodiment, the pathologically proliferating cells can be pathologically proliferating mammalian cells. The term "pathologically proliferating mammalian cells" as used herein means cells of the mammal that grow in size or number in said mammal so as to cause a deleterious effect in the mammal or its organs. The term includes, for example, the pathologically proliferating or enlarging cells causing restenosis, the pathologically proliferating or enlarging cells causing benign prostatic hypertrophy, the pathologically proliferating cells causing myocardial hypertrophy, and proliferating cells at inflammatory sites such as synovial cells in arthritis or cells associated with a cell proliferation disorder.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration. The cell proliferative disorder can be a precancerous condition or cancer. The cancer can be primary cancer or metastatic cancer, or both.

As used herein, the term "cancer" includes solid tumors, such as lung, breast, colon, ovarian, pancreas, prostate, adenocarcinoma, squamous carcinoma, sarcoma, malignant glioma, leiomyosarcoma, hepatoma, head and neck cancer, malignant melanoma, non-melanoma skin cancers, as well as hematologic tumors and/or malignancies, such as leukemia, childhood leukemia and lymphomas, multiple myeloma, Hodgkin's disease, lymphomas of lymphocytic and cutaneous origin, acute and chronic leukemia such as acute lymphoblastic, acute myelocytic, or chronic myelocytic leukemia, plasma cell neoplasm, lymphoid neoplasm, and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses, and the like. In one embodiment, proliferative diseases include dysplasias and disorders of the like.

In one embodiment, treating cancer comprises a reduction in tumor size, decrease in tumor number, a delay of tumor growth, decrease in metastatic lesions in other tissues or organs distant from the primary tumor site, an improvement in the survival of patients, or an improvement in the quality of patient life, or at least two of the above.

In another embodiment, treating a cell proliferative disorder comprises a reduction in the rate of cellular proliferation, reduction in the proportion of proliferating cells, a decrease in size of an area or zone of cellular proliferation, or a decrease in the number or proportion of cells having an abnormal appearance or morphology, or at least two of the above.

In yet another embodiment, the compounds of the present invention or a pharmaceutically acceptable salt thereof, a stereoisomer thereof, a prodrug thereof, a metabolite thereof, or an N-oxide thereof can be administered in combination with a second chemotherapeutic agent. In a further embodiment, the second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, araC, 5-fluorouracil, methotrexate, docetaxel, goserelin, vincristin, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

In one embodiment, the compounds of the present invention or a pharmaceutically acceptable salt thereof, a stereoisomer thereof, a prodrug thereof, a metabolite thereof, or an N-oxide thereof, can be administered in combination with an agent that imposes nitrosative or oxidative stress. Agents for selectively imposing nitrosative stress to inhibit proliferation of pathologically proliferating cells in combination therapy with GSNOR inhibitors herein and dosages and routes of administration therefor include those disclosed in U.S. Pat. No. 6,057,367, which is incorporated herein. Supplemental agents for imposing oxidative stress (i.e., agents that increase GSSG (oxidized glutathione) over GSH (glutathione) ratio or NAD(P) over NAD(P)H ratio or increase thiobarbituric acid derivatives) in combination therapy with GSNOR inhibitors herein include, for example, L-buthionine-S-sulfoximine (BSO), glutathione reductase inhibitors (e.g., BCNU), inhibitors or uncouplers of mitochondrial respiration, and drugs that increase reactive oxygen species (ROS), e.g., adriamycin, in standard dosages with standard routes of administration.

GSNOR inhibitors may also be co-administered with a phosphodiesterase inhibitor (e.g., rolipram, cilomilast, roflumilast, Viagra® (sildenifil citrate), Cialis® (tadalafil), Levitra® (vardenifil), etc.), a β-agonist, a steroid, an antimuscarinics, or a leukotriene antagonist (LTD-4). Those skilled in the art can readily determine the appropriate therapeutically effective amount depending on the disorder to be ameliorated.

GSNOR inhibitors may be used as a means to improve β-adrenergic signaling. In particular, inhibitors of GSNOR alone or in combination with β-agonists could be used to treat or protect against heart failure, or other vascular disorders such as hypertension and asthma. GSNOR inhibitors can also be used to modulate G protein coupled receptors (GPCRs) by potentiating Gs G-protein, leading to smooth muscle relaxation (e.g., airway and blood vessels), and by attenuating Gq G-protein, and thereby preventing smooth muscle contraction (e.g., in airway and blood vessels).

The therapeutically effective amount for the treatment of a subject afflicted with a disorder ameliorated by NO donor therapy is the GSNOR inhibiting amount in vivo that causes amelioration of the disorder being treated or protects against a risk associated with the disorder. For example, for asthma, a therapeutically effective amount is a bronchodilating effective amount; for cystic fibrosis, a therapeutically effective amount is an airway obstruction ameliorating effective amount; for ARDS, a therapeutically effective amount is a hypoxemia ameliorating effective amount; for heart disease, a therapeutically effective amount is an angina relieving or angiogenesis inducing effective amount; for hypertension, a therapeutically effective amount is a blood pressure reducing effective amount; for ischemic coronary disorders, a therapeutic amount is a blood flow increasing effective amount; for atherosclerosis, a therapeutically effective amount is an endothelial dysfunction reversing effective amount; for glaucoma, a therapeutic amount is an intraocular pressure reducing effective amount; for diseases characterized by angiogenesis, a therapeutically effective amount is an angiogenesis inhibiting effective amount; for disorders where there is risk of thrombosis occurring, a therapeutically effective amount is a thrombosis preventing effective amount; for disorders where there is risk of restenosis occurring, a therapeutically effective amount is a restenosis inhibiting effective amount; for chronic inflammatory diseases, a therapeutically effective amount is an inflammation reducing effective amount; for disorders where there is risk of apoptosis occurring, a therapeutically effective amount is an apoptosis preventing effective amount; for impotence, a therapeutically effective amount is an erection attaining or sustaining effective amount; for obesity, a therapeutically effective amount is a satiety causing effective amount; for stroke, a therapeutically effective amount is a blood flow increasing or a TIA protecting effective amount; for reperfusion injury, a therapeutically effective amount is a function increasing effective amount; and for preconditioning of heart and brain, a therapeutically effective amount is a cell protective effective amount, e.g., as measured by troponin or CPK.

The therapeutically effective amount for the treatment of a subject afflicted with pathologically proliferating cells means a GSNOR inhibiting amount in vivo which is an antiproliferative effective amount. Such antiproliferative effective amount as used herein means an amount causing reduction in rate of proliferation of at least about 20%, at least about 10%, at least about 5%, or at least about 1%.

I. Uses in an Apparatus

The compounds of the present invention or a pharmaceutically acceptable salt thereof, or a stereoisomer, prodrug, metabolite, or N-oxide thereof, can be applied to various apparatus in circumstances when the presence of such compounds would be beneficial. Such apparatus can be any device or container, for example, implantable devices in which a compound of the invention can be used to coat a surgical mesh or cardiovascular stent prior to implantation in a patient. The compounds of the invention can also be applied to various apparatus for in vitro assay purposes or for culturing cells.

The compounds of the present invention or a pharmaceutically acceptable salt thereof, or a stereoisomer, a prodrug, a metabolite, or an N-oxide thereof, can also be used as an agent for the development, isolation or purification of binding partners to compounds of the invention, such as antibodies, natural ligands, and the like. Those skilled in the art can readily determine related uses for the compounds of the present invention.

EXAMPLES

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

Example 1-56 list representative novel quinoline analogs of Formula I useful as GSNOR inhibitors of the invention. Exemplary schemes below illustrate some general methods of making the quinoline analogs of Formula I. Synthetic methods that can be used to prepare each compound are described in Examples 1-56. Supporting mass spectrometry data and/or proton NMR data for each compound is also included in Examples 1-56. Synthetic details for corresponding Intermediates are detailed in Example 57.

Schemes 1-5 below illustrate general methods for preparing quinoline analogs.

Scheme 1

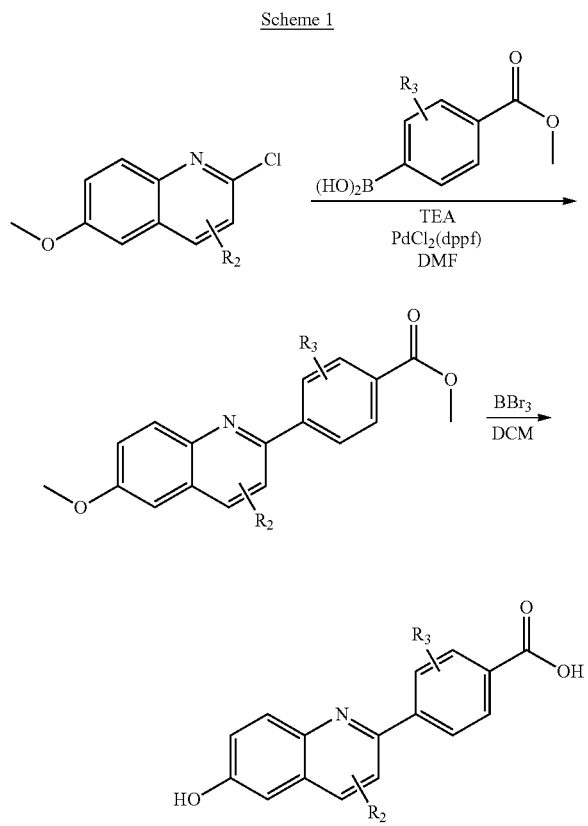

For a detailed example of General Scheme 1 see Compound 1 in Example 1.

Scheme 2

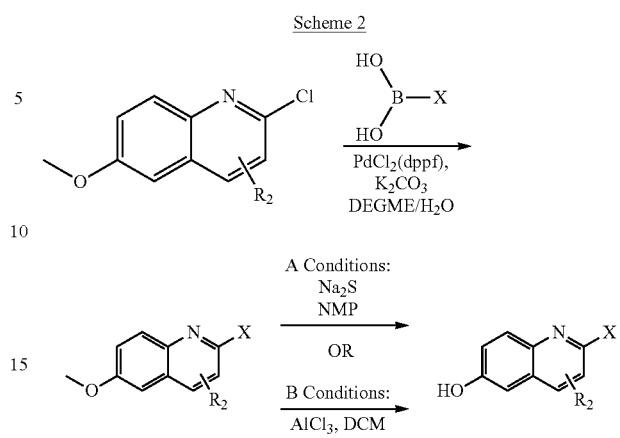

For a detailed example of Scheme 2, A conditions, see Compound 2 in Example 2.

For a detailed example of Scheme 2, B conditions, see Compound 8 in Example 8.

Scheme 3

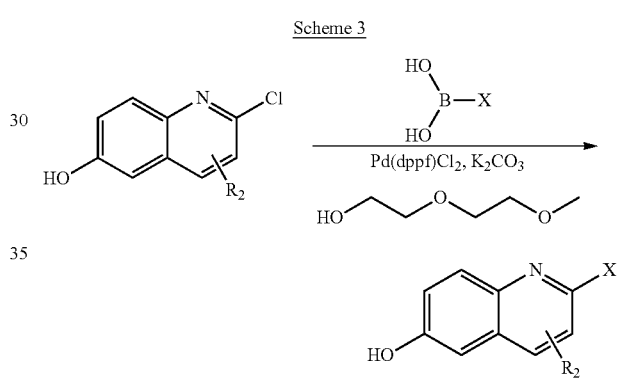

For a detailed example of Scheme 3, see Compound 9 in Example 9.

Scheme 4

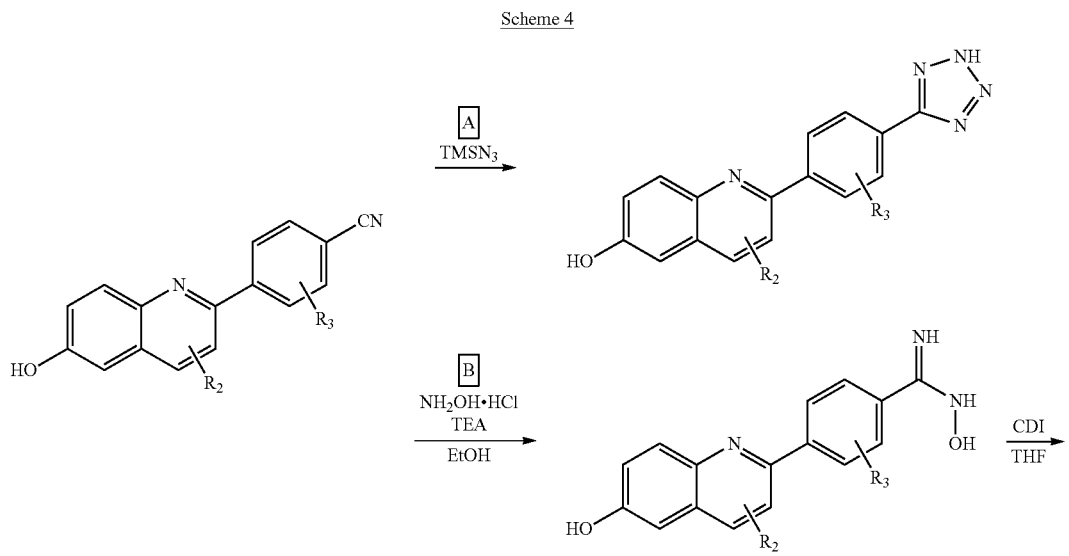

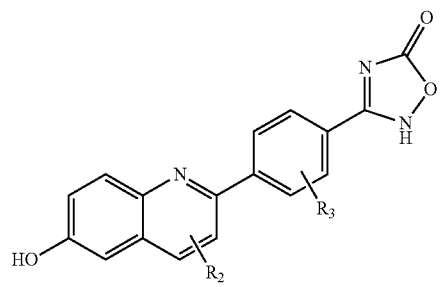
For a detailed example of Scheme 4, Route A, see Compound 11 in Example 11.
For a detailed example of Scheme 4, Route B, see Compound 12 in Example 12.

Scheme 5
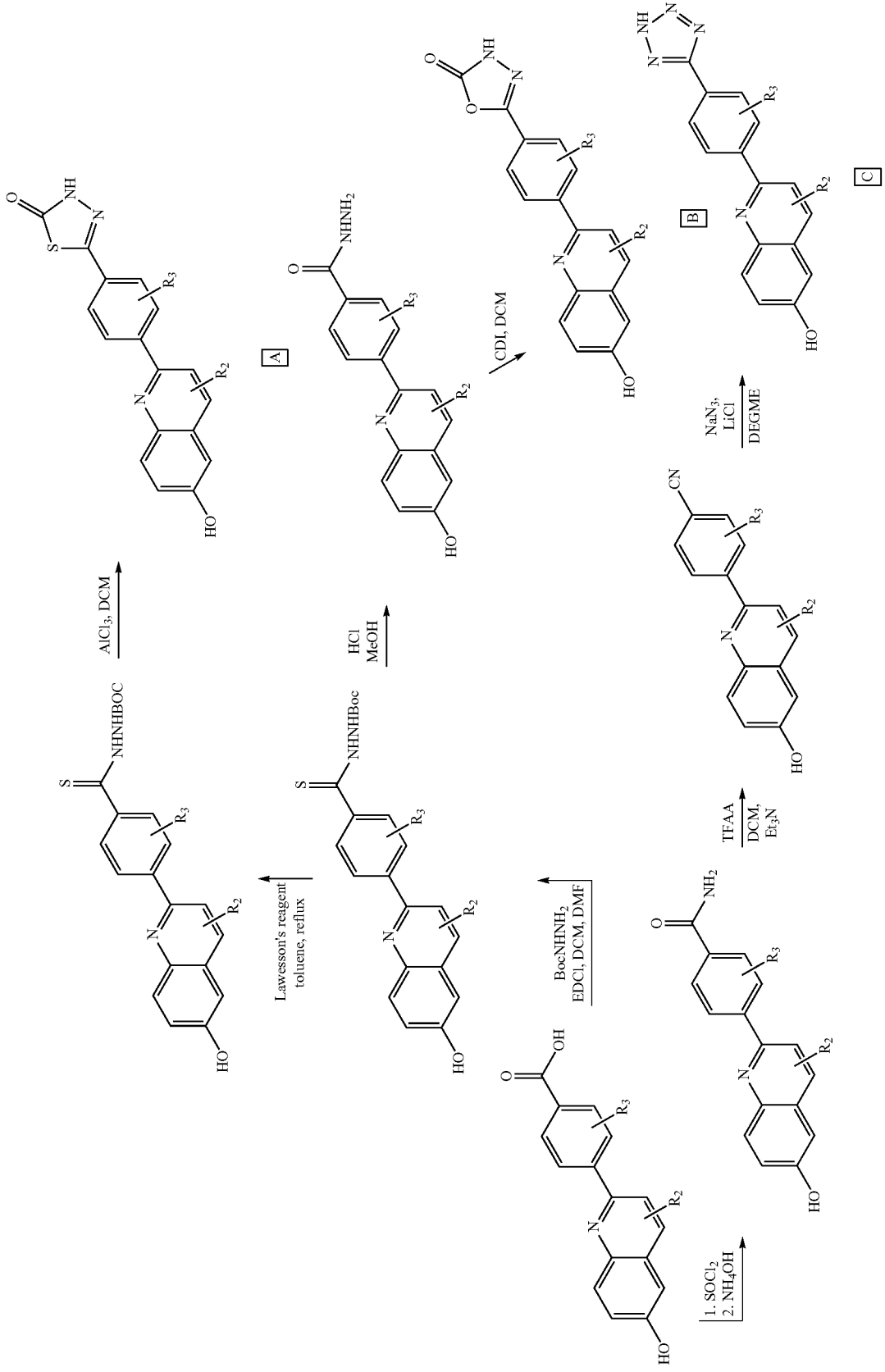

Example 1: Compound 1: 4-(6-hydroxy-3-methylquinolin-2-yl)benzoic acid

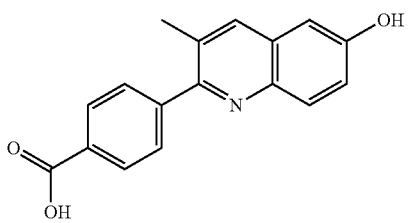 [SMILES: Cc1cc2cc(O)ccc2nc1-c1ccc(C(=O)O)cc1]

Followed Scheme 1

Step 1: Synthesis of Methyl 4-(6-methoxy-3-methylquinolin-2-yl)benzoate

To a mixture of 2-chloro-6-methoxy-3-methylquinoline (100 mg, 0.482 mmol), 4-(methoxycarbonyl)phenylboronic acid (184 mg, 1.02 mmol), TEA (0.35 mL, 2.41 mmol), and $PdCl_2(dppf)$ (35 mg, 0.048 mmol) was added 2 mL of DMF under argon. The mixture was then stirred for 2.5 h at 120° C. in a microwave reactor. The crude mixture was then diluted with water (25 mL) and extracted with EtOAc (25 mL×2). The organics were washed with brine (50 mL), dried over sodium sulfate, and concentrated to yield 250 mg of crude material. The crude was purified via column chromatography with a gradient of 5% EtOAc in hexanes to 80% EtOAc in hexanes to yield 37 mg (25% yield) of methyl 4-(6-methoxy-3-methylquinolin-2-yl)benzoate.

Step 2: Synthesis of 4-(6-hydroxy-3-methylquinolin-2-yl)benzoic acid

Methyl 4-(6-methoxy-3-methylquinolin-2-yl)benzoate (37 mg, 0.121 mmol) was dissolved in 2 mL of DCM and $BBr_3$ (150 μL) was added. The mixture was stirred at room temperature for 1 day followed by addition of 10 mL of $H_2O$. The solution was stirred vigorously for 1 h followed by filtration of the solids. The solids were washed with $H_2O$ and dried in vacuo to yield 9.5 mg (28% yield) of Compound 1. $^1$H NMR (DMSO-$d_6$, 400 MHz): δ 8.37 (s, 1H), 8.10 (d, 2H), 7.94 (d, 1H), 7.78 (d, 2H), 7.42-7.39 (dd, 1H), 7.24-7.23 (d, 1H), 2.43 (s, 3H). MS (ESI): m/z 280.10 [M+H]$^+$.

Example 2: Compound 2: 2-(4-(1H-tetrazol-5-yl)phenyl)-3-methylquinolin-6-ol

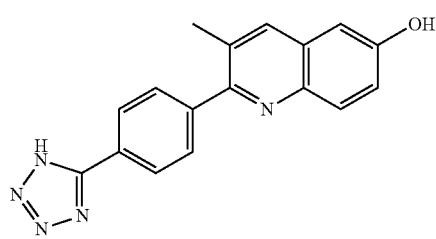 [SMILES: Cc1cc2cc(O)ccc2nc1-c1ccc(-c2nnn[nH]2)cc1]

Followed Scheme 2: A conditions

Step 1: Synthesis of 2-(4-(1H-tetrazol-5-yl)phenyl)-6-methoxy-3-methylquinoline To a mixture of 2-chloro-6-methoxy-3-methylquinoline (100 mg, 0.482 mmol), 4-(1H-tetrazol-5-yl)phenylboronic acid (91.2 mg, 0.482 mmol), $K_2CO_3$ (199 mg, 1.45 mmol), and $PdCl_2(dppf)$ (17.6 mg, 0.024 mmol) was added 7 mL of DEGME and 3 mL of $H_2O$ under argon. The mixture was stirred at 150° C. in a microwave reactor for 1.5 hours. The crude mixture was diluted with 1N NaOH (10 mL) and slowly acidified to a pH of 4.0 using conc. HCl. The solids were filtered to yield 128 mg (84% yield) of desired product.

Step 2: Synthesis of (2-(4-(1H-tetrazol-5-yl)phenyl)-3-methylquinolin-6-ol)

2-(4-(1H-tetrazol-5-yl)phenyl)-6-methoxy-3-methylquinoline (128 mg, 0.40 mmol) was dissolved in 5 mL of NMP and $Na_2S$ (47 mg, 0.60 mmol) was added to it. The mixture was then stirred for 4 hours at 140° C. in a microwave reactor. After concentration in vacuo the crude was dissolved in 5 mL of 1N NaOH and slowly acidified with 1N HCl to a pH of 4. The solids were filtered and dried in vacuo to afford 46.2 mg (38% yield) of Compound 2. $^1$H NMR (DMSO-$d_6$, 400 MHz): δ 10.10-10.00 (bs, 1H), 8.18-8.15 (d, 2H), 8.08 (s, 1H), 7.87-7.84 (m, 3H), 7.30-7.26 (d, 1H), 7.13 (s, 1H), 2.45 (s, 3H). MS (ESI): m/z 304.11 [M+H]$^+$.

Example 3: Compound 3: 4-(6-hydroxyquinolin-2-yl)benzoic acid

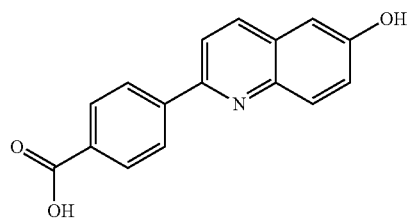 [SMILES: O=C(O)c1ccc(-c2ccc3cc(O)ccc3n2)cc1]

Followed Scheme 2, A conditions: Starting materials: 2-chloro-6-methoxyquinoline (Intermediate 1) (100 mg, 0.52 mmol) and (4-(methoxycarbonyl)phenyl) boronic acid. $^1$H NMR (DMSO-$d_6$, 400 MHz): δ 13.06-12.90 (bs, 1H), 10.14 (s, 1H), 8.36-8.33 (d, 2H), 8.30-8.27 (d, 1H), 8.11-8.06 (m, 3H), 7.97-7.94 (d, 1H), 7.38-7.34 (dd, 1H), 7.20 (s, 1H). MS (ESI): m/z 266.08 [M+H]$^+$.

Example 4: Compound 4: 2-(4-(1H-tetrazol-5-yl)phenyl)quinolin-6-ol

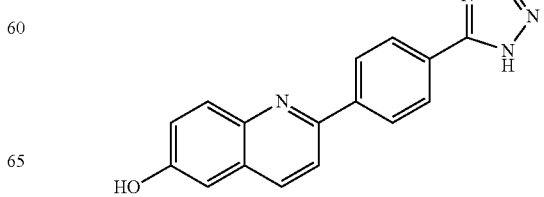

Followed Scheme 2, A conditions: Starting materials: 2-chloro-6-methoxyquinoline (Intermediate 1) and (4-(1H-tetrazol-5-yl)phenyl)boronic acid. $^1$H NMR (DMSO-$d_6$, 400 MHz): δ 10.15 (s, 1H), 8.45 (d, 2H), 8.31-8.28 (d, 1H), 8.22-8.12 (m, 3H), 7.98-7.95 (d, 1H), 7.39-7.35 (dd, 1H), 7.21 (s, 1H). MS (ESI): m/z 290.08 [M+H]$^+$.

Example 5: Compound 5: 1-(6-hydroxyquinolin-2-yl)piperidine-4-carboxylic acid

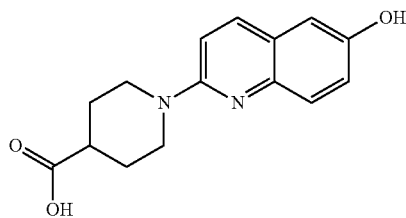 [SMILES: O=C(O)C1CCN(c2ccc3cc(O)ccc3n2)CC1]

Step 1: Synthesis of ethyl 4-(6-methoxyquinolin-2-yl)cyclohexane carboxylate Ethyl piperidine-4-carboxylate (100 mg) was treated with 2-chloro-6-methoxyquinoline (Intermediate 1) (90 mg) in MeCN (0.8 mL) and TEA (100 mg) in a sealed tube at 180° C. for 6 h in a microwave reactor. After aqueous work-up with EtOAc and column purification, eluting with EtOAc/hexane, ethyl 4-(6-methoxyquinolin-2-yl)cyclohexanecarboxylate (90 mg) was afforded as a solid.

Step 2: Synthesis of Compound 5

Ethyl 4-(6-methoxyquinolin-2-yl)cyclohexanecarboxylate (90 mg) was treated with sodium ethanethiolate (150 mg) in NMP (2 mL) at 100° C. over 48 h. The desired product (50 mg) was purified by a Dowex 50W X8 cation exchange column, eluting with water and 2N NH$_4$OH solution. $^1$H NMR (DMSO-$d_6$, 300 MHz): δ 7.82 (1H, d, J=9 Hz), 7.42 (1H, d, J=9 hz), 7.13 (1H, d, J=9 Hz), 7.08 (1H, dd, J=3, 9 Hz), 6.93 (1H, d, J=3 Hz), 4.2-4.4 (2H, m), 2.88-2.97 (2H, m), 2.15-2.21 (1H, m), 1.80-1.86 (2H, m), 1.45-1.60 (1H, m) ppm. MS (ESI): m/z 273.0 [M+1]$^+$.

Example 6: Compound 6: (1r,4r)-4-(6-hydroxyquinolin-2-yl)cyclohexanecarboxylic acid

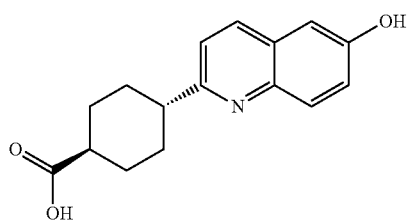 [SMILES: O=C(O)[C@H]1CC[C@H](c2ccc3cc(O)ccc3n2)CC1]

Step 1: Synthesis of (1r,4r)-methyl 4-(6-methoxyquinolin-2-yl)cyclohexanecarboxylate and (1s,4s)-methyl 4-(6-methoxyquinolin-2-yl)cyclohexanecarboxylate Methyl 4-(6-hydroxyquinolin-2-yl)cyclohex-3-enecarboxylate (261 mg) (Compound 16) was dissolved in EtOAc (10 mL) and mixed with 10% Pd/C (38.5 mg). The system was vacuumed shortly and charged with hydrogen. This procedure was repeated three times. The reaction mixture was stirred under hydrogen for 3 h. After filtration to remove the catalyst and concentration under reduced pressure, the resultant mixtures were separated by flash silica gel chromatography eluting with EtOAc/hexane to afford (1s,4s)-methyl 4-(6-methoxyquinolin-2-yl)cyclohexanecarboxylate (153 mg) and (1r,4r)-methyl 4-(6-methoxyquinolin-2-yl)cyclohexanecarboxylate (72 mg) separately.

Step 2: Synthesis of Compound 6

Followed the procedure described in Step 2 of Example 5, starting from (1r,4r)-methyl 4-(6-methoxyquinolin-2-yl)cyclohexanecarboxylate (72 mg, above product) to give the desired Compound 6. $^1$H NMR (DMSO-$d_6$, 300 MHz): δ 8.03 (1H, d, J=9 Hz), 7.75 (1H, d, J=9 hz), 7.33 (1H, d, J=9 Hz), 7.24 (1H, dd, J=3, 9 Hz), 7.08 (1H, d, J=3 Hz), 3.30 (1H, m), 2.76 (1H, m), 2.25-1.90 (4H, m) 1.75-1.50 (4H, m) ppm. MS (ESI): m/z 272.0 [M+1]$^+$.

Example 7: Compound 7: (1s,4s)-4-(6-hydroxyquinolin-2-yl)cyclohexanecarboxylic acid

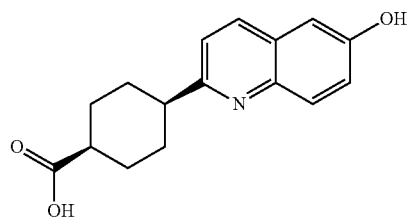 [SMILES: O=C(O)[C@H]1CC[C@@H](c2ccc3cc(O)ccc3n2)CC1]

Followed the procedure described in Step 2 of Example 5, starting from (1s,4s)-methyl 4-(6-methoxyquinolin-2-yl)cyclohexanecarboxylate (72 mg, see Example 6 Step 1 for synthesis) to give the desired Compound 7. $^1$H NMR (DMSO-$d_6$, 300 MHz): δ 7.97 (1H, d, J=9 Hz), 7.74 (1H, d, J=9 hz), 7.26 (1H, dd, J=3, 9 Hz), 7.24 (1H, d, J=9 Hz), 7.08 (1H, d, J=3 Hz), 3.34 (1H, m), 2.75 (1H, m), 2.25-1.50 (8H, m) ppm. MS (ESI): m/z 272.0 [M+1]$^+$.

Example 8: Compound 8: 3-chloro-4-(6-hydroxyquinolin-2-yl)benzoic acid

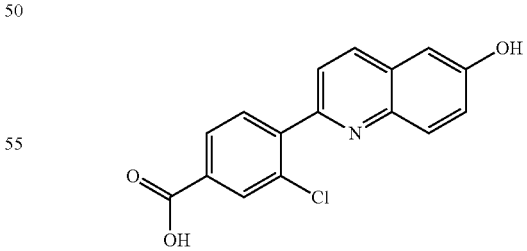

Followed Scheme 2, B conditions:

Step 1: Synthesis of 3-chloro-4-(6-methoxyquinolin-2-yl)benzoic acid

A mixture of 2-chloro-6-methoxyquinoline (Intermediate 1) (200 mg, 1.04 mmol), 4-carboxy-2-chlorophenylboronic acid (247 mg, 1.24 mmol) and K$_2$CO$_3$ (369 mg, 2.70 mmol) in DEGME/H$_2$O (7.0 mL/2.0 mL) was degassed three times under N$_2$ atmosphere. Then PdCl$_2$(dppf) (75 mg, 0.104 mmol) was added and the mixture was heated to 110° C. for 3 hours under N$_2$ atmosphere. The reaction mixture was diluted with EtOAc (100 mL) and filtered. The filtrate was washed with brine (20 mL), dried over Na$_2$SO$_4$, filtered and concentrated to give 3-chloro-4-(6-methoxyquinolin-2-yl) benzoic acid (150 mg, yield 46%) as a yellow solid, which was used for the next step without further purification.

Step 2: Synthesis of Compound 8

To a suspension of 3-chloro-4-(6-methoxyquinolin-2-yl) benzoic acid (150 mg, 0.479 mmol) in anhydrous CH$_2$Cl$_2$ (5 mL) was added AlCl$_3$ (320 mg, 2.40 mmol). The reaction mixture was refluxed overnight. The mixture was quenched with saturated NH$_4$Cl (10 mL) and the aqueous layer was extracted with CH$_2$Cl$_2$/MeOH (v/v=10:1, 30 mL×3). The combined organic layer was washed with brine, dried over Na$_2$SO$_4$, filtered, and concentrated to give the crude product, which was purified by prep-HPLC (0.1% TFA as additive) to give 3-chloro-4-(6-hydroxyquinolin-2-yl)benzoic acid (25 mg, yield 18%). $^1$H NMR (DMSO, 400 MHz): δ 10.20 (brs, 1H), 8.30 (d, J=8.4 Hz, 1H), 8.10-8.00 (m, 2H), 7.95 (d, J=9.2 Hz, 1H), 7.80 (d, J=8.0 Hz, 1H), 7.72 (d, J=8.8 Hz, 1H), 7.38 (dd, J=6.4, 2.8 Hz, 1H), 7.22 (d, J=2.4 Hz, 1H), MS (ESI): m/z 299.9 [M+H]$^+$.

Example 9: Compound 9:
2-chloro-4-(6-hydroxyquinolin-2-yl)benzoic acid

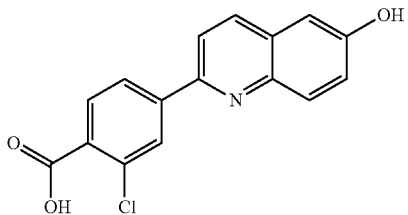 [SMILES: O=C(O)c1ccc(-c2ccc3cc(O)ccc3n2)cc1F]

Followed Scheme 3:

A mixture of 2-chloroquinolin-6-ol (Intermediate 2) (50 mg, 0.270 mmol), 4-borono-2-chlorobenzoic acid (55 mg, 0.270 mmol), K$_2$CO$_3$ (75 mg, 0.540 mmol) and Pd(dppf)Cl$_2$ (25 mg, 0.0306 mmol) in 2-(2-methoxyethoxy)ethanol (1.5 mL) and water (0.4 mL) was stirred under N$_2$ atmosphere at 130° C. for 3 hours. The resulting mixture was cooled to room temperature and filtered. The filtrate was concentrated under reduced pressure and the residue was purified by prep. HPLC (0.1% TFA as additive) to give Compound 9 (33 mg, yield 40%) as yellow solid. $^1$H NMR (CD$_3$OD, 400 MHz): δ 8.39 (d, J=8.4 Hz, 1H), 8.29 (d, J=1.6 Hz, 1H), 8.16-8.02 (m, 4H), 7.47 (dd, J=9.2, 2.8 Hz, 1H), 7.25 (d, J=2.4 Hz, 1H). MS (ESI): m/z 298.0 [M−1]$^−$.

Example 10: Compound 10:
2-fluoro-4-(6-hydroxyquinolin-2-yl)benzoic acid

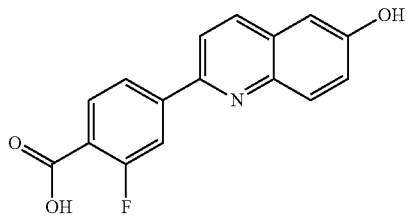

Followed Scheme 3: Starting Materials: 2-chloroquinolin-6-ol (Intermediate 2) and 4-borono-2-fluorobenzoic acid. $^1$H NMR (CD$_3$OD, 400 MHz): δ 8.54 (d, J=8.4 Hz, 1H), 8.20-8.06 (m, 3H), 8.06-7.96 (m, 2H), 7.55 (dd, J=9.2, 2.4 Hz, 1H), 7.32 (d, J=2.8 Hz, 1H). MS (ESI): m/z 283.6 [M+1]$^+$.

Example 11: Compound 11: 2-(4-(2H-tetrazol-5-yl) phenyl)-4-chloroquinolin-6-ol

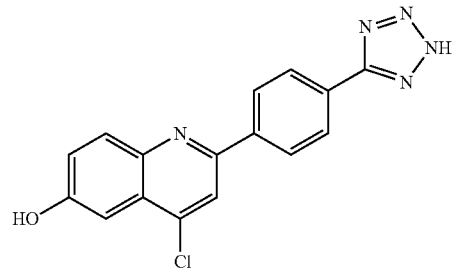 [SMILES: Oc1ccc2nc(-c3ccc(-c4nn[nH]n4)cc3)cc(Cl)c2c1]

Step 1: Synthesis of
4-(4-chloro-6-methoxyquinolin-2-yl)benzonitrile

Followed Scheme 2, Step 1 starting from 4-cyanophenylboronic acid and 2,4-dichloro-6-methoxyquinoline, where the solvent used was DMF, and the catalyst used was Pd(PPh$_3$)$_4$. The mixture was heated to 100° C. for 3 h, allowed to cool, and then poured into ice water. The resulting solid was isolated by filtration, washed with water, and dried followed by recrystallization from methanol to give the desired product.

Step 2: Synthesis of
4-(4-chloro-6-hydroxyquinolin-2-yl)benzonitrile

Followed the procedure for Scheme 1, step 2, with an Ethyl Acetate/aqueous workup. Purification by prep-TLC gave desired product.

Step 3: Synthesis of 2-(4-(2H-tetrazol-5-yl)phenyl)-4-chloroquinolin-6-ol

Followed Scheme 4, route A. To a solution of 4-(4-chloro-6-hydroxyquinolin-2-yl)benzonitrile (65 mg, 0.23 mmol) in toluene (2 mL), was added TMSN$_3$ (455 mg, 4.18 mmol) and Bu$_2$SnO (15 mg, 0.069 mmol) at room temperature. The mixture was heated to reflux overnight. The volatiles were removed under reduced pressure. The residue was purified by prep-HPLC to afford Compound 11 (10 mg, 13.5%). ¹H NMR (MeOD-d₄, 500 MHz): δ 8.34 (d, J=8.5 Hz, 2H), 8.21 (s, 1H), 8.19 (s, 2H), 8.07 (d, J=9.0 Hz, 1H), 7.51 (d, J=2.5 Hz, 1H), 7.47 (dd, J=2.5 Hz, J=9.5 Hz, 1H). MS (ESI): m/z 324.0 [M+1]⁺.

Example 12: Compound 12: 3-(4-(6-hydroxyquinolin-2-yl)phenyl)-1,2,4-oxadiazol-5(2H)-one

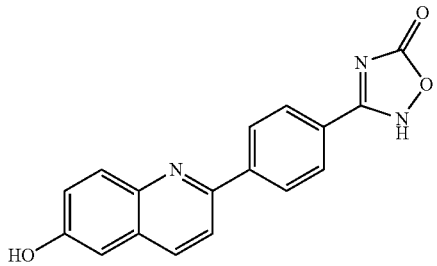

Step 1: Synthesis of 4-(6-hydroxyquinolin-2-yl)benzonitrile

Followed Scheme 3 starting from 2-chloroquinolin-6-ol (Intermediate 2) and 4-cyanophenylboronic acid, and using 1,4-Dioxane:H₂O solution. Reaction was run at 100° C. in a microwave reactor for 1 hour. Ethyl acetate workup was followed by column chromatography (5% to 50% EtOAc in hexanes gradient).

Step 2: Synthesis of N-hydroxy-4-(6-hydroxyquinolin-2-yl)benzimidamide

See Scheme 4, route B. 4-(6-hydroxyquinolin-2-yl)benzonitrile (900 mg, 3.68 mmol) was dissolved in 25 mL of EtOH and to it was added NH₂OH.HCl (500 mg, 7.36 mmol) and TEA (1.5 mL). The mixture was stirred at 80° C. for 2 hours followed by concentration in vacuo. The crude solids were then suspended in 25 mL of H₂O and stirred for 1 hour. Filtration and drying of the solids yielded desired product (800 mg, 78% yield).

Step 3: Synthesis of (3-(4-(6-hydroxyquinolin-2-yl)phenyl)-1,2,4-oxadiazol-5(2H)-one)

N-hydroxy-4-(6-hydroxyquinolin-2-yl)benzimidamide (800 mg, 2.86 mmol) was dissolved in 25 mL of THF and CDI (557 mg, 3.44 mmol) and TEA (0.2 mL) was added. The mixture was stirred at 65° C. for 2 hours, followed by concentration in vacuo. The crude material was dissolved in 10 mL 1N NaOH and filtered through celite. The mixture was then acidified with 1N HCl to a pH of 4.5 and the solids were filtered and dried. The solids were slurried in 10 mL of EtOAc overnight at 50° C. followed by filtration to yield Compound 12 (315 mg, 36% yield). ¹H NMR (DMSO-d₆, 400 MHz): δ 10.19 (s, 1H), 8.42 (d, 2H), 8.28 (d, 1H), 8.14-8.11 (d, 1H), 8.00-7.94 (m, 3H), 7.39-7.35 (dd, 1H), 7.21 (s, 1H). MS (ESI): m/z 306.44 [M+H]⁺.

Example 13: Compound 13: 3-fluoro-4-(6-hydroxyquinolin-2-yl)benzoic acid

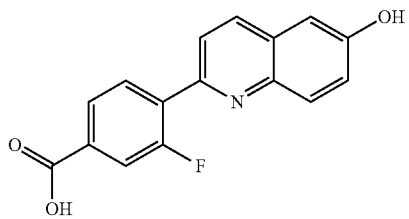 [SMILES: O=C(O)c1ccc(-c2ccc3cc(O)ccc3n2)c(F)c1]

Followed Scheme 3: Starting Materials: 2-chloroquinolin-6-ol and 4-borono-3-fluorobenzoic acid. ¹H NMR (CD₃OD, 400 MHz): δ 8.31 (d, J=8.4 Hz, 1H), 7.94-7.86 (m, 3H), 7.81-7.74 (m, 2H), 7.35 (dd, J=9.2, 2.8 Hz, 1H), 7.15 (d, J=2.8 Hz, 1H). MS (ESI): m/z 283.6 [M+H]⁺.

Example 14: Compound 14: 4-(6-hydroxyquinolin-2-yl)-3-methoxybenzoic acid

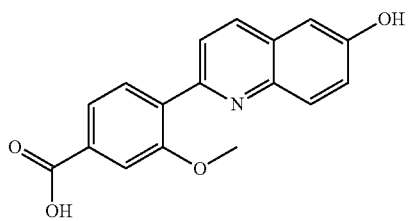 [SMILES: COc1cc(C(=O)O)ccc1-c1ccc2cc(O)ccc2n1]

Followed Scheme 3: Starting Materials: 2-chloroquinolin-6-ol and 4-borono-3-methoxybenzoic acid. ¹H NMR (CD₃OD, 400 MHz): δ 8.81 (d, J=8.4 Hz, 1H), 8.14 (d, J=9.2 Hz, 1H), 8.10 (d, J=8.4 Hz, 1H), 7.89 (dd, J=6.8, 1.6 Hz, 2H), 7.85 (d, J=8.4 Hz, 1H), 7.69 (dd, J=9.2, 2.8 Hz, 1H), 7.48 (d, J=2.8 Hz, 1H). MS (ESI): m/z 295.7 [M+H]⁺.

Example 15: Compound 15: 5-(6-hydroxyquinolin-2-yl)thiophene-2-carboxylic acid

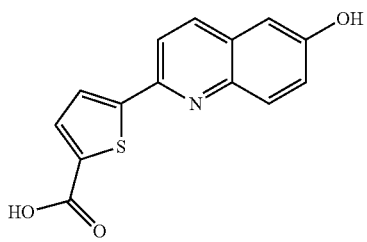 [SMILES: O=C(O)c1ccc(-c2ccc3cc(O)ccc3n2)s1]

Followed Scheme 3: Starting Materials: 2-chloroquinolin-6-ol and 5-boronothiophene-2-carboxylic acid. ¹H NMR (CD₃OD, 400 MHz): δ 8.25 (d, J=8.8 Hz, 1H), 7.97 (dd, J=9.2, 3.2 Hz, 2H), 7.88-7.82 (m, 2H), 7.41 (dd, J=9.2, 2.8 Hz, 1H), 7.19 (d, J=2.4 Hz, 1H). MS (ESI): m/z 271.6 [M+H]⁺.

Example 16: Compound 16: 4-(6-hydroxyquinolin-2-yl)cyclohex-3-enecarboxylic acid

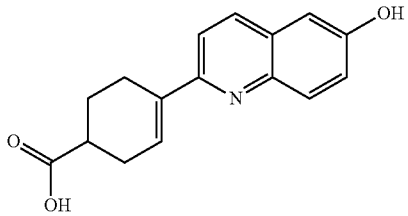 [SMILES: O=C(O)C1CC=C(c2ccc3cc(O)ccc3n2)CC1]

Step 1: Synthesis of methyl 4-(6-hydroxyquinolin-2-yl)cyclohex-3-enecarboxylate

Followed Scheme 3: Starting Materials: 2-chloroquinolin-6-ol and methyl 4-(4,4,5,5-tetramethyl-1,3,2-dioxaborolan-2-yl)cyclohex-3-enecarboxylate.

Step 2: Synthesis of 4-(6-hydroxyquinolin-2-yl)cyclohex-3-enecarboxylic acid

Basic hydrolysis conditions with LiOH gave the final desired product. $^1$H NMR (DMSO-$d_6$, 300 MHz): δ 12.24 (1H, s), 9.92 (1H, s), 8.04 (1H, d, J=9 Hz), 7.75 (1H, d, J=9 hz), 7.66 (1H, d, J=9 Hz), 7.24 (1H, dd, J=3, 9 Hz), 7.08 (1H, d, J=3 Hz), 6.74 (1H, s), 3.30 (1H, m), 2.84 (1H, m), 2.50 (4H, m), 2.08 (1H, m), 1.71 (1H, m) ppm. MS (ESI): m/z 270.0 [M+1]$^+$.

Example 17: Compound 17: 4-(3-fluoro-6-hydroxyquinolin-2-yl)benzoic acid

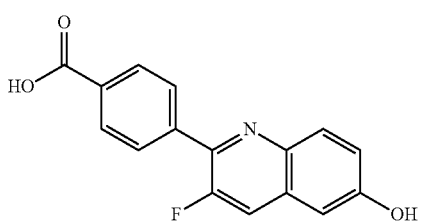

Step 1: Synthesis of 4-(4-chloro-3-fluoro-6-methoxyquinolin-2-yl)benzoic acid

Followed Scheme 3 where the starting materials were 2,4-dichloro-3-fluoro-6-methoxyquinoline (Intermediate 3) and 4-boronobenzoic acid where the crude was purified by silica gel column (PE/EtOAc=1/1) to give a mixture of compound 4-(4-chloro-3-fluoro-6-methoxyquinolin-2-yl)benzoic acid and 4-(3-fluoro-6-methoxyquinolin-2-yl)benzoic acid, which was used for the next step without further purification.

Step 2: Synthesis of 4-(3-fluoro-6-methoxyquinolin-2-yl)benzoic acid

To a solution of the mixture from Step 1 in absolute MeOH (5 mL) was added Pd/C (10% Pd, 100 mg). The mixture was stirred at 25° C. for 1 hour under H$_2$ atmosphere. The solids were filtered off and the filtrate was concentrated to give the product (60 mg, two-step yield 66%).

Step 3: Synthesis of 4-(3-fluoro-6-hydroxyquinolin-2-yl)benzoic acid

Followed Scheme 2, step 2, B conditions. $^1$H NMR (DMSO, 400 MHz): δ 13.35 (brs, 1H), 10.40 (brs, 1H), 8.25 (d, J=12.8 Hz, 1H), 8.27 (s, 4H), 8.01 (d, J=9.2 Hz, 1H), 7.40 (dd, J=8.8, 2.4 Hz, 1H), 7.25 (d, J=2.8 Hz, 1H).

Example 18: Compound 18: 4-(4-chloro-3-fluoro-6-hydroxyquinolin-2-yl)benzoic acid

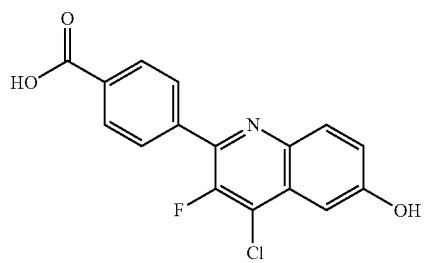 [SMILES: O=C(O)c1ccc(-c2nc3ccc(O)cc3c(Cl)c2F)cc1]

Step 1: Synthesis of 4-(4-chloro-3-fluoro-6-methoxyquinolin-2-yl)benzoic acid

Synthesis described in Step 1 of Example 17.

Step 2: Synthesis of 4-(4-chloro-3-fluoro-6-hydroxyquinolin-2-yl)benzoic acid

Followed Scheme 2, Step 2, B conditions. $^1$H NMR (DMSO, 400 MHz): δ 13.25 (brs, 1H), 10.75 (brs, 1H), 8.10 (s, 4H), 8.05 (d, J=9.2 Hz, 1H), 7.41 (dd, J=9.2, 2.8 Hz, 1H), 7.35 (d, J=2.4 Hz, 1H).

Example 19: Compound 19: 4-(3-chloro-6-hydroxyquinolin-2-yl)benzoic acid

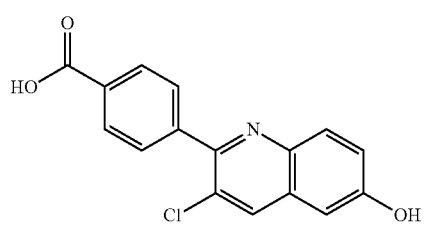 [SMILES: O=C(O)c1ccc(-c2nc3ccc(O)cc3cc2Cl)cc1]

Step 1: Synthesis of 4-(3-chloro-6-methoxyquinolin-2-yl)benzoic acid

Followed Scheme 3 where the starting materials were 2,3-dichloro-6-methoxyquinoline (Intermediate 4) and 4-boronobenzoic acid.

Step 2: Synthesis of 4-(4-chloro-3-fluoro-6-hydroxyquinolin-2-yl)benzoic acid

Followed Scheme 2, Step 2, B conditions. $^1$H NMR (CD$_3$OD, 400 MHz): δ 8.35 (s, 1H), 8.17 (d, J=8.0 Hz, 2H), 7.95 (d, J=9.2 Hz, 1H), 7.80 (d, J=8.0 Hz, 2H), 7.40 (dd, J=9.2, 2.4 Hz, 1H), 7.15 (d, J=2.8 Hz, 1H). MS (ESI): m/z 299.8 [M+H]+.

Example 20: Compound 20: 3-(2-fluoro-4-(6-hydroxyquinolin-2-yl)phenyl)-1,2,4-oxadiazol-5(4H)-one

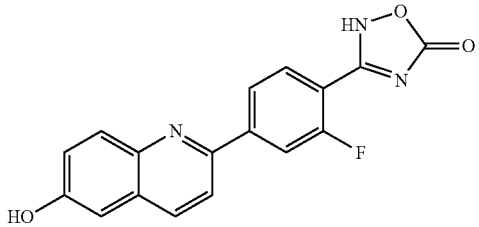 [SMILES: O=c1nc(-c2ccc(-c3ccc4cc(O)ccc4n3)cc2F)[nH]o1]

Step 1: Synthesis of 2-fluoro-4-(6-hydroxyquinolin-2-yl)benzonitrile

Followed Scheme 3 starting from 2-chloroquinolin-6-ol (Intermediate 2) and 4-cyano-3-fluorophenylboronic acid where crude was purified by silica gel column chromatography.

Step 2 and 3: Synthesis of 3-(2-fluoro-4-(6-hydroxyquinolin-2-yl)phenyl)-1,2,4-oxadiazol-5(4H)-one Followed Scheme 4, route B, step 1: After solvent was removed in vacuo, the crude 2-fluoro-N-hydroxy-4-(6-hydroxyquinolin-2-yl)benzimidamide was taken on without purification. Followed Scheme 4, route B, step 2: Purification by silica gel column, eluting with 10% MeOH in DCM gave desired product. $^1$H NMR (DMSO-d$_6$, 300 MHz): δ 10.22 (1H, s), 8.27-8.33 (2H, m), 8.16 (1H, d, J=9 Hz), 7.91-7.99 (2H, m), 7.66 (1H, d, J=9 Hz), 7.39 (1H, dd, J=3, 9 Hz), 7.21 (1H, d, J=3 Hz) ppm. MS (ESI): m/z 324.0 [M+1]+.

Example 21: Compound 21: 3-(3-fluoro-4-(6-hydroxyquinolin-2-yl)phenyl)-1,2,4-oxadiazol-5(4H)-one

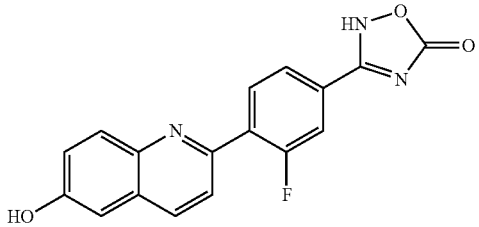 [SMILES: O=c1nc(-c2ccc(-c3ccc4cc(O)ccc4n3)c(F)c2)[nH]o1]

Followed procedure described for Compound 20 in Example 20 starting from 2-chloroquinolin-6-ol (Intermediate 2) and 4-cyano-2-fluorophenylboronic acid. $^1$H NMR (DMSO-d$_6$, 300 MHz): δ 10.22 (1H, s), 8.27-8.33 (2H, m), 7.97 (1H, d, J=9 Hz), 7.77-7.82 (2H, m), 7.39 (1H, dd, J=3, 9 Hz), 7.21 (1H, d, J=3 Hz) ppm. MS (ESI): m/z 324.0 [M+1]+.

Example 22: Compound 22: 4-(4-chloro-6-hydroxyquinolin-2-yl)benzoic acid

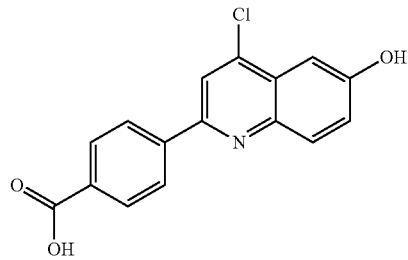

Step 1: Synthesis of 4-(4-chloro-6-hydroxyquinolin-2-yl)benzonitrile

Followed Step 2 of Scheme 1 starting from 4-(4-chloro-6-methoxyquinolin-2-yl)benzonitrile (see step 1 of Example 11 for synthesis).

Step 2: Synthesis of 4-(4-chloro-6-hydroxyquinolin-2-yl)benzoic acid

A solution of 4-(4-chloro-6-hydroxyquinolin-2-yl)benzonitrile (40 mg, 0.14 mmol), con. HCl (1 mL) and dioxane (1 mL) was heated at 90° C. overnight. The mixture was extracted with ethyl acetate. The organic layer was concentrated and purified by prep-HPLC to afford Compound 22 (10 mg, yield: 23%). $^1$H NMR (MeOD-d$_4$, 500 MHz): 8.16 (d, J=8.0 Hz, 2H), 8.10 (d, J=8.5 Hz, 2H), 8.07 (s, 1H), 7.96 (d, J=9.0 Hz, 1H), 7.41 (d, J=2.5 Hz, 1H), 7.35 (dd, J=3.0 Hz, J=9.0 Hz, 1H). MS (ESI): m/z 300 [M+1]+.

Example 23: Compound 23: 2-(2-chloro-4-(2H-tetrazol-5-yl)phenyl)quinolin-6-ol

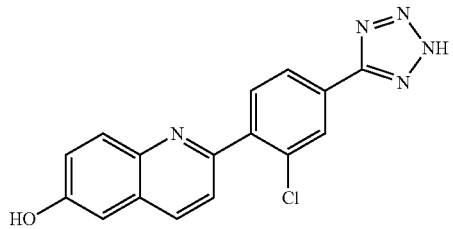 [SMILES: Oc1ccc2nc(-c3ccc(-c4nn[nH]n4)cc3Cl)ccc2c1]

Example procedure for Scheme 5, Compound C.

Step 1: Synthesis of 3-chloro-4-(6-hydroxyquinolin-2-yl)benzamide

A mixture of 3-chloro-4-(6-hydroxyquinolin-2-yl)benzoic acid (Compound 8, Example 8) (400 mg, 1.33 mmol) and SOCl$_2$ (10 mL) was refluxed for 1 hour, then concentrated under reduced pressure to give crude product (400 mg) as off-white solid. To this solid was added NH$_4$OH (10 mL) and the reaction mixture was stirred at 30° C. for 1 hour. The resulting mixture was acidified with aqueous HCl (2 M) until pH=6 and extracted with EtOAc (50 mL×3), dried over Na$_2$SO$_4$ and concentrated to give crude product (360 mg) as a solid.

Step 2: Synthesis of 3-chloro-4-(6-hydroxyquinolin-2-yl)benzonitrile

A mixture of crude 3-chloro-4-(6-hydroxyquinolin-2-yl)benzamide (360 mg), TFAA (505 mg, 2.40 mmol) and Et$_3$N (364 mg, 3.62 mmol) in DCM (20 mL) was stirred at 30° C. overnight. The resulting mixture was suspended in water (50 mL) and extracted with EtOAc (50 mL×3). The combined organic layers were dried over Na$_2$SO$_4$ and concentrated under reduced pressure. The residue was purified by column chromatography on silica gel (PE/EtOAc=10/1) to give the product (250 mg, 3-step yield 67%) as a solid.

Step 3: Synthesis of 2-(2-chloro-4-(2H-tetrazol-5-yl)phenyl)quinolin-6-ol

A mixture of 3-chloro-4-(6-hydroxyquinolin-2-yl)benzonitrile (230 mg, 0.819 mmol), NaN$_3$ (55 mg, 0.820 mmol) and LiCl (70 mg, 1.64 mmol) in diethylene glycol monomethyl ether (5 mL) was refluxed for 4 hours. The resulting mixture was cooled, filtered through silica gel pad and purified by prep-HPLC (0.1% TFA as additive) to give Compound 23 (32 mg, yield 12%). $^1$H NMR (CD$_3$OD, 400 MHz): δ 8.52 (d, J=8.4 Hz, 1H), 8.34 (s, 1H), 8.21 (d, J=8.0 Hz, 1H), 8.04 (d, J=9.2 Hz, 1H), 7.92-7.82 (m, 2H), 7.54 (dd, J=9.2, 2.0 Hz, 1H), 7.34 (d, J=2.0 Hz, 1H). MS (ESI): m/z 323.6 [M+H]$^+$.

Example 24: Compound 24: 5-(4-(6-hydroxyquinolin-2-yl)phenyl)-1,3,4-oxadiazol-2(3H)-one

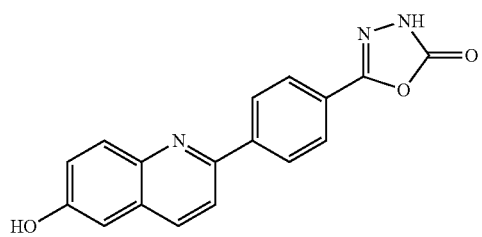 [SMILES: O=c1[nH]nc(-c2ccc(-c3ccc4cc(O)ccc4n3)cc2)o1]

Example procedure for Scheme 5, Compound B.

Step 1: Synthesis of tert-butyl 2-(4-(6-hydroxyquinolin-2-yl)benzoyl)hydrazinecarboxylate A mixture of 4-(6-hydroxyquinolin-2-yl)benzoic acid (Compound 3, Example 3) (200 mg, 0.754 mmol), EDCI (145 mg, 0.754 mmol) and BocNHNH$_2$ (100 mg, 0.754 mmol) in DCM (10 mL) and DMF (10 mL) was stirred at 25° C. overnight, followed by an aqueous/EtOAc workup. The crude was purified by column chromatography on silica gel (PE/EtOAc=1/1) to give the product (200 mg, yield 70%) as a yellow solid.

Step 2: Synthesis of 4-(6-hydroxyquinolin-2-yl)benzohydrazide

A mixture of tert-butyl 2-(4-(6-hydroxyquinolin-2-yl)benzoyl)hydrazinecarboxylate (240 mg, 0.633 mmol) and HCl/MeOH (20 mL, 4M) was stirred at 25° C. overnight. The resulting mixture was concentrated under reduced pressure to dryness to give the product (120 mg, yield 68%).

Step 3: Synthesis of 5-(4-(6-hydroxyquinolin-2-yl)phenyl)-1,3,4-oxadiazol-2(3H)-one A mixture of 4-(6-hydroxyquinolin-2-yl)benzohydrazide (90 mg, 0.322 mmol) and CDI (454 mg, 3.22 mmol) in DCM (20 mL) was refluxed overnight. The resulting mixture was cooled to room temperature, followed by an aqueous/EtOAc workup. The crude was purified by prep-HPLC (0.1% TFA as additive) to give Compound 24 (18 mg, yield 11%). $^1$H NMR (CD$_3$OD, 400 MHz): δ 8.64-8.48 (m, 1H), 8.38-7.96 (m, 6H), 7.66-7.24 (m, 2H). MS (ESI): m/z 305.7 [M+H]$^+$.

Example 25: Compound 25: 3-(dimethylamino)-4-(6-hydroxyquinolin-2-yl)benzoic acid

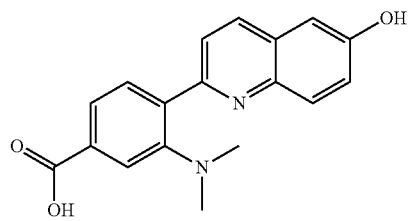 [SMILES: CN(C)c1cc(C(=O)O)ccc1-c1ccc2cc(O)ccc2n1]

Step 1: Synthesis of methyl 3-amino-4-(6-methoxyquinolin-2-yl)benzoate

Followed Scheme 2, step 1, B conditions starting from 2-amino-4-(methoxycarbonyl)phenylboronic acid and 2-chloro-6-methoxyquinoline, with a purification by column chromatography on silica gel (PE/EtOAc=8/1) to give the product.

Step 2: Synthesis of methyl 3-(dimethylamino)-4-(6-methoxyquinolin-2-yl)benzoate To a solution of above compound (400 mg, 1.30 mmol) in MeOH/CH$_2$Cl$_2$ (10 mL/20 mL) was added aqueous HCHO (37% in water, 0.4 mL), followed by NaBH$_3$CN (327 mg, 5.19 mmol) and ZnCl$_2$ (348 mg, 2.60 mmol) at 0° C. The mixture was stirred at 30° C. for 6 hours. The mixture was quenched with ice water, the aqueous layer was extracted with CH$_2$Cl$_2$ (30 mL×3), the combined organic layer was washed with brine (30 mL), dried over anhydrous Na$_2$SO$_4$ and concentrated in vacuo to give the product (400 mg, yield 92%).

Step 3: Synthesis of methyl 3-(dimethylamino)-4-(6-hydroxyquinolin-2-yl)benzoate Followed Scheme 2, step 2, B conditions where crude was purified by column chromatography on silica gel (PE/EtOAc=5/1) to give the desired product.

Step 4: Synthesis of 3-(dimethylamino)-4-(6-hydroxyquinolin-2-yl)benzoic acid To a solution of above compound (290 mg, 0.901 mmol) in THF/MeOH (8 mL/4 mL) was added aqueous LiOH (1 M, 4 mL). The mixture was stirred at 30° C. for 3 hours. The mixture was diluted with H$_2$O (10 mL), the aqueous layer was neutralized by 2M HCl to pH 7. An aqueous/CH$_2$Cl$_2$ workup was followed by column chromatography on silica gel (CH$_2$Cl$_2$/MeOH=10/1) to give Compound 25 (80 mg, yield 29%). ¹H NMR (MeOD-d₄, 400 MHz): δ 8.15 (d, J=8.8 Hz, 1H), 7.95 (d, J=9.2 Hz, 1H), 7.87-7.81 (m, 2H), 7.76 (d, J=8.0 Hz, 1H), 7.60 (d, J=8.0 Hz, 1H), 7.38 (dd, J=8.8, 2.4 Hz, 1H), 7.20 (d, J=2.4 Hz, 1H), 2.65 (s, 6H). MS (ESI): m/z 308.9 [M+H]⁺.

Example 26: Compound 26:
4-(4-fluoro-6-hydroxyquinolin-2-yl)benzoic acid

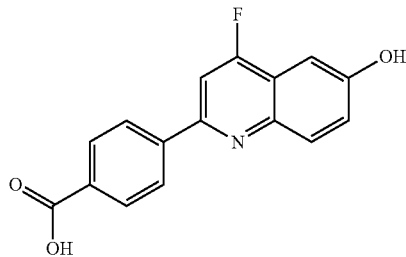 [SMILES: O=C(O)c1ccc(-c2cc(F)c3cc(O)ccc3n2)cc1]

Step 1: Synthesis of
4-(4-fluoro-6-methoxyquinolin-2-yl)benzonitrile

A mixture of 4-(4-chloro-6-methoxyquinolin-2-yl)benzonitrile (Seem Example 11, step 1) (1 g, 3.4 mmol), CsF (5.2 g, 34 mmol), and n-Bu₄NBr (109 mg, 0.34 mmol) in DMSO (10 mL) was heated to 150° C. for 2 h. An aqueous/EtOAC workup was followed by purification by column chromatography (PE/EA=10/1) to afford desired product (300 mg, 31.7%).

Step 2: Synthesis of
4-(4-fluoro-6-hydroxyquinolin-2-yl)benzonitrile

Followed Step 2 of Scheme 1, where an aqueous/EtOAc workup was followed by column chromatography (PE:EA=4:1) to give the desired product.

Step 3: Synthesis of
4-(4-fluoro-6-hydroxyquinolin-2-yl)benzoic acid

A mixture of above (100 mg, 0.38 mmol) and NaOH (152 mg, 3.8 mmol) in 1,4-dioxane/H₂O (1 mL/1 mL) was heated to reflux overnight. The volatiles were removed under reduced pressure. The residue was purified by prep-HPLC and then prep-TLC (EtOAc) to afford Compound 26 (10 mg, 9.3%). ¹H NMR (MeOD-d₄, 500 MHz): 8.22-8.17 (m, 4H), 8.04 (d, J=9.5 Hz, 1H), 7.79 (d, J=12.0 Hz, 1H), 7.43 (dd, J=2.5 Hz, J=9.0 Hz, 1H), 7.31 (d, J=2.0 Hz, 1H). MS (ESI): m/z 284.0 [M+1]⁺.

Example 27: Compound 27:
4-(6-hydroxyquinolin-2-yl)-3-methylbenzoic acid

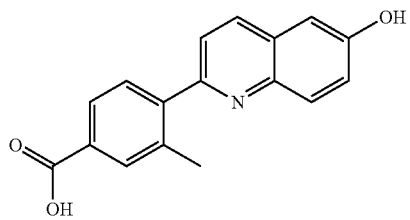 [SMILES: Cc1cc(C(=O)O)ccc1-c1ccc2cc(O)ccc2n1]

Followed Scheme 3: Starting Materials: 2-chloroquinolin-6-ol and methyl 3-methyl-4-(4,4,5,5-tetramethyl-1,3,2-dioxaborolan-2-yl)benzoate. ¹H NMR (DMSO-d₆, 400 MHz): δ 10.45 (brs, 1H), 8.61-8.46 (m, 1H), 8.03 (d, J=8.8 Hz, 1H), 7.96 (s, 1H), 7.92 (d, J=8.0 Hz, 1H), 7.78 (d, J=8.8 Hz, 1H), 7.66 (d, J=8.0 Hz, 1H), 7.50 (d, J=8.0 Hz, 1H), 7.35 (s, 1H), 2.42 (s, 3H). MS (ESI): m/z 279.9 [M+H]⁺.

Example 28: Compound 28: 4-(3-chloro-6-hydroxy-quinolin-2-yl)-3-fluorobenzoic acid

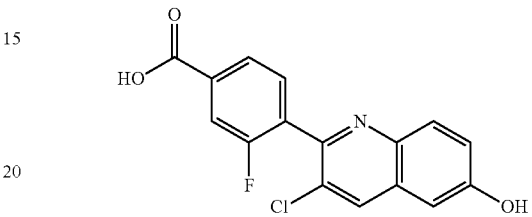

Step 1: Synthesis of 4-(3-chloro-6-methoxyquinolin-2-yl)-3-fluorobenzoic acid

Scheme 3: starting from 2,3-dichloro-6-methoxyquinoline (Intermediate 4) and 4-borono-3-fluorobenzoic acid. An aqueous/EtOAc workup was performed followed by purification by silica gel column (PE/EtOAc=1/1) to give the desired product.

Step 2: Synthesis of 4-(3-chloro-6-hydroxyquinolin-2-yl)-3-fluorobenzoic acid

Scheme 1, step 2: where reaction was refluxed for 18 hours, followed by an aqueous/EtOAc with 10% MeOH workup. Purification by prep-HPLC gave Compound 28. ¹H NMR (DMSO-d₆, 400 MHz): δ 13.45 (brs, 1H), 10.39 (brs, 1H), 8.52 (s, 1H), 7.94-7.88 (m, 2H), 7.80 (d, J=10.4 Hz, 1H), 7.67 (t, J=7.6 Hz, 1H), 7.38 (dd, J=6.8, 2.4 Hz, 1H), 7.21 (d, J=2.8 Hz, 1H). MS (ESI): m/z 317.8 [M+H]⁺.

Example 29: Compound 29: 3-(4-(6-hydroxyquinolin-2-yl)phenyl)-1,2,4-thiadiazol-5(2H)-one

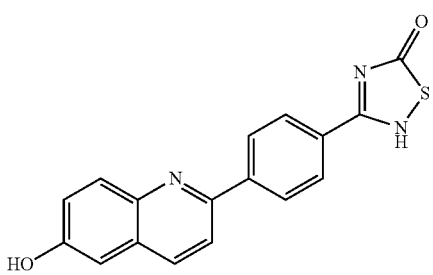

Step 1: Synthesis of
N-hydroxy-4-(6-methoxyquinolin-2-yl)benzimidamide

Scheme 4, route B, step 1: 4-(6-methoxyquinolin-2-yl)benzonitrile (prepared via scheme 3) (780 mg, 3.00 mmol) was suspended in methanol (10 mL) and hydroxylamine hydrochloride (639 mg, 10.7 mmol), K₂CO₃ (414 mg, 3.00 mmol) were added. The reaction mixture was refluxed for 12 hours. Water (15 mL) was added and the precipitated solid was collected by filtration, washed with ethanol (5 mL) and dried over high vacuum to give the product (600 mg).

Step 2: Synthesis of 3-(4-(6-methoxyquinolin-2-yl)phenyl)-1,2,4-thiadiazol-5(2H)-one Scheme 4, route B, step 2: To a solution of above product (450 mg) in THF (10 mL) was added TCDI (410 mg, 2.30 mmol) and the mixture was stirred at 30° C. for 3 hours. After completion of the reaction, the solvent was removed to give the product (300 mg).

Step 3: Synthesis of 3-(4-(6-hydroxyquinolin-2-yl)phenyl)-1,2,4-thiadiazol-5(2H)-one Scheme 1, step 2: Reaction was refluxed overnight, followed by an aqueous/EtOAc workup and purification by prep-HPLC (0.1% TFA as additive) to give Compound 29. $^1$H NMR (DMSO-d₆, 300 MHz): δ 13.50 (brs, 1H), 8.40-8.26 (m, 3H), 8.18-8.04 (m, 3H), 7.95 (d, J=9.0 Hz, 1H), 7.36 (dd, J=9.0, 2.4 Hz, 1H), 7.20 (d, J=2.7 Hz, 1H). MS (ESI): m/z 322.0 [M+H]⁺.

Example 30: Compound 30: 4-(6-hydroxyquinolin-2-yl)-3-(trifluoromethyl)benzoic acid

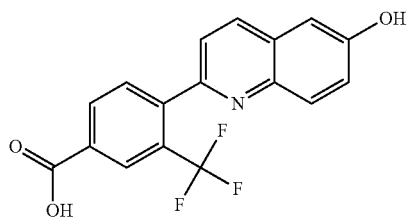 [SMILES: O=C(O)c1ccc(-c2ccc3cc(O)ccc3n2)c(C(F)(F)F)c1]

Followed Scheme 3: starting with 2-chloroquinolin-6-ol and methyl 4-(4,4,5,5-tetramethyl-1,3,2-dioxaborolan-2-yl)-3-(trifluoromethyl)benzoate (Intermediate 5). $^1$H NMR (DMSO-d₆, 400 MHz): δ 10.21 (brs, 1H), 8.35-8.25 (m, 3H), 7.89 (d, J=9.2 Hz, 1H), 7.79 (d, J=8.0 Hz, 1H), 7.57 (d, J=8.4 Hz, 1H), 7.38 (dd, J=9.2, 2.8 Hz, 1H), 7.23 (d, J=2.4 Hz, 1H). MS (ESI): m/z 333.7 [M+H]⁺.

Example 31: Compound 31: 4-(6-hydroxy-3-(trifluoromethyl)quinolin-2-yl)benzoic acid

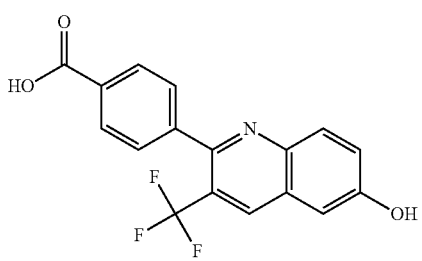 [SMILES: O=C(O)c1ccc(-c2nc3ccc(O)cc3cc2C(F)(F)F)cc1]

Followed Scheme 3: starting with 4-carboxyphenylboronic acid and 2-chloro-3-(trifluoromethyl)quinolin-6-ol (Intermediate 6). $^1$H NMR (DMSO, 400 MHz): δ 13.10 (brs, 1H), 10.45 (brs, 1H), 8.84 (s, 1H), 8.02 (d, J=8.4 Hz, 2H), 7.97 (d, J=8.8 Hz, 1H), 7.60 (d, J=8.0 Hz, 2H), 7.50 (dd, J=9.2, 2.8 Hz, 1H), 7.40 (d, J=2.8 Hz, 1H). MS (ESI): m/z 333.9 [M+H]⁺.

Example 32: Compound 32: 2-(4-carboxyphenyl)-6-hydroxyquinoline 1-oxide

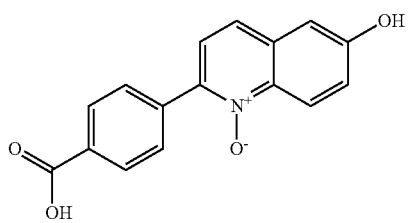 [SMILES: O=C(O)c1ccc(-c2ccc3cc(O)ccc3[n+]2[O-])cc1]

Step 1: Synthesis of methyl 4-(6-hydroxyquinolin-2-yl)benzoate

Scheme 1, step 1, starting from 4-(methoxycarbonyl)phenylboronic acid and 2-chloroquinolin-6-ol, using Na₂CO₃ instead of TEA.

Step 2: Synthesis of 6-hydroxy-2-(4-(methoxycarbonyl)phenyl)quinoline 1-oxide

To a solution of above compound (200 mg, 0.72 mmol) in 1,4-dioxane (5 mL) was added mCPBA (372 mg, 2.16 mmol). The mixture was stirred at room temperature for three days. The volatiles were removed under reduced pressure. The residue was partitioned with sat. Na₂CO₃ solution (10 mL) and EtOAc (20 mL). The organic phase was washed with brine (10 mL), dried over Na₂SO₄, concentrated and purified by column chromatography to afford product (40 mg, 18.9%).

Step 3: Synthesis of 2-(4-carboxyphenyl)-6-hydroxyquinoline 1-oxide

A solution of the above compound (40 mg, 0.14 mmol) and NaOH (16 mg, 0.41 mmol) in 1,4-dioxane/water (1.5 mL/0.5 mL) was heated at 80° C. for 2 h. The volatiles were removed in vacuo. The residue was partitioned with water (8 mL) and EtOAc (10 mL). The aqueous phase was separated, acidified with 1 N HCl to pH=5. The resulting precipitate was filtered, washed with water and EtOH, and dried in vacuo to afford Compound 32 (10 mg, 25.6%). $^1$H NMR (MeOD-d₄, 500 MHz): 8.61 (d, J=9.5 Hz, 1H), 8.20 (d, J=8.0 Hz, 2H), 8.04-7.99 (m, 3H), 7.65 (d, J=8.5 Hz, 1H), 7.48 (dd, J=2.0 Hz, J=9.0 Hz, 1H), 7.30 (d, J=2.0 Hz, 1H); MS (ESI): m/z 282.0 [M+1]⁺.

Example 33: Compound 33: 5-(4-(6-hydroxyquinolin-2-yl)phenyl)-1,3,4-thiadiazol-2(3H)-one

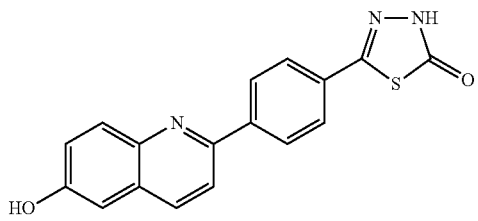 [SMILES: O=c1[nH]nc(-c2ccc(-c3ccc4cc(O)ccc4n3)cc2)s1]

Example procedure for Scheme 5, Compound A:

Step 1: Synthesis of tert-butyl 2-(4-(6-methoxyquinolin-2-yl)benzoyl)hydrazinecarboxylate Scheme 5, step 1 of route A (see Example 24, step 1) starting from 4-(6-methoxyquinolin-2-yl)benzoic acid (prepared following Scheme 3).

Step 2: Synthesis of tert-butyl 2-(4-(6-methoxyquinolin-2-yl)phenylcarbonothioyl) hydrazinecarboxylate A mixture of above compound (2.30 g, 5.85 mmol) and lawesson's reagent (2.30 g, 5.69 mmol) in anhydrous toluene (150 mL) was refluxed overnight. The resulting mixture was concentrated in vacuo. The residue was washed with MeOH and the solid was isolated. The filtrate was concentrated in vacuo and the residue was purified by silica gel column (PE/EtOAc=3/1) to give crude tert-butyl 2-(4-(6-methoxyquinolin-2-yl)phenylcarbonothioyl) hydrazinecarboxylate (2.00 g).

Step 3: Synthesis of 5-(4-(6-hydroxyquinolin-2-yl)phenyl)-1,3,4-thiadiazol-2(3H)-one A mixture of tert-butyl 2-(4-(6-methoxyquinolin-2-yl) phenylcarbonothioyl) hydrazinecarboxylate (500 mg, 1.49 mmol) and AlCl$_3$ (600 mg, 4.50 mmol) in anhydrous DCM (50 mL) was refluxed overnight. Reaction was cooled, followed by an aqueous/EtOAc workup. The residue was purified by prep-HPLC (0.1% TFA as additive) to give Compound 33 (35 mg, yield 7%) as a solid. $^1$H NMR (DMSO-d$_6$, 400 MHz): δ 13.22 (brs, 1H), 10.22 (brs, 1H), 8.40-8.28 (m, 3H), 8.11 (d, J=8.8 Hz, 1H), 7.98 (d, J=8.8 Hz, 1H), 7.86 (d, J=8.4 Hz, 2H), 7.38 (dd, J=9.2, 2.8 Hz, 1H), 7.22 (d, J=2.8 Hz, 1H). MS (ESI): m/z 321.7 [M+H]$^+$.

Example 34: Compound 34: 5-(4-(6-hydroxyquinolin-2-yl)phenyl)-1,2,4-oxadiazol-3(2H)-one

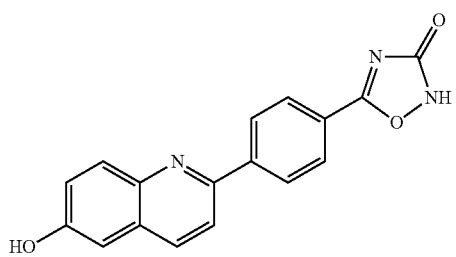

Step 1: Synthesis of 4-(6-methoxyquinolin-2-yl)benzamide

To a suspension of 4-(6-methoxyquinolin-2-yl)benzonitrile (5.00 g, 15.4 mmol, prepared following Scheme 2, Step 1 starting from Intermediate 1 and 4-cyanophenylboronic acid) in DMSO (40 mL) was added aqueous NaOH (1M, 10 mL). The mixture was cooled to 0° C. The aqueous H$_2$O$_2$ (30%, 30 mL) was added dropwise. After addition, the mixture was stirred at 0° C. for 30 minutes. The mixture was quenched with saturated Na$_2$SO$_3$ (100 mL) and filtered. The precipitate was washed with H$_2$O (50 mL) and MeOH (50 mL). The filter cake was dried via high vacuum to give the desired (5.50 g, yield: 99+%) as a solid.

Step 2: Synthesis of 5-(4-(6-methoxyquinolin-2-yl)phenyl)-1,2,4-oxadiazol-3-ol To a suspension of 4-(6-methoxyquinolin-2-yl)benzamide (2.00 g, 7.19 mmol) in DCE (20 mL) was added oxalyl chloride (1.10 g, 8.99 mmol) rapidly at 30° C. The mixture was heated to 70° C. for 16 hours. The solvent was removed in vacuo to give a yellow solid (2.00 g), which was used directly without further purification. A suspension of this material (2.00 g) in TMSN$_3$ (30 mL) was heated to 90° C. for two days. The excess TMSN$_3$ was removed in vacuo and the residue was diluted with EtOH (200 mL). The mixture was filtered off and the filtrate was concentrated to give 5-(4-(6-methoxyquinolin-2-yl)phenyl)-1,2,4-oxadiazol-3-ol (700 mg, two step yield: 30%) as a solid.

Step 3: Synthesis of 5-(4-(6-hydroxyquinolin-2-yl)phenyl)-1,2,4-oxadiazol-3-ol Followed Scheme 2, Step 2, B conditions to give Compound 34 (60 mg, yield: 18%) as a solid. $^1$H NMR (DMSO 400 MHz): δ 12.90 (brs, 1H), 10.15 (brs, 1H), 8.45 (d, J=8.4 Hz, 2H), 8.30 (d, J=8.4 Hz, 1H), 8.15-8.10 (m, 3H), 7.92 (d, J=9.2 Hz, 1H), 7.5 (dd, J=8.8, 2.4 Hz, 1H), 7.20 (d, J=2.8 Hz, 1H). MS (ESI): m/z 305.9 [M+H]$^+$.

Example 35: Compound 35: (1r,4r)-4-(3-chloro-6-hydroxyquinolin-2-yl)cyclohexanecarboxylic acid

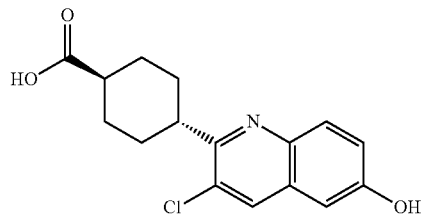 [SMILES: O=C(O)[C@H]1CC[C@H](c2nc3ccc(O)cc3cc2Cl)CC1]

Step 1: Synthesis of ethyl 4-(3-chloro-6-methoxyquinolin-2-yl)cyclohex-3-enecarboxylate Followed Scheme 2, Step 1 (see Ex. 8, Step 1) starting from ethyl 4-(4,4,5,5-tetramethyl-1,3,2-dioxaborolan-2-yl)cyclohex-3-enecarboxylate and 2,3-dichloro-6-methoxyquinoline (Intermediate 4).

Step 2: Synthesis of ethyl 4-(3-chloro-6-methoxyquinolin-2-yl)cyclohexanecarboxylate To ethyl 4-(3-chloro-6-methoxyquinolin-2-yl)cyclohex-3-enecarboxylate (900 mg, 2.60 mmol) in EtOH (40 mL)

was added Rh(PPh$_3$)$_3$Cl (90.0 mg 0.0900 mmol). The mixture was stirred at 30° C. for 4 days under H$_2$ (15 psi). The mixture was filtered off and the filtrate was concentrated to give the crude product, which was purified by silica gel column (PE/EtOAc=10/1) to give the desired product (234 mg, yield 26%).

Step 3: Synthesis of (1r,4r)-4-(3-chloro-6-hydroxyquinolin-2-yl)cyclohexanecarboxylic acid To a mixture of ethyl 4-(3-chloro-6-methoxyquinolin-2-yl)cyclohexanecarboxylate (200 mg, 0.580 mmol) in anhydrous CH$_2$Cl$_2$ (10 mL) was added BBr$_3$ (0.3 mL, 2.9 mmol) dropwise at 0° C. The mixture was stirred at 0° C. for 2 hours. Water (10 mL) was added and the mixture was extracted with EtOAc (30 mL×3). The combined organic layers were washed with brine (20 mL×2), dried over Na$_2$SO$_4$, filtered and concentrated to give the crude product, which was purified by prep-HPLC (0.1% TFA as additive) to give (1r,4r)-4-(3-chloro-6-hydroxyquinolin-2-yl)cyclohexanecarboxylic acid (Compound 35, 65 mg, yield 37%) as a solid, and (1s,4s)-4-(3-chloro-6-hydroxyquinolin-2-yl)cyclohexanecarboxylic acid (Compound 36, 26 mg, yield 15%) as a solid. The structure was confirmed by NOE. Data for Compound 35: $^1$H NMR (DMSO 400 MHz): δ 10.08 (brs, 1H), 8.27 (s, 1H), 7.79 (d, J=8.8 Hz, 1H), 7.26 (dd, J=9.2, 2.8 Hz, 1H), 7.08 (d, J=2.8 Hz, 1H), 3.18 (tt, Jaa=12.0 Hz, Jea=3.2 Hz, 1H), 2.28 (tt, Jaa=12.0 Hz, Jea=3.2 Hz, 1H), 2.03 (d, J=10.4 Hz, 2H), 1.91 (d, J=10.8 Hz, 2H), 1.72-1.60 (m, 2H), 1.55-1.40 (m, 2H). MS (ESI): m/z 306.0 [M+H]$^+$.

Example 36: Compound 36: (1s,4s)-4-(3-chloro-6-hydroxyquinolin-2-yl)cyclohexanecarboxylic acid

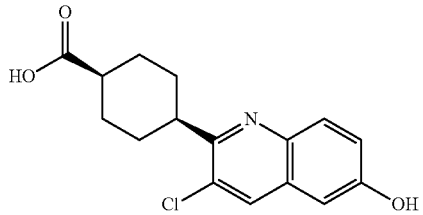 [SMILES: O=C(O)[C@H]1CC[C@@H](c2nc3ccc(O)cc3cc2Cl)CC1]

See Example 35 for synthesis. $^1$H NMR (DMSO 400 MHz): δ 10.11 (brs, 1H), 8.28 (s, 1H), 7.82 (d, J=9.2 Hz, 1H), 7.27 (dd, J=9.2, 2.8 Hz, 1H), 7.09 (d, J=2.8 Hz, 1H), 3.32-3.19 (m, 1H), 2.70-2.60 (m, 1H), 2.25-2.14 (m, 2H), 1.85-1.70 (m, 4H), 1.70-1.58 (m, 2H). MS (ESI): m/z 306.0 [M+H]$^+$.

Example 37: Compound 37: 3-chloro-4-(4-fluoro-6-hydroxyquinolin-2-yl)benzoic acid

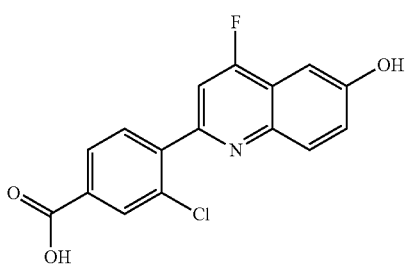 [SMILES: O=C(O)c1ccc(-c2cc(F)c3cc(O)ccc3n2)c(Cl)c1]

Followed Scheme 2, B conditions starting with 2-chloro-4-fluoro-6-methoxyquinoline (Intermediate 7) and 4-carboxy-2-chlorophenylboronic acid. $^1$H NMR (MeOD 400 MHz): δ 8.20 (d, J=1.2 Hz, 1H), 8.10 (dd, J=8.0, 1.6 Hz, 1H), 8.02 (d, J=9.2, 1.2 Hz, 1H), 7.75 (d, J=8.0 Hz, 1H), 7.52-7.45 (m, 2H), 7.47 (d, J=2.4 Hz, 1H). MS (ESI): m/z 317.9 [M+H]$^+$.

Example 38: Compound 38: 2-(5-(2H-tetrazol-5-yl)thiophen-2-yl)quinolin-6-ol

Step 1 and 2: Synthesis of 5-(6-hydroxyquinolin-2-yl)thiophene-2-carbonitrile

Followed the two step synthesis shown in Scheme 1 starting with 2-chloro-6-methoxyquinoline and 5-cyanothiophen-2-ylboronic acid, with minor variations: the base used in step 1 was sodium carbonate and the solvent was DME (dimethoxyethane)/water. In step 2, after quenching w/ice water, a standard ethyl acetate extraction was preformed followed by purification by prep-TLC (PE:EA=1:1).

Step 3: Synthesis of 2-(5-(2H-tetrazol-5-yl)thiophen-2-yl)quinolin-6-ol

Followed Scheme 4, route A. $^1$H-NMR (DMSO-d$_6$ 500 MHz): 10.15 (s, 1H), 8.23 (d, J=9.0 Hz, 1H), 8.05 (d, J=8.5 Hz, 1H), 7.99 (d, J=4.0 Hz, 1H), 7.86 (d, J=9.0 Hz, 1H), 7.78 (d, J=3.5 Hz, 1H), 7.34 (dd, J=2.5, 9.0 Hz, 1H), 7.17 (d, J=2.0 Hz, 1H). MS (ESI): m/z 296.0 [M+1]$^+$.

Example 39: Compound 39: 5-(4-(6-hydroxyquinolin-2-yl)phenyl)-1,2,4-thiadiazol-3(2H)-one

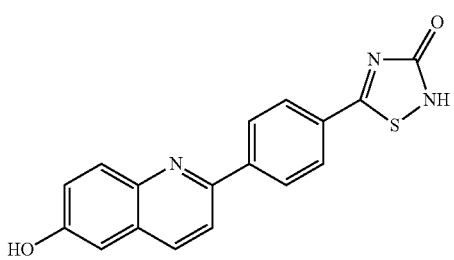 [SMILES: O=c1nc(-c2ccc(-c3ccc4cc(O)ccc4n3)cc2)s[nH]1]

Step 1: Synthesis of 4-(6-methoxyquinolin-2-yl)benzothioamide

To a suspension of 4-(6-methoxyquinolin-2-yl)benzamide (see Example 34 step 1 for synthesis, 3.00 g, 10.8 mmol) in anhydrous toluene (50 mL) was added Lawessen Reagent (2.60 g, 6.44 mmol). The mixture was refluxed for 3 hours. The mixture was diluted with MeOH (50 mL) and filtered off. The filtrate was concentrated under reduce pressure to give the crude product, which was purified by silica gel column (PE/EtOAc=1/1) to give the product (1.30 g, yield 41%) as a solid.

Step 2 and 3: Synthesis of 5-(4-(6-methoxyquinolin-2-yl)phenyl)-1,2,4-thiadiazol-3(2H)-one To a solution of 4-(6-methoxyquinolin-2-yl)benzothioamide (500 mg, 1.07 mmol) in DCE (10 mL) was added oxalylchloride (0.3 mL, 3.9 mmol) dropwise at 0° C. The mixture was heated to 90° C. for 2 hours. TMSN$_3$ (0.8 mL, 5.7 mmol) was added dropwise. The mixture was stirred at 100° C. for 2 hours. Water (10 mL) was added to the mixture. The mixture was filtered and the filter cake was washed with IPA (20 mL) to product (280 mg, yield 49%).

Step 4: Synthesis of 5-(4-(6-hydroxyquinolin-2-yl)phenyl)-1,2,4-thiadiazol-3(2H)-one Followed Scheme 2, Step 2, B conditions for demethylation. $^1$H NMR (DMSO 400 MHz): δ 12.76 (brs, 1H), 10.16 (brs, 1H), 8.41 (d, J=8.4 Hz, 2H), 8.29 (d, J=8.8 Hz, 1H), 8.15-8.02 (m, 3H), 7.95 (d, J=9.2 Hz, 1H), 7.36 (dd, J=9.2, 2.8 Hz, 1H), 7.19 (d, J=2.4 Hz, 1H), MS (ESI): m/z 321.9 [M+H]$^+$.

Example 40: Compound 40: 3-fluoro-4-(4-fluoro-6-hydroxyquinolin-2-yl)benzoic acid

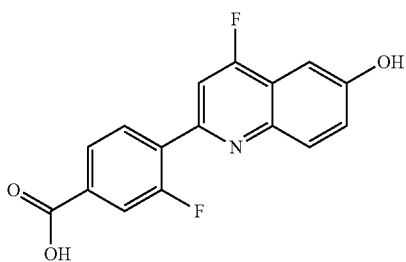 [SMILES: O=C(O)c1ccc(-c2cc(F)c3cc(O)ccc3n2)c(F)c1]

The compound was prepared following Scheme 2, B conditions starting from 2-chloro-4-fluoro-6-methoxyquinoline (Intermediate 7) and 4-carboxy-2-fluorophenylboronic acid. Note: In step 2, after purification by prep HPLC, the collected fractions were immediately neutralized with sat. NaHCO$_3$ to pH 6, followed by extraction with EtOAc/MeOH (v/v=10/1, 50 mL×3). Combined organics were washed with brine (50 mL), dried over Na$_2$SO$_4$ and concentrated in vacuo to give the desired product. $^1$H NMR (MeOD 400 MHz): δ 8.10-8.00 (m, 2H), 7.98 (dd, J=8.0, 1.2 Hz, 1H), 7.85 (dd, J=11.6, 1.2 Hz, 1H), 7.62 (dd, J=11.6, 2.0 Hz, 1H), 7.45 (dd, J=9.2, 2.8 Hz, 1H), 7.31 (d, J=2.8 Hz, 1H). MS (ESI): m/z 301.8 [M+H]$^+$.

Example 41: Compound 41: 1-(6-hydroxy-3-(trifluoromethyl)quinolin-2-yl)piperidine-4-carboxylic acid

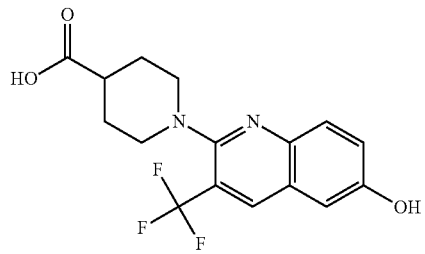 [SMILES: O=C(O)C1CCN(c2nc3ccc(O)cc3cc2C(F)(F)F)CC1]

Step 1: Synthesis of methyl 1-(6-methoxy-3-(trifluoromethyl)quinolin-2-yl)piperidine-4-carboxylate To a solution of 2-chloro-6-methoxy-3-(trifluoromethyl)quinoline (1.00 g, 3.85 mmol) (see Intermediate 6, Step 8 for synthesis) in IPA (5 mL) was added methyl-4-piperidinecarboxylate (5.50 g, 38.5 mmol) and Et$_3$N (1.17 g, 11.6 mmol). The mixture was heated to reflux for 48 hours. The mixture was diluted with water (100 mL) and extracted with DCM (100 mL×3), the combined organic layers were washed with brine (200 mL), dried over anhydrous Na$_2$SO$_4$, filtered and concentrated under reduced pressure to give the crude product, which was purified by column chromatography on silica gel (PE/EtOAc=15/1) to give the product (600 mg, yield 43%) as a solid.

Step 2: Synthesis of 1-(6-hydroxy-3-(trifluoromethyl)quinolin-2-yl)piperidine-4-carboxylic acid To a solution of methyl 1-(6-methoxy-3-(trifluoromethyl)quinolin-2-yl)piperidine-4-carboxylate (300 mg, 0.815 mmol) in DCM (5 mL) was added BBr$_3$ (0.4 mL, 4.08 mmol) dropwise at 0° C. The mixture was stirred at 0° C. for 20 hours. Water (10 mL) was added to the mixture dropwise at 0° C. The mixture was concentrated in vacuo, then diluted with EtOAc (150 mL), filtered and concentrated in vacuo. Purification by prep-HPLC (0.1% TFA as additive) to give Compound 41 (26 mg, yield 9.4%) as a solid. $^1$H NMR (MeOD 400 MHz): δ 8.51 (s, 1H), 7.82 (d, J=8.8 Hz, 1H), 7.41 (dd, J=8.8, 2.8 Hz, 1H), 7.21 (d, J=2.8 Hz, 1H), 3.55-3.49 (m, 2H), 3.13-3.02 (m, 2H), 2.58-2.49 (m, 1H), 2.09-2.00 (m, 2H), 1.93-1.82 (m, 2H). MS (ESI): m/z 340.7 [M+H]$^+$.

Example 42: Compound 42: 4-(5-chloro-6-hydroxyquinolin-2-yl)benzoic acid

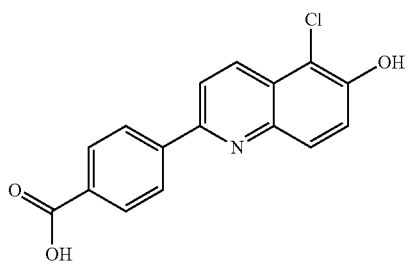 [SMILES: O=C(O)c1ccc(-c2ccc3c(Cl)c(O)ccc3n2)cc1]

Step 1: Synthesis of methyl 4-(6-methoxyquinolin-2-yl)benzoate

A mixture of 2-chloro-6-methoxyquinoline (Intermediate 1, 200 mg, 1.0 mmol), 4-(methoxycarbonyl) phenylboronic acid (205 mg, 1.1 mmol), Pd(dppf)Cl$_2$ (366 mg, 0.5 mmol) and sodium carbonate (212 mg, 2.0 mmol) in 1,4-dioxane/water (3 mL/0.6 mL) was heated to 120° C. by microwave for 1 h. The precipitates were filtered; washed with EA (10 mL), acetone (10 mL) and water (10 mL) separately; dried to afford product (120 mg, 40.9%).

Step 2: Synthesis of methyl 4-(5-chloro-6-methoxyquinolin-2-yl)benzoate

To a solution of above (100 mg, 0.34 mmol) in AcOH (2 mL) was added SO$_2$Cl$_2$ (55 mg, 0.41 mmol). The reaction mixture was heated to 60° C. for 3 h. Then the mixture was stirred at room temperature overnight. The precipitates were filtrated, washed with AcOH (10 mL×3) and dried to give the product as a powder (100 mg, 90.1%).

Step 3: Synthesis of 4-(5-chloro-6-hydroxyquinolin-2-yl)benzoic acid

Followed Scheme 1, step 2, with a purification by prep HPLC to give the product. $^1$H-NMR (DMSO-d$_6$ 500 MHz): 8.50 (d, J=9.0 Hz, 1H), 8.32 (d, J=8.0 Hz, 2H), 8.25 (d, J=8.5 Hz, 1H), 8.10 (d, J=8.0 Hz, 2H), 7.96 (d, J=9.5 Hz, 1H), 7.62 (d, J=9.0 Hz, 1H); MS (ESI): m/z 300.0 [M+1]$^+$.

Example 43: Compound 43: (1r,4r)-4-(6-hydroxy-3-(trifluoromethyl)quinolin-2-yl)cyclohexanecarboxylic acid

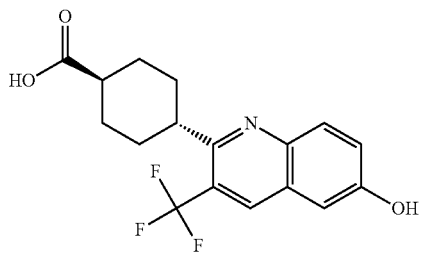 [SMILES: O=C(O)[C@H]1CC[C@H](c2nc3ccc(O)cc3cc2C(F)(F)F)CC1]

Step 1: Synthesis of ethyl 4-(6-methoxy-3-(trifluoromethyl)quinolin-2-yl)cyclohex-3-enecarboxylate Followed Scheme 2, Step 1 (see Ex. 8, Step 1) starting from ethyl 4-(4,4,5,5-tetramethyl-1,3,2-dioxaborolan-2-yl) cyclohex-3-enecarboxylate and 2-chloro-6-methoxy-3-(trifluoromethyl)quinoline (see Intermediate 6, Step 8 for synthesis), with a purification by column chromatography (PE/EtOAc=10/1).

Step 2: Synthesis of ethyl 4-(6-methoxy-3-(trifluoromethyl)quinolin-2-yl)cyclohexanecarboxylate Followed step 2 of Compound 35 with 0.15 equiv of catalyst at 20° C. for 4 days under H$_2$ (15 psi).

Step 3: Synthesis of (1r,4r)-4-(6-hydroxy-3-(trifluoromethyl)quinolin-2-yl)cyclohexanecarboxylic acid Followed step 3 of Compound 35, where the reaction was stirred at 10° C. for 20 hours before quenching with water. Purified crude by prep-HPLC to give ethyl 4-(6-methoxy-3-(trifluoromethyl)quinolin-2-yl)cyclohexanecarboxylate (Compound 43, 109 mg, yield 29%) as a solid, and (1s,4s)-4-(6-hydroxy-3-(trifluoromethyl)quinolin-2-yl)cyclohexanecarboxylic acid (Compound 44, 25 mg, yield 7%) as a solid. Compound 43 Data: $^1$H NMR (DMSO 400 MHz): δ 10.27 (brs, 1H), 8.61 (s, 1H), 7.89 (d, J=9.2 Hz, 1H), 7.44 (dd, J=9.2, 2.8 Hz, 1H), 7.32 (d, J=2.8 Hz, 1H), 3.01-2.91 (m, 1H), 2.40-2.30 (m, 1H), 2.00-1.90 (m, 2H), 1.95-1.78 (m, 4H), 1.53-1.38 (m, 2H). MS (ESI): m/z 339.9 [M+H]$^+$.

Example 44: Compound 44: (1s,4s)-4-(6-hydroxy-3-(trifluoromethyl)quinolin-2-yl)cyclohexanecarboxylic acid

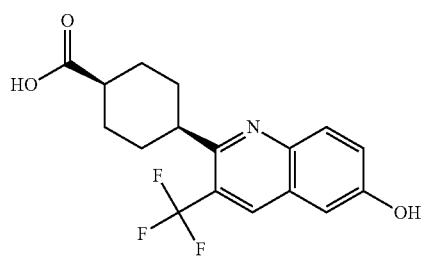 [SMILES: O=C(O)[C@H]1CC[C@@H](c2nc3ccc(O)cc3cc2C(F)(F)F)CC1]

See Example 43 for synthesis. $^1$H NMR (DMSO 400 MHz): δ 10.26 (br s, 1H), 8.59 (s, 1H), 7.89 (d, J=9.2 Hz, 1H), 7.43 (dd, J=9.2, 2.8 Hz, 1H), 7.31 (d, J=2.0 Hz, 1H), 3.09-2.95 (m, 1H), 2.75-2.62 (m, 1H), 2.28-2.16 (m, 2H), 1.98-1.80 (m, 2H), 1.60-1.55 (m, 4H). MS (ESI): m/z 339.9 [M+H]$^+$.

Example 45: Compound 45: 4-(5-bromo-6-hydroxyquinolin-2-yl)benzoic acid

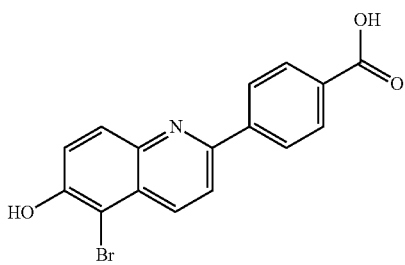 [SMILES: O=C(O)c1ccc(-c2ccc3c(Br)c(O)ccc3n2)cc1]

Step 1: Synthesis of methyl 4-(6-methoxyquinolin-2-yl)benzoate

A mixture of 2-chloro-6-methoxyquinoline (see U.S. 61/391,225 for synthesis) (200 mg, 1.0 mmol), 4-(methoxycarbonyl) phenylboronic acid (205 mg, 1.1 mmol), Pd(dppf) Cl$_2$ (366 mg, 0.5 mmol) and sodium carbonate (212 mg, 2.0 mmol) in 1,4-dioxane/water (3 mL/0.6 mL) was heated to 120° C. by microwave for 1 h. The precipitates were filtered; washed with EtOAc (10 mL), acetone (10 mL) and water (10 mL) separately; dried to give the product as a black solid. (120 mg, 40.9%).

Step 2: Synthesis of methyl 4-(5-bromo-6-methoxyquinolin-2-yl)benzoate

To a solution of methyl 4-(6-methoxyquinolin-2-yl)benzoate (630 mg, 2.15 mmol) in DCM (9 mL) was added Br$_2$ (0.3 mL, 6.45 mmol). The reaction mixture was stirred at room temperature overnight. Then the mixture was partitioned with brine and DCM. The precipitate was filtered and dried to give the product as a solid (800 mg, 100%). MS (ESI): m/z=373.0 [M+1]$^+$.

Step 3: Synthesis of Compound 45

To a solution of the product from above (150 mg, 0.40 mmol) in DCM (5 mL) was added BBr$_3$ (0.38 mL, 4.0 mmol) and stirred at room temperature overnight. Water (20 mL) was added carefully, the mixture was extracted with EtOAc (20 mL×3), concentrated and purified by prep-HPLC to afford Compound 45 as a grey powder (40 mg, 29.2%). MS (ESI): m/z=346.0 [M+1]$^+$. $^1$H-NMR (DMSO-d$^6$ 500 MHz): 8.48 (d, J=8.5 Hz, 1H), 8.35 (d, J=8.0 Hz, 2H), 8.25 (d, J=9.0 Hz, 1H), 8.10 (d, J=7.5 Hz, 2H), 8.01 (d, J=8.5 Hz, 1H), 7.60 (d, J=9.0 Hz, 1H) ppm.

Example 46: Compound 46: 3-bromo-4-(6-hydroxyquinolin-2-yl)benzoic acid

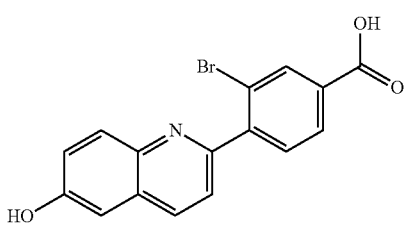 [SMILES: O=C(O)c1ccc(-c2ccc3cc(O)ccc3n2)c(Br)c1]

Step 1: Synthesis of methyl 3-amino-4-(6-methoxyquinolin-2-yl)benzoate

To a mixture of compound 2-chloro-6-methoxyquinoline (1.70 g, 8.78 mmol), 2-amino-4-(methoxycarbonyl)phenylboronic acid (2.05 g, 10.5 mmol), and K$_2$CO$_3$ (2.43 g, 17.6 mmol) in ethylene glycol monomethyl ether/H$_2$O (35 mL/5 mL) was added Pd(dppf)Cl$_2$ (158 mg, 0.193 mmol) under N$_2$ atmosphere. Then the mixture was heated to 80° C. for 3 hours. After aqueous workup with EtOAc extraction, the resulting crude product was purified by silica gel column (PE/EtOAc=15/1 to 3/1) to give the product (500 mg, yield 19%) as a yellow solid.

Step 2: Synthesis of methyl 3-bromo-4-(6-methoxyquinolin-2-yl)benzoate

To a mixture of the above product (200 mg, 0.649 mmol) in HBr (40%)/H$_2$O (5 mL/5 mL) was added NaNO$_2$ (44.8 mg, 0.649 mmol) in H$_2$O (3 mL) dropwise at 0° C., and the reaction mixture was stirred at 0° C. for 30 min. CuBr (186 mg, 1.30 mmol) was added and the mixture was stirred at 25° C. for 2 hours. The reaction mixture was basified with aqueous NaOH (2M) to pH=7-8, extracted with EtOAc (30 mL×3). The combined organic layers were washed with brine (30 mL), dried over anhydrous Na$_2$SO$_4$, filtered and concentrated under reduced pressure to give the product (205 mg, yield 85%) as a yellow solid.

Step 3: Synthesis of Compound 46

To a solution of the above product (205 mg, 0.550 mmol) in anhydrous DCM (6 mL) was added BBr$_3$ (0.26 mL, 2.8 mmol, d=2.64 g/mL) dropwise at 0° C. The resulting mixture was stirred at 25° C. for 48 hour. The reaction mixture was quenched with H$_2$O (30 mL) and filtered, the filter cake was washed with EtOAc (10 mL) to give compound 46 (90 mg, yield 48%) as a yellow solid. $^1$H NMR (DMSO-d$_6$ 400 MHz): δ 10.27 (brs, 1H), 8.36 (d, J=8.8 Hz, 1H), 8.24 (d, J=1.6 Hz, 1H), 8.06 (dd, J=8.0, 1.6 Hz, 1H), 7.95 (d, J=9.2 Hz, 1H), 7.76 (d, J=8.0 Hz, 1H), 7.71 (d, J=8.8 Hz, 1H), 7.41 (dd, J=9.2, 2.4 Hz, 1H), 7.26 (d, J=2.4 Hz, 1H). LC-MS purity: 94.8%. MS (ESI): m/z 343.9 [M+H]$^+$.

Example 47: Compound 47: 4-(4-(dimethylamino)-6-hydroxyquinolin-2-yl)benzoic acid

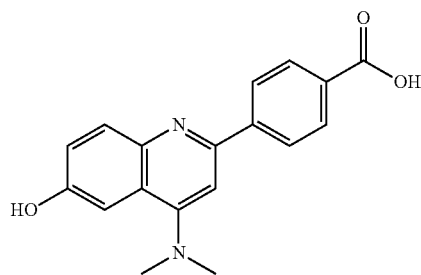 [SMILES: CN(C)c1cc(-c2ccc(C(=O)O)cc2)nc2ccc(O)cc12]

30 mg of 4-(4-fluoro-6-hydroxyquinolin-2-yl)benzoic acid (Compound 26) was mixed with 1 mmol Me$_2$NH.HCl and 0.5 ml DIEA in 3 ml DMF and heated to 160° C. for 30 minutes. The solvent was evaporated to dryness and water was added. The solid was filtered and washed with water and dried. The crude was triturated with acetone to obtain 10.5 mg of Compound 47. $^1$H NMR (DMSO-d$_6$ 300 MHz TMS): δ 13.2 (b, 1H), 10.28 (s, 1H), 8.22 (m, 2H), 8.11 (d, 1H), 7.99 (d, 1H), 7.50 (s, 1H), 7.39 (d, 1H), 7.26 (s, 1H), 3.24 (s, 6H), MS (ESI): m/z=309.30 [M+1]+.

Example 48: Compound 48: 4-(4-fluoro-6-hydroxyquinolin-2-yl)-3-methoxybenzoic acid

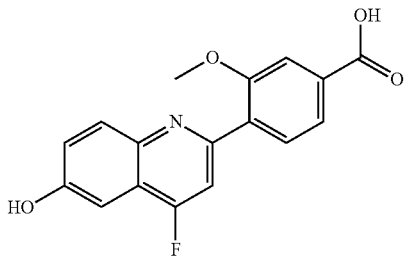 [SMILES: COc1cc(C(=O)O)ccc1-c1cc(F)c2cc(O)ccc2n1]

Step 1: Synthesis of 2-chloro-4-fluoroquinolin-6-ol

A mixture solution of 2-chloro-4-fluoro-6-methoxyquinoline (see U.S. 61/391,225 for synthesis) (280 mg, 1.32 mmol) and BBr$_3$ (0.3 mL, 3.2 mmol, 2.64 g/mL) in DCM (5 mL) was stirred at 20° C. for 12 hours. Aqueous workup with DCM extraction gave the crude product, which was purified by silica gel column (PE/EtOAc=50/1) to give product (177 mg, yield 69%) as a white solid.

Step 2: Synthesis of Compound 48

A mixture of the above product (133 mg, 0.670 mmol), 4-(dihydroxyboryl)-3-methoxybenzoic acid (156 mg, 0.801 mmol), K₂CO₃ (278 mg, 2.01 mmol), Pd(dppf)Cl₂ (30 mg, 0.026 mmol) in DMF (3 mL) and H₂O (0.6 mL) was stirred under N₂ atmosphere at 130° C. for 2.5 hours. The mixture was cooled to room temperature, acidified with aqueous HCl (1M) until pH=6 and extracted with EtOAc (30 mL×3). The combined organic layer was washed with brine (50 mL), dried over anhydrous Na₂SO₄ and concentrated in vacuo. The residue was purified by silica gel column (DCM/MeOH=15/1) to give Compound 48 (10.5 mg, yield 5%) as an off-white solid. ¹H NMR (CD₃OD 400 MHz TMS): δ 8.01 (dd, J=8.8, 1.2 Hz, 1H), 7.88-7.76 (m, 3H), 7.63 (d, J=11.2 Hz, 1H), 7.43 (dd, J=9.2, 2.8 Hz, 1H), 7.33 (d, J=2.8 Hz, 1H), 3.98 (s, 3H). MS (ESI): m/z 313.8 [M+H]⁺.

Example 49: Compound 49:
3-cyano-4-(6-hydroxyquinolin-2-yl)benzoic acid

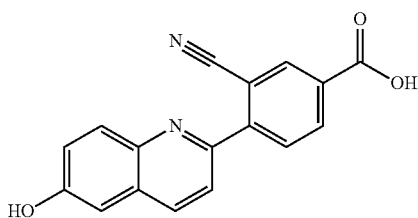 [SMILES: N#Cc1cc(C(=O)O)ccc1-c1ccc2cc(O)ccc2n1]

Step 1: Synthesis of 2-Methoxyethyl 3-amino-4-(6-methoxyquinolin-2-yl)benzoate

Followed the coupling procedure described in step 1 of Compound 46, starting from 2-chloro-6-methoxyquinoline (1.70 g, 8.78 mmol) and 2-amino-4-(methoxycarbonyl)phenylboronic acid (2.05 g, 10.5 mmol). Note: Ester exchange occurred between desired compound and solvent. Obtained the product (1.10 g, yield 35%) as a yellow solid.

Step 2: Synthesis of 2-methoxyethyl 3-bromo-4-(6-methoxyquinolin-2-yl)benzoate

To a mixture of the above product (500 mg, 1.42 mmol) in HBr (40%)/H₂O (10 mL/10 mL) was added NaNO₂ (97.9 mg, 1.42 mmol) in H₂O (5 mL) dropwise at 0° C., and the reaction mixture was stirred at 0° C. for 30 min. CuBr (407 mg, 2.84 mmol) was added, and the mixture was stirred at 25° C. for 2 hours, then basified with aqueous NaOH (2M) to pH=7-8, and extracted with EtOAc (20 mL×3). The combined organic layers were washed with brine (20 mL), dried over anhydrous Na₂SO₄, filtered and concentrated in vacuo to give the product (580 mg, yield 98%) as a yellow solid.

Step 3: Synthesis of 2-methoxyethyl 3-cyano-4-(6-methoxyquinolin-2-yl)benzoate

To a solution of the above product (580 mg, 1.40 mmol) in DMF (15 mL) was added Zn(CN)₂ (329 mg, 2.80 mmol) and Pd(PPh₃)₄ (162 mg, 0.140 mmol). The resulting mixture was stirred at 120° C. under N₂ atmosphere for 16 hours. After cooling to room temperature, the mixture was filtered and the filtrate was diluted with EtOAc (60 mL), washed with H₂O (20 mL×3) and brine (20 mL), dried over anhydrous Na₂SO₄, filtered and concentrated under reduced pressure to give the crude product. The crude product was purified by silica gel column (PE/EtOAc=50/1 to 10/1) to give the product (180 mg, yield 36%) as a yellow solid.

Step 4: Synthesis of 2-hydroxyethyl 3-cyano-4-(6-hydroxyquinolin-2-yl)benzoate

To a solution of the above product (180 mg, 0.497 mmol) in anhydrous DCM (10 mL) was added BBr₃ (0.24 mL, 2.5 mmol, d=2.64 g/mL) dropwise at 0° C. The resulting mixture was stirred at 25° C. for 2 hours. Water was added (20 mL), then basified with aqueous NaOH (2M) to pH=7-8, and extracted with DCM (30 mL×3). The combined organic layers were washed with brine (30 mL), dried over anhydrous Na₂SO₄, filtered and concentrated in vacuo to give the product (100 mg, yield 60%) as an off-white solid.

Step 5: Synthesis of Compound 49

To a solution of the above product (100 mg, 0.299 mmol) in MeOH (5 mL) and THF (5 mL) was added LiOH.H₂O (25.1 mg, 0.598 mmol). The mixture was stirred at 25° C. for 16 hours. The reaction mixture was acidified with 1N HCl to pH=5-6, and the resulting mixture was extracted with EtOAc (20 mL×3). The combined organic layers were washed with brine (20 mL), dried over anhydrous Na₂SO₄, filtered and concentrated to give the crude product. The crude product was washed with EtOAc (10 mL) to give Compound 49 (35 mg, yield 45%) as a yellow solid. ¹H NMR (DMSO-d₆ 400 MHz): δ 13.66 (brs, 1H), 10.32 (brs, 1H), 8.40 (d, J=1.6 Hz, 1H), 8.37 (d, J=8.4 Hz, 1H), 8.32 (dd, J=8.0, 1.6 Hz, 1H), 8.16 (d, J=8.0 Hz, 1H), 8.02-7.90 (m, 2H), 7.42 (dd, J=9.2, 2.8 Hz, 1H), 7.25 (d, J=2.8 Hz, 1H). MS (ESI): m/z 290.6 [M+H]⁺.

Example 50: Compound 50:
2-(4-carboxy-2-chlorophenyl)-6-hydroxyquinoline 1-oxide

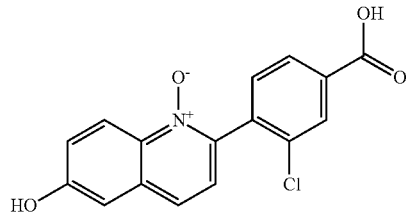 [SMILES: O=C(O)c1ccc(-c2ccc3cc(O)ccc3[n+]2[O-])c(Cl)c1]

To a solution of 3-chloro-4-(6-hydroxyquinolin-2-yl)benzoic acid (Compound 8) (620 mg) in HOAc (8 mL) was added 3-chloroperbenzoic acid (77% pure, 1.19 g). The resultant mixture was heated at 90° C. over 3 hour. After removal of HOAc under reduced pressure, the resultant mixture was triturated with DCM and recrystallized from EtOH/water twice to afford the desired product (245 mg) as colorless solids. ¹H NMR (DMSO-d₆ 300 MHz TMS): δ 10.49 (1H, s), 8.43 (1H, d, J=9 Hz), 8.06 (1H, d, J=3 Hz), 8.01 (1H, dd, J=9 and 3 Hz), 7.82 (1H, d, J=6 Hz), 7.69 (1H, d, J=6 Hz), 7.47 (1H, d, J=9 Hz), 7.37 (1H, dd, J=9 and 3 Hz), 7.31 (1H, d, J=3 Hz) ppm; MS (ESI): m/z 316, [M+H⁺].

Example 51: Compound 51: 4-(4-amino-6-hydroxyquinolin-2-yl)benzoic acid

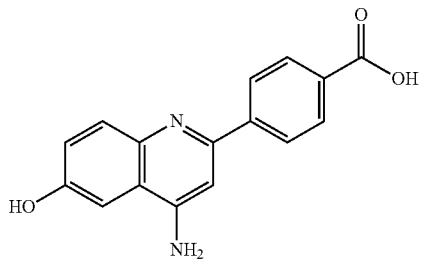 [SMILES: Nc1cc(-c2ccc(C(=O)O)cc2)nc2ccc(O)cc12]

Step 1: Synthesis of methyl 4-(4-amino-6-methoxyquinolin-2-yl)benzoate

A mixture solution of Intermediate 8 (4.70 g, 22.5 mmol), 4-methoxycarbonylphenylboronic acid (4.01 g, 22.5 mmol), $K_2CO_3$ (6.53 g, 47.2 mmol), Pd(dppf)$Cl_2$ (470 mg, 0.407 mmol) in DMF (20 mL) and $H_2O$ (4 mL) was stirred under $N_2$ atmosphere at 130° C. for 5 hours. The mixture was cooled, acidified with aqueous HCl (1M) until pH=6 and extracted with EtOAc (80 mL×3). The combined organic layers were washed with brine (150 mL), dried over anhydrous $Na_2SO_4$ and concentrated in vacuo. The residue was washed with EtOAc (50 mL), the mixture was filtered then concentrated to give the product (3.20 g, yield 46%) as an off-white solid.

Step 2: Synthesis of Compound 51

A mixture the above product (300 mg, 0.97 mmol) and $BBr_3$ (1 mL, 10.5 mmol, 2.64 g/mL) in DCM (10 mL) was stirred at 20° C. for 72 hours. Water was added (20 mL), and extracted with DCM (20 mL×3), dried over anhydrous $Na_2SO_4$ and concentrated in vacuo to give crude product. Trituration with MeOH (20 mL) gave Compound 51 (29.0 mg, yield 11%) as a yellow solid. $^1$H NMR (DMSO-$d_6$ 400 MHz TMS): δ 13.52 (brs, 1H), 10.53 (brs, 1H), 8.74 (brs, 2H), 8.20 (d, J=8.4 Hz, 2H), 8.01-7.96 (m, 3H), 7.65 (d, J=1.6 Hz, 1H), 7.56 (dd, J=9.2, 2.4 Hz, 1H), 6.98 (s, 1H). MS (ESI): m/z 280.9 [M+H]$^+$.

Example 52: Compound 52: 4-(3-cyano-6-hydroxyquinolin-2-yl)benzoic acid

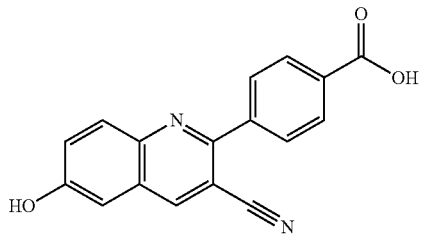 [SMILES: N#Cc1cc2cc(O)ccc2nc1-c1ccc(C(=O)O)cc1]

Step 1: Synthesis of 2-chloro-6-methoxyquinoline-3-carbonitrile

To a mixture of 2-chloroquinoline-3-carboxaldehyde (1.00 g, 4.50 mmol) in THF (30 mL) was added $NH_3 \cdot H_2O$ (30 mL, 25%) and $I_2$ (1.26 g, 4.90 mmol), the mixture was stirred at 20° C. for 8 hours. Aqueous workup with EtOAc extraction gave the crude product. Purification by silica gel column (PE/EtOAc=10/1 to 2/1) gave the product (370 mg, yield 38%) as a yellow solid.

Step 2: Synthesis of 4-(3-cyano-6-methoxyquinolin-2-yl)benzoic acid

To a mixture of the above product (75.0 mg, 0.350 mmol) in DMF/$H_2O$ (5 mL/1 mL) was added 4-Carboxyphenylboronic acid (57.0 mg, 0.350 mmol), $K_2CO_3$ (73.0 mg, 0.525 mmol) and PdCl$_2$(dppf) (20.0 mg, 2.73×10$^{-3}$ mmol), the reaction mixture was degassed (3×'s) and heated to 100° C. for 3 hours. The reaction mixture was acidified with aqueous HCl (1M) to pH=6, extracted with EtOAc (5 mL×3); the organic layers were washed with brine (5 mL), dried over anhydrous $Na_2SO_4$, filtered and concentrated in vacuo. Purification by silica gel column (PE/EtOAc=4/1 to 0/1) gave the product (45.0 mg, yield 42%) as a yellow solid.

Step 3: Synthesis of Compound 52

To a solution of the above product (80.0 mg, 0.263 mmol) in DCM (2.5 mL) was added $BBr_3$ (0.4 mL) dropwise. The resulting mixture was stirred at 30° C. under $N_2$ atmosphere for 24 hours. Aqueous workup with EtOAc extraction gave the crude product. Purification by Prep-HPLC (0.1% TFA as additive) gave Compound 52 (6.0 mg, yield 8%) as a white solid. $^1$H NMR (MeOD-$d_6$ 400 MHz): δ 8.78 (s, 1H), 8.22 (d, J=8.0 Hz, 2H), 8.05-8.01 (m, 3H), 7.56 (dd, J=9.2, 2.8 Hz, 1H), 7.28 (d, J=2.4 Hz, 1H). MS (ESI): m/z 290.8 [M+H]$^+$.

Example 53: Compound 53: 4-(5-fluoro-6-hydroxyquinolin-2-yl)benzoic acid

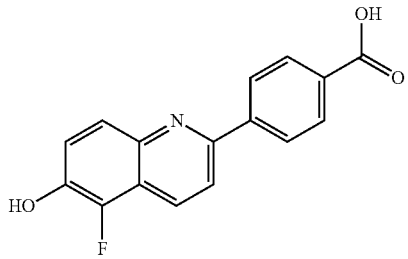 [SMILES: O=C(O)c1ccc(-c2ccc3c(F)c(O)ccc3n2)cc1]

Step 1: Synthesis of methyl 4-(5-fluoro-6-methoxyquinolin-2-yl)benzoate

To a solution of methyl 4-(6-methoxyquinolin-2-yl)benzoate (see Compound 45, step 1 for synthesis) (250 mg, 0.85 mmol) in MeCN (5 mL) was added selectfluoro (453 mg, 1.28 mmol). The reaction mixture was heated at 50° C. overnight. The solvent was removed under reduced pressure, followed by aqueous workup with DCM extraction to afford the product as a brown solid (300 mg, 113%).

Step 2: Synthesis of Compound 53

To a solution of the above product (300 mg, 0.96 mmol) in DCM (2 mL) was added $BBr_3$ (2.4 g, 9.6 mmol). The reaction mixture was stirred at the room temperature overnight. Water (40 mL) was added carefully. The precipitates were collected and purified by prep-HPLC to afford Compound 53 as a brown powder (76.8 mg, 25.9%). ¹H-NMR (DMSO-d₆ 500 MHz TMS): 8.45 (d, J=9.0 Hz, 1H), 8.35 (d, J=8.5 Hz, 2H), 8.22 (d, J=9.0 Hz, 1H), 8.10 (d, J=8.5 Hz, 2H), 7.84 (d, J=9.5 Hz, 1H), 7.56 (t, J=9.5 Hz, 1H) ppm. MS (ESI): m/z=284.1 [M+1]⁺.

Example 54: Compound 54: 4-(8-fluoro-6-hydroxyquinolin-2-yl)benzoic acid

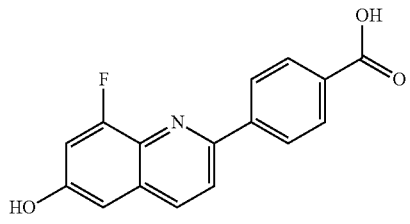 [SMILES: O=C(O)c1ccc(-c2ccc3cc(O)cc(F)c3n2)cc1]

Step 1: Synthesis of methyl 4-(8-fluoro-6-hydroxyquinolin-2-yl)benzoate

Following the general Suzuki coupling condition, 2-chloro-8-fluoroquinolin-6-yl acetate (Intermediate 9) (89.3 mg) was treated with (4-(methoxycarbonyl)phenyl) boronic acid (74 mg), Pd(dppf)Cl₂ (cat.) and sodium bicarbonate (69 mg) in Dioxane (2 mL) and water (0.4 mL) at 100° C. with microwave heating over 2 hours. After aqueous work-up, a flash silica gel column purification afforded a mixture of methyl 4-(8-fluoro-6-hydroxyquinolin-2-yl)benzoate and methyl 4-(6-acetoxy-8-fluoroquinolin-2-yl)benzoate (120 mg) as light brown solids.

Step 2: Synthesis of Compound 54

A mixture of methyl 4-(8-fluoro-6-hydroxyquinolin-2-yl) benzoate and methyl 4-(6-acetoxy-8-fluoroquinolin-2-yl) benzoate (120 mg) was hydrolyzed with 2N NaOH (4 mL) in MeOH (4 mL). The desired product-4-(8-fluoro-6-hydroxyquinolin-2-yl)benzoic acid (65 mg) was collected by filtration after acidification with 12N HCl. ¹H NMR (DMSO-d₆ 300 MHz TMS): δ 8.36-8.33 (3H, m), 8.18 (1H, d, J=9 Hz), 8.09 (2H, d, J=9 Hz), 7.24 (1H, dd, J=12 and 3 Hz), 7.09 (1H, d, J=3 Hz) ppm, MS (ESI): m/z 284, [M+H⁺].

Example 55: Compound 55: 3-hydroxy-4-(6-hydroxyquinolin-2-yl)benzoic acid

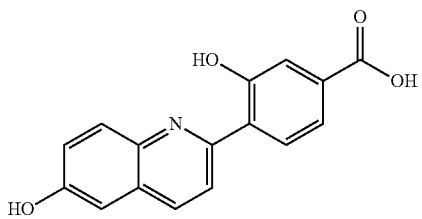 [SMILES: O=C(O)c1ccc(-c2ccc3cc(O)ccc3n2)c(O)c1]

70 mg of 4-(6-hydroxyquinolin-2-yl)-3-methoxybenzoic acid (Compound 48) was suspended in 10 ml DCM and 0.25 ml BBr₃ was added. The mixture was stirred at room temperature for 2 days. 20 ml water was added to quench the reaction. DCM was removed by evaporation and the precipitate was filtered and washed with water and dried to obtain 29 mg of 3-hydroxy-4-(6-hydroxyquinolin-2-yl)benzoic acid. 1H NMR (DMSO-d₆ 300 MHz TMS): δ 10.34 (s, 1H), 8.45 (d, 1H), 8.30 (d, 1H), 8.24 (d, 1H), 7.97 (d, 1H), 7.46 (m, 3H), 7.26 (d, 1H), MS (ESI): m/z=282.30 [M+1]+.

Example 56: Compound 56: 3-fluoro-4-(5-fluoro-6-hydroxyquinolin-2-yl)benzoic acid

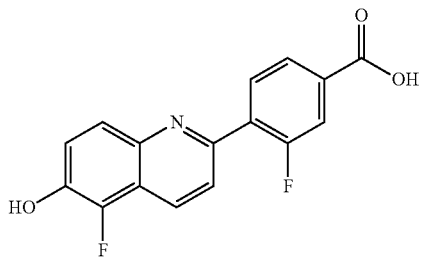 [SMILES: O=C(O)c1ccc(-c2ccc3c(F)c(O)ccc3n2)c(F)c1]

Step 1: Synthesis of methyl 3-fluoro-4-(6-methoxyquinolin-2-yl)benzoate

A mixture of 2-chloro-6-methoxyquinoline (Intermediate 1) (300 mg, 1.55 mmol), methyl 3-fluoro-4-(4,4,5,5-tetramethyl-1,3,2-dioxaborolan-2-yl)benzoate (Intermediate 10) (415 mg, 1.48 mmol), Pd(dppf)Cl₂ (110 mg, 0.15 mmol) and sodium carbonate (320 mg, 3.0 mmol) in 1,4-dioxane/water (6 mL/1 mL) was heated to 120° C. under microwave irradiation for 4 h. The precipitate was filtered and washed with EA. The combined filtrate was washed with brine, dried over Na₂SO₄, filtered and concentrated in vacuo. The residue was purified by silica gel chromatography (PE/EA=30/1) to give the product (220 mg, 46%) as white solid. MS (ESI): m/z 312.2 [M+1]⁺.

Step 2: Synthesis of methyl 3-fluoro-4-(5-fluoro-6-methoxyquinolin-2-yl)benzoate To a solution of the above product (260 mg, 0.835 mmol) in CH₃CN (30 mL) was added selectfluoro (296 mg, 0.835 mmol). The reaction mixture was heated at 50° C. for 3 h and concentrated. The residue was partitioned between water (20 mL) and DCM (20 mL). The aqueous phase was separated and extracted with DCM (20 mL×2). The combined organic layers was washed with brine (50 mL), dried over Na₂SO₄, filtered and concentrated. The residue was purified by silica gel chromatography (PE/EA=30/1) to give the product (190 mg, crude). MS (ESI): m/z=330.1 [M+1]⁺.

Step 3: Synthesis of Compound 56

To an ice cooled solution of the above product (190 mg, 0.577 mmol) in DCM (2 mL) was added BBr₃ (1.45 g, 5.77 mmol). The reaction mixture was stirred overnight at room temperature and slowly quenched with water (40 mL). The precipitate was collected and purified by prep-HPLC to give Compound 56 as a brown powder (140 mg, 81%). ¹H-NMR (DMSO-d₆, 500 MHz, TMS): δ 8.47 (d, J=8.5 Hz, 1H), 8.15 (t, J=8.0 Hz, 1H), 7.97 (dd, J=2.5 Hz, 1H), 7.93 (dd J=1.5 Hz, 1H), 7.82-7.86 (m, 2H), 7.57 (t, J=9.0 Hz, 1H) ppm; MS (ESI): m/z=302.1 [M+1]⁺.

Example 57: Synthesis of Intermediates

Intermediate 1: Synthesis of 2-chloro-6-methoxyquinoline

Step 1: Synthesis of 6-methoxyquinoline 1-oxide

To a solution of 6-methoxyquinoline (2.00 g, 12.6 mmol) in AcOH (10 mL) was added $H_2O_2$ (30% in water, 1.9 mL, 18.9 mmol), the mixture was heated to 70° C. for 21 hours. The mixture was basified with 2M NaOH to pH 8-9 and extracted with $CH_2Cl_2$ (200 mL), the combined organic layer was washed with brine (50 mL), dried over $Na_2SO_4$, filtered and concentrated to give the crude product, which was purified by silica gel column (EtOAc/MeOH=10/1) to give 6-methoxyquinoline 1-oxide (1.20 g, 55%) as a solid.

Step 2: Synthesis of 6-methoxyquinolin-2-ol

A solution of 6-methoxyquinoline 1-oxide (300 mg, 1.71 mmol) in $Ac_2O$ (5.0 mL) was refluxed for 2 hours. The solvent was removed under reduced pressure. The residue was dissolved in EtOAc (50 mL), the organic layer was washed with brine (10 mL), dried over $Na_2SO_4$, filtered and concentrated to give the crude product which was purified by silica gel column (PE/EtOAc=1/2) to give 6-methoxyquinolin-2-ol (200 mg, yield 67%).

Step 3: Synthesis of 2-chloro-6-methoxyquinoline

A solution of 6-methoxyquinolin-2-ol (400 mg, 2.29 mmol) in $POCl_3$ (5.0 mL) was refluxed for 2 hours. The solvent was removed under reduced pressure and the residue was dissolved in EtOAc (50 mL), the organic layer was washed with saturated $NaHCO_3$ (30 mL×2), dried over $Na_2SO_4$, filtered and concentrated to give the crude product, which was purified by silica gel column (PE/EtOAc=10/1) to give 2-chloro-6-methoxyquinoline (380 mg, yield 86%) as a solid. $^1$H NMR (CDCl3 400 MHz): δ 7.92 (d, J=8.4 Hz, 1H), 7.85 (d, J=9.2 Hz, 1H), 7.32-7.25 (m, 2H), 7.00 (d, J=2.4 Hz, 1H), 3.86 (s, 3H).

Intermediate 2: Synthesis of 2-chloroquinolin-6-ol

To a solution of 2-chloro-6-methoxyquinoline (Intermediate 1) (2.00 g, 10.4 mmol) in anhydrous DCM (100 mL) was added $BBr_3$ (6 mL, 62.2 mmol) dropwise at 0° C. The reaction mixture was stirred at 25° C. for 2 hours, then quenched with aqueous saturated $NH_4Cl$ (50 mL) and filtered. The filtrate was extracted with $CH_2Cl_2$/MeOH (v/v=10/1, 30 mL×2) and the combined organic layers were washed with brine (30 mL), dried over $Na_2SO_4$, filtered and concentrated under reduced pressure to give 2-chloroquinolin-6-ol (1.30 g, yield 70%) as yellow solid. $^1$H NMR (CDCl$_3$ 300 MHz): δ 7.95 (t, J=8.1 Hz, 2H), 7.35 (dd, J=6.0, 3.3 Hz, 2H), 7.13 (d, J=2.7 Hz, 1H).

Intermediate 3: Synthesis of 2,4-dichloro-3-fluoro-6-methoxyquinoline

Step 1: Synthesis of 2-fluoromalonic acid

To a solution of diethyl 2-fluoromalonate (5.00 g, 28.1 mmol) in EtOH (100 mL) was added LiOH.H$_2$O (2.70 g, 64.3 mmol) at 25° C. The mixture was heated to 50° C. for 16 hours. The mixture was filtered to collect solid. The filtrate was concentrated to dryness to get oil. The oil and the solid were dissolved in H$_2$O (30 mL) and MTBE (100 mL), the mixture was acidified by adding conc. HCl to pH 1, the aqueous layer was extracted with MTBE (30 mL×2), the combined organic layers were dried over $Na_2SO_4$, filtered and concentrated to give 2-fluoromalonic acid (3.00 g, yield 88%) as a solid.

Step 2: Synthesis of 2,4-dichloro-3-fluoro-6-methoxyquinoline

A suspension of fluoromalonic acid (1.00 g, 8.13 mmol) in $POCl_3$ (10 mL) was heated to 85° C. to dissolve the solid. The mixture was cooled to 60° C. and p-anisidine (900 mg, 7.32 mmol) was added portion wise over 1 hour. After addition, the reaction mixture was refluxed for 2 hours. The solvent was removed in vacuo. The mixture was diluted with ice water and basified by adding $NH_3.H_2O$ to pH 9. The aqueous layer was extracted with EtOAc (30 mL×3), the combined organic layers were washed with brine (20 mL), dried over $Na_2SO_4$, filtered and concentrated to give the crude product, which was purified by silica gel column (PE/EtOAc=10/1) to give 2,4-dichloro-3-fluoro-6-methoxyquinoline (650 mg, yield 36%). $^1$H NMR (CDCl$_3$ 300 MHz): δ 7.92 (d, J=9.0 Hz, 1H), 7.41-7.31 (m, 2H), 4.00 (s, 3H).

Intermediate 4: Synthesis of 2,3-dichloro-6-methoxyquinoline

Step 1: Synthesis of 2-chloro-N-(4-methoxyphenyl)acetamide

A mixture of 4-methoxyaniline (5.00 g, 40.6 mmol), chloroacetic acid (8.6 g, 91.5 mmol), EDCI (12.0 g, 61.2 mmol), HOBT (8.4 g, 61.3 mmol) and NMM (13 mL, 122 mmol) in anhydrous $CH_2Cl_2$ (50 mL) was stirred at 30° C. for 3 hours. The mixture was quenched with ice water, and then extracted with $CH_2Cl_2$ (30 mL×2). The combined organic layers were washed with brine (30 mL), dried over $Na_2SO_4$, filtered and concentrated to give the crude product, which was purified by silica gel column (PE/EtOAc=5/1) to give the product (1.60 g, yield 20%).

Step 2: Synthesis of 2,3-dichloro-6-methoxyquinoline $POCl_3$ (1.6 mL, 17.5 mmol) was added dropwise to DMF (0.29 mL, 3.80 mmol) at 0° C. After addition, 2-chloro-N-(4-methoxyphenyl)acetamide (500 mg, 2.50 mmol) was added portionwise. The mixture was stirred at 25° C. for 15 minutes and heated to 75° C. for 3 hours. The reaction mixture was quenched with ice water and neutralized by 2M NaOH to pH 7. An aqueous workup with EtOAc was followed by purification by silica gel column (PE/EtOAc=20/1) to give Intermediate 4 (50 mg, yield 9%). $^1$H NMR (CDCl$_3$ 400 MHz): δ 8.06 (s, 1H), 7.81 (d, J=9.6 Hz, 1H), 7.30 (dd, J=9.2, 2.8 Hz, 1H), 6.92 (d, J=2.8 Hz, 1H), 3.87 (s, 3H).

Intermediate 5: Synthesis of methyl 4-(4,4,5,5-tetramethyl-1,3,2-dioxaborolan-2-yl)-3-(trifluoromethyl)benzoate To a mixture of methyl 4-bromo-3-(trifluoromethyl)benzoate (1.00 g, 3.53 mmol), bis(pinacolato)diboron (1.79 g, 7.06 mmol), and KOAc (1.04 g, 10.6 mmol) in DMSO (15 mL) was added Pd(PPh$_3$)$_4$ (816 mg, 0.706 mmol) under N$_2$ atmosphere. Then the mixture was heated to 120° C. for 3 hours. The reaction mixture was cooled followed by an aqueous/EtOAc workup gave the crude product (2.3 g) as a yellow oil.

Intermediate 6: Synthesis of 2-chloro-3-(trifluoromethyl)quinolin-6-ol

Step 1: Synthesis of (5-methoxy-2-nitrophenyl)methanol

To a solution of 5-methoxy-2-nitrobenzoic acid (20.0 g, 0.102 mol) in anhydrous THF (200 mL) was added $SOCl_2$ (20 mL), the mixture was refluxed for 4 hours. The solvent was removed under reduced pressure and the residue was dissolved in anhydrous THF (100 mL). The solution was added dropwise to a suspension of $NaBH_4$ (7.70 g, 0.202 mol) in anhydrous THF (100 mL) and DMF (140 mL) at 0° C. over a period of 30 minutes. The mixture was stirred at 30° C. for 3 hours, then quenched with ice-water (100 mL) and basified by 2M NaOH to pH 8. An EtOAc workup was followed by removal of solvent in vacuo and purification by column chromatography (PE/EtOAc=1/1) to give the product (12.0 g, yield 66%).

Step 2: Synthesis of tert-butyl(5-methoxy-2-nitrobenzyloxy)dimethylsilane

To a solution of (5-methoxy-2-nitrophenyl)methanol (12.0 g, 65.6 mmol) in anhydrous THF (200 mL) and DMF (20 mL) was added imidazole (9.80 g, 144 mmol). Then TBSCl (11.8 g, 78.6 mmol) was added portionwise at 0° C. and the mixture was stirred at 30° C. for 2 hours. The mixture was quenched with ice-water (100 mL). An EtOAc workup was followed by removal of solvent in vacuo and purification by column chromatography (PE/EtOAc=10/1) to give the product (16.0 g, yield 84%) as a yellow oil.

Step 3: Synthesis of 2-((tert-butyldimethylsilyloxy)methyl)-4-methoxyaniline To a solution of tert-butyl(5-methoxy-2-nitrobenzyloxy) dimethylsilane (14.0 g, 47.1 mmol) in EtOH (200 mL) was added 10% Pd/C (1.40 g), the mixture was stirred at 30° C. for 2 hours under $H_2$ (40 psi). The solids were filtered off and the filtrate was concentrated under reduced pressure to give the product (14.0 g) as a yellow oil. $^1$H NMR (DMSO 400 MHz): δ 6.75 (d, J=2.4 Hz, 1H), 6.60-6.55 (m, 2H), 4.55 (s, 2H), 4.40 (brs, 2H), 3.61 (s, 3H), 0.90 (s, 9H), 0.09 (s, 6H).

Step 4: Synthesis of N-(2-(((tert-butyldimethylsilyloxy)methyl)-4-methoxyphenyl)-3,3,3-trifluoropropanamide A mixture of 2-((tert-butyldimethylsilyloxy) methyl)-4-methoxyaniline (14.0 g), 3,3,3-trifluoro-propionic acid (7.30 g, 57.0 mmol), EDCI (15.0 g, 76.5 mmol), HOBT (11.0 g, 80.2 mmol) and NMM (22 mL, 157 mmol) in anhydrous $CH_2Cl_2$ (200 mL) was stirred at 20° C. for 2 hours. The mixture was diluted with $CH_2Cl_2$ (100 mL), the organic layer was washed with 1M HCl (100 mL), $H_2O$ (100 mL) and brine (100 mL), dried over $Na_2SO_4$ and concentrated to give the product.

Step 5: Synthesis of 3,3,3-trifluoro-N-(2-(hydroxymethyl)-4-methoxyphenyl)propanamide To a solution of N-(2-(((tert-butyldimethylsilyloxy) methyl)-4-methoxyphenyl)-3,3,3-trifluoropropanamide (20.0 g) in anhydrous THF (200 mL) was added a solution of TBAF (16.6 g, 63.6 mmol) in anhydrous THF (60 mL). The mixture was stirred at 35° C. for 30 minutes. The mixture was quenched with ice-water. An aqueous/EtOAc workup was followed by removal of volatiles in vacuo. The crude product was purified by column chromatography on silica gel (PE/EtOAc=1/2) to give the desired product. $^1$H NMR (CDCl3 400 MHz): δ 8.60 (brs, 1H), 7.82 (d, J=8.8 Hz, 1H), 6.85 (dd, J=9.2, 3.2 Hz, 1H), 6.75 (d, J=2.8 Hz, 1H), 4.65 (s, 2H), 3.80 (s, 3H), 3.23 (q, J=10.4 Hz, 2H).

Step 6: Synthesis of 3,3,3-trifluoro-N-(2-formyl-4-methoxyphenyl)propanamide To a solution of 3,3,3-trifluoro-N-(2-(hydroxymethyl)-4-methoxyphenyl)propanamide (6.30 g, 23.9 mmol) in anhydrous $CH_2Cl_2$ (200 mL) was added $MnO_2$ (20.0 g, 229 mmol). The mixture was refluxed for 16 hours. The mixture was filtered off and the filtrate was concentrated to give the desired product (5.30 g, yield 84%).

Step 7: Synthesis of 6-methoxy-3-(trifluoromethyl)quinolin-2(1H)-one

To a solution of 3,3,3-trifluoro-N-(2-formyl-4-methoxyphenyl)propanamide (5.30 g, 20.3 mmol) in DMF (100 mL) was added $K_2CO_3$ (14.0 g, 101 mmol). The mixture was heated to 60° C. for 1.5 hours. The mixture was diluted with EtOAc (200 mL) and filtered off. The filtrate was washed with $H_2O$ (100 mL) and brine (100 mL), dried over $Na_2SO_4$, and concentrated in vacuo to give the desired product (4.60 g, yield 94%). $^1$H NMR (CDCl3 300 MHz): δ 12.25 (brs, 1H), 8.18 (s, 1H), 7.40 (d, J=9.0 Hz, 1H), 7.25 (dd, J=9.0, 2.7 Hz, 1H), 7.02 (d, J=2.7 Hz, 1H), 3.87 (s, 3H).

Step 8: Synthesis of 2-chloro-6-methoxy-3-(trifluoromethyl)quinoline

A solution of 6-methoxy-3-(trifluoromethyl)quinolin-2 (1H)-one (4.60 g, 18.9 mmol) in $POCl_3$ (30 mL) was refluxed for 2.5 hours. The solvent was removed under reduced pressure and the residue was neutralized by 2M NaOH to pH 7. An EtOAc workup was followed by removal of volatiles under reduced pressure. The residue was purified by column chromatography on silica gel (PE/EtOAc=15/1) to give the desired product (4.60 g, yield 94%).

Step 9: Synthesis of 2-chloro-3-(trifluoromethyl)quinolin-6-ol

To a solution of above product (1.00 g, 3.83 mmol) in anhydrous $CH_2Cl_2$ (20 mL) was added $BBr_3$ (3.0 mL, 31.8 mmol) at 0° C. The mixture was stirred at 0° C. for 2 hours. The mixture was quenched with ice-water (10 mL) and extracted with $CH_2Cl_2$ (30 mL×3). The combined organic layer was washed with brine (50 mL), dried over $Na_2SO_4$ and concentrated under reduced pressure to give Intermediate 6 (600 mg, yield 63%) as a solid. $^1$H NMR ($CDCl_3$ 400 MHz): δ 8.37 (s, 1H), 8.00 (d, J=9.2 Hz, 1H), 7.48 (dd, J=8.8, 2.4 Hz, 1H), 7.22 (d, J=2.8 Hz, 1H).

Intermediate 7: Synthesis of 2-chloro-4-fluoro-6-methoxyquinoline

Step 1: Synthesis of 2,4-dichloro-6-methoxyquinoline

A mixture of p-anisidine (100 g, 0.813 mol), and malonic acid (85.0 g, 0.817 mol) in $POCl_3$ (500 mL) was refluxed for 6 hours. The excess POCl₃ was removed in vacuo and the residue was neutralized with 8 M NaOH to pH 7. The aqueous layer was extracted with CH₂Cl₂ (300 mL×3), washed with brine (500 mL), dried over Na₂SO₄ and concentrated in vacuo. Purification by column chromatography on silica gel (PE/EtOAc=15/1) gave the desired product (35.0 g, yield: 19%).

Step 2: Synthesis of
2-chloro-6-methoxyquinolin-4-amine

A suspension of 2,4-dichloro-6-methoxyquinoline (5.00 g, 22.0 mmol) in NH₃ (g)/MeOH (saturated, 40 mL) was heated to 150° C. for 16 hours in a sealed tube. The solvent was removed and the residue was diluted with MeOH (20 mL). The mixture was filtered off and the filtrate was concentrated to give the crude product. Purification by column chromatography on silica gel (PE/EtOAc=2/1) gave product (7.50 g, yield: 55%) as a solid.

Step 3: Synthesis of
2-chloro-4-fluoro-6-methoxyquinoline

A solution of 2-chloro-6-methoxyquinolin-4-amine (4.50 g, 21.6 mmol) in HF-pyridine (45 mL) was cooled to −10-0° C. Then NaNO₂ (1.80 g, 26.1 mmol) was added portionwise and the mixture was stirred at 0° C. for 1 hour and at 30° C. for 1 hour. Then the mixture was heated to 65° C. for 1.5 hours. The mixture was quenched with ice-water (100 mL); the aqueous layer was neutralized with 2 M NaOH to pH 7. The mixture was filtered off and the filtrate was extracted with EtOAc (50 mL×3), the organic layer was washed with brine (100 mL), dried over Na₂SO₄ and concentrated in vacuo. Purification by column chromatography on silica gel (PE/EtOAc=15/1) gave Intermediate 7 (3.60 g, yield: 40%). $^1$H NMR (CDCl3 400 MHz): δ 7.92 (dd, J=9.2, 1.6 Hz, 1H), 7.40 (dd, J=9.2, 2.8 Hz, 1H), 7.25 (s, 1H), 7.10 (d, J=9.2 Hz, 1H), 3.97 (s, 3H).

Intermediate 8: Synthesis of
2-chloro-6-methoxyquinolin-4-amine

Step 1: Synthesis of
2,4-dichloro-6-methoxyquinoline

A mixture of p-anisidine (100 g, 0.813 mol), and malonic acid (85.0 g, 0.817 mol) in POCl₃ (500 mL) was refluxed for 6 hours. The excess POCl₃ was removed in vacuo and the residue was neutralized with 8 M NaOH to pH 7. The aqueous layer was extracted with CH₂Cl₂ (300 mL×3), the combined organic layer was washed with brine (500 mL), dried over Na₂SO₄ and concentrated in vacuo to give the crude product, which was purified by column chromatography on silica gel (PE/EtOAc=15/1) to give 2,4-dichloro-6-methoxyquinoline (35.0 g, yield: 19%) as a white solid.

Step 2: Synthesis of Intermediate 8

A suspension of 2,4-dichloro-6-methoxyquinoline (5.00 g, 22.0 mmol) in NH₃ (g)/MeOH (saturated, 40 mL) was heated to 150° C. for 16 hours in a sealed tube. The solvent was removed and the residue was diluted with MeOH (20 mL). The mixture was filtered off and the filtrate was concentrated to give the crude product, which was purified by column chromatography on silica gel (PE/EtOAc=2/1) to give 2-chloro-6-methoxyquinolin-4-amine (7.50 g, yield: 55%) as a yellow solid.

Intermediate 9: Synthesis of
2-chloro-8-fluoroquinolin-6-yl acetate

Step 1: Synthesis of
3-chloro-N-(2-fluoro-4-hydroxyphenyl)propanamide

4-Amino-3-fluorophenol (3.4 g) was mixed with 3-chloropropanoyl chloride (3.56 g) in acetone (60 mL) and heated at reflux over 3 hours. After aqueous work-up with EtOAc/water, the isolated organic layers were dried over Na₂SO₄ and concentrated in vacuo. The crude product was purified with silica gel chromatography to give the product (2.95 g) as a light brown solid.

Step 2: Synthesis of
8-fluoro-6-hydroxy-3,4-dihydroquinolin-2(1H)-one

3-Chloro-N-(2-fluoro-4-hydroxyphenyl)propanamide (2.1 g) was mixed with anhydrous AlCl₃ (7 g) and heated at 160° C. overnight. The resultant mixture was treated with 1N HCl and extracted with EtOAc. After isolation of the organic layer and removal of solvents under reduced pressure, the desired crude product (1.8 g) was collected as light brown solids.

Step 3: Synthesis of
8-fluoro-2-oxo-1,2,3,4-tetrahydroquinolin-6-yl acetate

Crude 8-fluoro-6-hydroxy-3,4-dihydroquinolin-2(1H)-one (0.574 g) was treated with acetyl chloride (330 mg) and TEA (0.68 mL) in DCM (8 mL) over 3 h. After aqueous work-up with EtOAc/water, the crude product was purified with a flash column chromatography to afford the desired product (382 mg) as colorless solids.

Step 4: Synthesis of
8-fluoro-2-hydroxyquinolin-6-yl acetate

To a solution of 8-fluoro-2-oxo-1,2,3,4-tetrahydroquinolin-6-yl acetate (718 mg) in toluene (8 mL) was added DDQ (1.2 g). The resultant solution was heated at 70° C. over 48 h. After aqueous work-up with EtOAc, the crude product was purified by a flash silica column chromatography to afford the pure product (550 mg) as a colorless solid.

Step 5: Synthesis of Intermediate 9

To a solution of 8-fluoro-2-hydroxyquinolin-6-yl acetate (550 mg) in DMF (6 mL) was added POCl₃ (0.6 mL). Then, the mixture was heated at 80° C. over a couple of hours. After aqueous work-up, the desired product, 2-chloro-8-fluoroquinolin-6-yl acetate (380 mg) was obtained by flash silica column chromatography.

Intermediate 10: Synthesis of methyl 3-fluoro-4-(4,4,5,5-tetramethyl-1,3,2-dioxaborolan-2-yl)benzoate Step 1: Synthesis of methyl
4-bromo-2-fluorobenzoate To a solution of 4-bromo-2-fluorobenzoic acid (4 g, 18 mmol) in methanol (10 mL) was added dropwise oxalyl dichloride (4.6 g, 36 mmol). The reaction was heated to 60°

C. overnight and added slowly into ice water, and extracted with DCM (50 mL×2). The combined extracts were washed with brine, dried over $Na_2SO_4$ and concentrated to give the desired product (3.7 g, 88%) as brown solid.

Step 2: Synthesis of Intermediate 10

To a solution of methyl 4-bromo-2-fluorobenzoate (1 g, 4.29 mmol) in 1,4-dioxane (20 mL) were added $Pin_2B_2$ (1.31 g, 5.15 mmol), potassium acetate (1.26 g, 12.87 mmol) and $Pd(dppf)Cl_2$ (106.2 mg, 0.128 mmol). The system was evacuated and refilled with $N_2$. The reaction mixture was heated at 100° C. for 17 h. The mixture was concentrated and the residue was purified by silica gel chromatography (PE/EA=15/1) to afford Intermediate 10 (950 mg, 79%) as a yellow solid. $^1$H-NMR (CDCl$_3$, 500 MHz, TMS): δ 7.80 (t, J=1.5 Hz, 2H), 7.67 (d, J=10 Hz, 1H), 3.92 (s, 3H), 1.37 (s, 12H) ppm.

Example 58: GSNOR Assays

Various compounds were tested in vitro for their ability to inhibit GSNOR activity. GSNOR inhibitor compounds in Examples 1-56 had an $IC_{50}$ of about <10 μM. GSNOR inhibitor compounds in Examples 1-4, 6, 8, 10-14, 16-35, 37-43, 45-50, and 52-56 had an $IC_{50}$ of about <0.5 μM. GSNOR inhibitor compounds in Examples 1-4, 8, 10-14, 17-28, 30, 31, 37, 40-41, 43, 46, 48-49, and 52-56 had an $IC_{50}$ of about <0.1 μM.

GSNOR expression and purification is described in Biochemistry 2000, 39, 10720-10729.

GSNOR Fermentation:

Pre-cultures were grown from stabs of a GSNOR glycerol stock in 2XYT media containing 100 ug/ml ampicillin after an overnight incubation at 37° C. Cells were then added to fresh 2XYT (4 L) containing ampicillin and grown to an OD ($A_{600}$) of 0.6-0.9 at 37° C. before induction. GSNOR expression was induced with 0.1% arabinose in an overnight incubation at 20° C.

GSNOR Purification:

E. coli cell paste was lysed by nitrogen cavitation and the clarified lysate purified by Ni affinity chromatography on an AKTA FPLC (Amersham Pharmacia). The column was eluted in 20 mM Tris pH 8.0/250 mM NaCl with a 0-500 mM imidazole gradient. Eluted GSNOR fractions containing the Smt-GSNOR fusion were digested overnight with Ulp-1 at 4° C. to remove the affinity tag then re-run on the Ni column under the same conditions. GSNOR was recovered in the flowthrough fraction and for crystallography is further purified by Q-Sepharose and Heparin flowthrough chromatography in 20 mM Tris pH 8.0, 1 mM DTT, 10 uM $ZnSO_4$.

GSNOR Assay:

GSNO and enzyme/NADH Solutions are made up fresh each day. The solutions are filtered and allowed to warm to room temperature. GSNO solution: 100 mM NaPO4 (pH 7.4), 0.480 mM GSNO. 396 μL of GSNO Solution is added to a cuvette followed by 8 μL of test compound in DMSO (or DMSO only for full reaction control) and mixed with the pipette tip. Compounds to be tested are made up at a stock concentration of 10 mM in 100% DMSO. 2 fold serial dilutions are done in 100% DMSO. 8 μL of each dilution are added to an assay so that the final concentration of DMSO in the assay is 1%. The concentrations of compounds tested range from 100 to 0.003 μM. Enzyme/NADH solution: 100 mM $NaPO_4$ (pH 7.4), 0.600 mM NADH, 1.0 μg/mL GSNO Reductase. 396 μL of the Enzyme/NADH solution is added to the cuvette to start the reaction. The cuvette is placed in the Cary 3E UV/Visible Spectrophotometer and the change in 340 nm absorbance/min at 25° C. is recorded for 3 minutes. The assays are done in triplicate for each compound concentration. $IC_{50}$'s for each compound are calculated using the standard curve analysis in the Enzyme Kinetics Module of SigmaPlot.

Final assay conditions: 100 mM $NaPO_4$, pH 7.4, 0.240 mM GSNO, 0.300 mM NADH, 0.5 μg/mL GSNO Reductase, and 1% DMSO. Final volume: 800 μL/cuvette.

Example 59: Efficacy of GSNORi in Experimental Asthma

Experimental Asthma Model:

A mouse model of ovalbumin (OVA)-induced asthma was used to screen GSNOR inhibitors for efficacy against methacholine (MCh)-induced bronchoconstriction/airway hyperresponsiveness. This is a widely used and well characterized model that presents with an acute, allergic asthma phenotype with similarities to human asthma. Efficacy of GSNOR inhibitors was assessed using a protocol in which GSNOR inhibitors were administered after OVA sensitization and airway challenge, and prior to challenge with MCh. Bronchoconstriction in response to challenge with increasing doses of MCh was assessed using whole body plethysmography ($P_{enh}$; Buxco). The amount of eosinophil infiltrate into the bronchoaveolar lavage fluid (BALF) was also determined as a measure of lung inflammation. The effects of GSNOR inhibitors were compared to vehicles and to Combivent (inhaled; IH) as the positive control.

Materials and Method

Allergen Sensitization and Challenge Protocol

OVA (500 μg/ml) in PBS was mixed with equal volumes of 10% (w/v) aluminum potassium sulfate in distilled water and incubated for 60 min. at room temperature after adjustment to pH 6.5 using 10 N NaOH. After centrifugation at 750×g for 5 min, the OVA/alum pellet was resuspended to the original volume in distilled water. Mice received an intraperitoneal (IP) injection of 100 μg OVA (0.2 mL of 500 μg/mL in normal saline) complexed with alum on day 0. Mice were anesthetized by IP injection of a 0.2-mL mixture of ketamine and xylazine (0.44 and 6.3 mg/mL, respectively) in normal saline and were placed on a board in the supine position. Two hundred fifty micrograms (100 μl of a 2.5 mg/ml) of OVA (on day 8) and 125 μg (50 μl of 2.5 mg/ml) OVA (on days 15, 18, and 21) were placed on the back of the tongue of each animal.

Pulmonary Function Testing (Penh)

In vivo airway responsiveness to methacholine was measured 24 h after the last OVA challenge in conscious, freely moving, spontaneously breathing mice with whole body plethysmography using a Buxco chamber (Wilmington, N.C.). Mice were challenged with aerosolized saline or increasing doses of methacholine (5, 20, and 50 mg/mL) generated by an ultrasonic nebulizer for 2 min. The degree of bronchoconstriction was expressed as enhanced pause ($P_{enh}$), a calculated dimensionless value, which correlates with the measurement of airway resistance, impedance, and intrapleural pressure in the same mouse. $P_{enh}$ readings were taken and averaged for 4 min. after each nebulization challenge. $P_{enh}$ is calculated as follows: $P_{enh}=[(T_e/T_r-1)\times(PEF/PIF)]$, where $T_e$ is expiration time, $T_r$ is relaxation time, PEF is peak expiratory flow, and PIF is peak inspiratory flow×0.67 coefficient. The time for the box pressure to change from a maximum to a user-defined percentage of the maximum represents the relaxation time. The $T_r$ measurement begins at the maximum box pressure and ends at 40%.

Eosinophil Infiltrate in BALF

After measurement of airway hyper-reactivity, the mice were exsanguinated by cardiac puncture, and then BALF was collected from either both lungs or from the right lung after tying off the left lung at the mainstem bronchus. Total BALF cells were counted from a 0.05 mL aliquot, and the remaining fluid was centrifuged at 200×g for 10 min at 4° C. Cell pellets were resuspended in saline containing 10% BSA with smears made on glass slides. Eosinophils were stained for 5 min. with 0.05% aqueous eosin and 5% acetone in distilled water, rinsed with distilled water, and counter-stained with 0.07% methylene blue. Alternatively, eosinophils and other leukocytes were stained with DiffQuik.

GSNOR Inhibitors and Controls

GSNOR inhibitors were reconstituted in phosphate buffered saline (PBS), pH 7.4, or 0.5% w/v carboxy methylcellulose at concentrations ranging from 0.00005 to 3 mg/mL. GSNOR inhibitors were administered to mice (10 mL/kg) as a single dose or multiple dose either intravenously (IV) or orally via gavage. Dosing was performed from 30 min. to 72 h prior to MCh challenge. Effects of GSNOR inhibitors were compared to vehicle dosed in the same manner.

Combivent was used as the positive control in all studies. Combivent (Boehringer Ingelheim) was administered to the lung using the inhaler device supplied with the product, but adapted for administration to mice, using a pipet tip. Combivent was administered 48 h, 24 h, and 1 h prior to MCh challenge. Each puff (or dose) of Combivent provides a dose of 18 μg ipatropium bromide (IpBr) and 103 μg albuterol sulfate or approximately 0.9 mg/kg IpBr and 5 mg/kg albuterol.

Statistical Analyses

Area under the curve values for $P_{enh}$ across baseline, saline, and increasing doses of MCh challenge were calculated using GraphPad Prism 5.0 (San Diego, Calif.) and expressed as a percent of the respective (IV or orally administered) vehicle control. Statistical differences among treatment groups and the respective vehicle control group within each study were calculated using one-way ANOVA, Dunnetts or Bonferroni post-hoc tests or t-test (JMP 8.0, SAS Institute, Cary, N.C. or Microsoft Excel). A p value of <0.05 among the treatment groups and the respective vehicle control group was considered significantly different.

Results

In the OVA model of asthma, Compound 8 (Example 8) significantly ($p<0.05$) decreased eosinophil infiltration in BAL by 37% of vehicle control when given via three oral doses of 10 mg/kg at 48 h, 24 h, and 1 h prior to assessment.

In the OVA model of asthma, Compound 3 (Example 3) significantly ($p<0.05$) decreased eosinophil infiltration in BAL by 42% of vehicle control when given via three oral doses of 10 mg/kg at 48 h, 24 h, and 1 h prior to assessment.

In the OVA model of asthma, Compound 27 (Example 27) significantly ($p<0.05$) decreased eosinophil infiltration in BAL by 23% of vehicle control when given via three oral doses of 10 mg/kg at 48 h, 24 h, and 1 h prior to assessment.

In the OVA model of asthma, Compound 4 (Example 4) significantly ($p<0.05$) decreased MCh-induced AHR by 19% of vehicle control and decreased eosiinophil infiltration into BALF by 20% of vehicle control when given as a single IV dose of 10 mg/kg at 24 h prior to assessment.

Example 60: Mouse Pharmacokinetic (PK) Study

Experimental Model

The mouse was used to determine the pharmacokinetics of compounds of the invention. This species is widely used to assess the bioavailability of compounds by administering both oral (PO) and intravenous (IV) test articles. Efficacy of the compounds of the invention was compared by assessing plasma exposure in male BALB/c mice either via IV or PO administration at the times of peak activity.

Materials and Methods

IV Administration of Compounds of the Invention

Compounds of the invention were reconstituted in a phosphate buffered saline (PBS)/10% Solutol (HS 15) clear solution resulting in a concentration of 0.2 mg/mL and administered to mice (2 mg/kg) as a single IV dose. Animals were dosed via the lateral tail vein. Blood samples were collected at designated time points (0.083, 0.25, 0.5, 1, 2, 4, 8, 16, 24 hours) by cardiac puncture under isoflurane anesthesia (up to 1 mL blood per animal). The blood was collected into tubes containing Li-Heparin. The blood samples were kept on ice until centrifugation within approximately 30 minutes of collection. The plasma was transferred into labeled polypropylene tubes and frozen at −70° C. until analyzed by LC/MS/MS.

PO Administration of Compounds of the Invention

The compounds of the invention were reconstituted in 40% Propylene Glycol/40% Propylene Carbonate/20% of a 5% Sucrose clear solution resulting in a concentration of 2 mg/mL and administered to mice (10 mg/kg) as a single oral dose via gavage. Blood samples were collected at 0.25, 0.5, 1, 2, 4, 8, 12, 16, 20 and 24 hours post dose by cardiac puncture under isoflurane anesthesia. The blood was collected in tubes containing Li-Heparin. The blood samples were kept on ice until centrifugation within approximately 30 minutes of collection. The plasma was transferred into labeled polypropylene tubes and frozen at −70° C. until analyzed by LC/MS/MS.

LC/MS/MS Analysis

Plasma samples at each timepoint were analyzed using a LC-MS/MS with a lower limit of quantification (LLOQ) of 1 ng/mL. Plasma was analyzed to determine the amount of the compound of the invention in each sample and regression curves generated for each compounds of the invention in the relevant matrixes.

WinNonlin analysis was used for calculating PK parameters for both the IV and PO administrations:

PK parameters for IV portion—$AUC_{last}$; $AUC_{INF}$; T1/2; Cl; Vss; $C_{max}$; MRT PK parameters for PO portion—$AUC_{last}$; $AUC_{INF}$; T1/2; $C_{max}$; Cl, MRT.

In addition to the above PK parameters, bioavailability (% F) was calculated.

Compounds in Examples 3, 4, 8, 13, 19, 27, and 28 were tested and all had an oral bioavailability of greater than 9%. Compounds in Examples 3, 8, 13, and 27 had an oral bioavailability of greater than 45%.

Example 61: Efficacy of GSNOR Inhibitors in Experimental Inflammatory Bowel Disease (IBD)

Overview of the Models:

Acute and chronic models of dextran sodium sulfate (DSS)-induced IBD in mice were used to explore efficacy of GSNORi against this disease. Acute and chronic DSS-induced IBD are widely used and well characterized models that induce pathological changes in the colon similar to those observed in the human disease. In these models and in human disease, epithelial cells within the crypts of the colon are disrupted, leading to dysfunction of the epithelial barrier and the ensuing tissue inflammation, edema, and ulceration. GSNORi therapy may benefit IBD by restoring s-nitroso-glutathione (GSNO) levels, and thus prevent or reverse the epithelial barrier dysfunction.

Acute Prophylactic Model:

Experimental IBD was induced by administration of DSS in the drinking water of male C57Bl/6 mice (N=8 to 10 mice per group) for 6 consecutive days. GSNORi was dosed orally at doses of 0.1 to 10 mg/kg/day for 10 days starting two days prior to and continuing two days post DSS exposure. Two days post DSS exposure, the effect of GSNORi was assessed in a blinded fashion via endoscopy and histopathology using a five point scale ranging from a score=0 (normal tissue) through a score=4 (ulcerative tissue damage and marked pathological changes). Levels of circulating cytokines involved in inflammatory pathways were also assessed. The effect of GSNORi was compared to vehicle treated controls. The corticosteroid, prednisolone, was used as the positive control in this study and was administered daily at 3 mg/kg/day via oral dosing. Naïve mice (N=5) were also assessed as a normal tissue control.

Chronic Treatment Model:

Experimental IBD was induced by administration of DSS in the drinking water of male C57Bl/6 mice (N=10 to 12 mice per group) for 6 consecutive days. GSNORi was dosed orally at doses of 10 mg/kg/day for 14 days starting one day after cessation of DSS exposure. Efficacy of GSNORi was assessed in a blinded fashion via endoscopy after 7 days and 14 days of GSNORi dosing and via histopathology after 14 days of GSNORi dosing using a five point scale ranging from a score=0 (normal tissue) through a score=4 (ulcerative tissue damage and marked pathological changes). Levels of circulating cytokines involved in inflammatory pathways were also assessed. The effect of GSNORi was compared to vehicle treated controls. The corticosteroid, prednisolone, was used as the positive control in this study and was administered daily at 3 mg/kg/day via oral dosing. Naïve mice (N=5) were also assessed as a normal tissue control.

Results:

Compound 3 (Example 3) attenuated colon injury and lowered levels of cytokines involved in inflammatory responses in a mouse model of acute DSS-induced IBD. The percent of mice presenting with severe colon injury scores via endoscopy and histopathology assessments was significantly ($p<0.05$) decreased by 38% to 88% of vehicle control after oral treatment with Compound 3 at 0.1, 1, or 10 mg/kg/day for 10 consecutive days using a prophylactic dosing regimen. Compound 3 also restored circulating inflammatory cytokines towards levels observed in untreated naïve mice. These effects of Compound 3 were comparable to or greater than those observed for prednisolone.

Compound 8 (Example 8) attenuated colon injury in a mouse model of acute DSS-induced IBD. The percent of mice presenting with severe colon injury scores via endoscopy or histopathology assessments was decreased by 44% or 26%, respectively, of vehicle control after oral treatment with Compound 8 at 10 mg/kg/day for 10 consecutive days using a prophylactic dosing regimen.

Compound 19 (Example 19) attenuated colon injury in a mouse model of acute DSS-induced IBD. The percent of mice presenting with severe colon injury scores via endoscopy assessment was decreased by 31% of vehicle control after oral treatment with Compound 19 at 10 mg/kg/day for 10 consecutive days using a prophylactic dosing regimen.

Compound 13 (Example 13) attenuated colon injury in a mouse model of chronic DSS-induced IBD. The percent of mice presenting with severe colon injury scores via endoscopy or histopathology assessment was significantly ($p<0.05$) decreased by 52% or 53%, respectively, of vehicle control after oral treatment with Compound 13 at 10 mg/kg/day for up to 14 consecutive days using a treatment dosing regimen.

Example 62: Efficacy of GSNOR Inhibitors in Experimental Chronic Obstructive Pulmonary Disease (COPD)

Short Duration Cigarette Smoke COPD Models

The efficacy of GSNOR inhibitors was assessed in a mouse model of chronic obstructive pulmonary disease (COPD) induced by short duration (4 days or 11 days) of exposure to cigarette smoke. Infiltration of inflammatory cells into the bronchoalveolar lavage fluid (BALF) and BALF levels of chemokines involved in inflammation and tissue turnover/repair were measured to assess the influences of GSNOR inhibitors on some of the early events associated with the initiation and progression of COPD.

Overview of the Models:

Efficacy of GSNOR inhibitors against COPD was explored using acute (4 day) and subchronic (11 day) models of cigarette smoke-induced COPD in mice. Exposure of animals to cigarette smoke provides a model of COPD in which injury is induced by the same causative agent as in human disease and in which injury exhibits similarities to the human disease, including airway obstruction, airspace enlargement, and involvement of inflammatory responses in these pathologies. In animal models, changes in lung pathology are only evident after extended (several months) duration of exposure to cigarette smoke, thus making chronic models prohibitive as effective screening tools. More recently, models exploring inflammatory responses after short duration (2 weeks or less) of smoke exposure in mice have been utilized as tools for screening efficacy and mechanisms of action of novel therapeutics against COPD. The key roles of inflammation in the initiation and progression of COPD, make these short duration models relevant for initial tests of efficacy of novel therapeutics.

Acute (4 Day) Smoke Exposure Model:

Female C57Bl/6 mice (N=8 per group) were exposed to cigarette smoke using a whole body exposure chamber. Mice were exposed daily for 4 consecutive days to 4 cycles of smoke from 6 sequential cigarettes (Kentucky 3R4F without filter) with a 30 minute smoke free interval between cycles. GSNOR inhibitors were administered daily via oral dosing at 10 mg/kg/day for 7 days starting 2 days prior to smoke exposure and continuing 1 day post-exposure. The effects of GSNOR inhibitors were assessed by quantitating the numbers of total cells, leukocytes, and leukocytes differentials in the BALF via light microscopy and the levels of BALF chemokines via ELISA at approximately 24 h after the last smoke exposure. The effect of GSNOR inhibitors were compared to vehicle treated controls. The PDE4 inhibitor, roflumilast, was used as the positive control for the study. A group of naïve mice (N=8) was exposed to air and used as a negative control for the study.

Subchronic (11 Day) Smoke Exposure Model:

Female C57Bl/6 mice (N=10 per group) were exposed to cigarette smoke generated from Marlboro 100 cigarettes without filters. Exposure times were 25 min. on study day 1, 35 min. on study day 2, and 45 min. on study days 3 to 11. GSNOR inhibitors were administered one hour prior to smoke exposure on each day. GSNOR inhibitors were dosed orally at 1 to 10 mg/kg/day for 11 days. The effects of GSNOR inhibitors were assessed by quantitating the number of total cells, and leukocytes differentials in the BALF via light microscopy at 24 h after the last exposure. The effect of GSNOR inhibitors were compared to vehicle treated controls and expressed as percent inhibition of the cigarette smoke induced increases in BALF cell numbers. Roflumilast was used as the positive control for the study and was dosed at 5 mg/kg/day. A group of naïve mice (N=10) was exposed to air and dosed with vehicle as a negative control for the study.

Results:

Compound 3 (Example 3) attenuated the smoke-induced changes in BALF cellular infiltrate and BALF inflammatory chemokines. Compound 3 significantly ($p<0.05$) decreased total cells, leukocytes, macrophages, neutrophils, and eosinophils in BALF by 66%, 80%, 75%, 84%, and 95%, respectively, compared to vehicle treated controls when dosed orally at 10 mg/kg/day for 7 days in the acute 4 day smoke model. These effects of Compound 3 were comparable to or greater than those observed for roflumilast. Compound 3 also restored BALF chemokines towards levels observed in naïve mice. In the subchronic 11 day model, Compound 3 inhibited the smoke-induced increase in total cells ($p<0.05$), macrophages, neutrophils ($p<0.05$), eosinophils, and lymphocytes ($p<0.05$) in BALF by 25%, 24%, 41%, 70%, and 49%, respectively, when dosed orally at 10 mg/kg/day for 11 days. When dosed orally at 5 mg/kg/day, Compound 3 inhibited total cells, macrophages, neutrophils ($p<0.05$), and lymphocytes ($p<0.05$) in BALF by 22%, 23%, 29%, and 46%, respectively.

Compound 8 (Example 8) significantly ($p<0.05$) inhibited the smoke-induced increase in total cells, macrophages, neutrophils, and lymphocytes in BAL by 35% to 48%, 24% to 43%, 41% to 70%, and 49 to 65%, respectively, when dosed orally at 1 to 10 mg/kg/day for 11 days in the subchronic 11 day model. There was no dose response of effect with 1, 5, or 10 mg/kg/day. The effects of Compound 8 were comparable to those of roflumilast.

Compound 13 (Example 13) significantly ($p<0.05$) inhibited the smoke-induced increase in total cells, macrophages, neutrophils, and lymphocytes in BAL by 56%, 53%, 67%, and 60%, respectively, when dosed orally at 1 mg/kg/day for 11 days in the subchronic 11 day model. These effects of Compound 13 were comparable to those of roflumilast.

Compound 27 (Example 27) significantly ($p<0.05$) inhibited the smoke-induced increase in total cells, macrophages, neutrophils, and lymphocytes in BAL by 44%, 41%, 64%, and 46%, respectively, when dosed orally at 1 mg/kg/day for 11 days in the subchronic 11 day model. These effects of Compound 27 were comparable to those of roflumilast.

Example 63: An Exploratory Mouse Study of Acetaminophen Toxicity

S-nitrosoglutathione reductase (GSNOR) inhibition has been previously shown in our hands to ameliorate the negative manifestations of gastrointestinal injury in animal models. As an extension of these observations, the effects of S-nitrosoglutathione (GSNO) or GSNOR inhibitors (GSNORi) on acetaminophen (ACAP) induced liver toxicity can be evaluated in a mouse model of liver injury. Blood samples are collected for liver function assays and tissue samples are collected at the end of the study for histopathologic examination.

Materials and Methods

GSNORi, GSNO, acetaminophen (ACAP, Sigma) Vehicles (½ cc syringes for dosing), Isoflurane, 18 1 cc syringes w/26 g needles for blood collection, 90 serum separator tubes for clinical chemistry.

General Study Design:

Animals (5/group) are acclimated for at least 3 days prior to dosing. On Study Day 1, acetaminophen treatment (300 mg/kg PO) was given a single time=0 to fasted animals. Two hours later, GSNORi (10 mg/kg/dose) or GSNO (5 mg/kg/dose) are intravenously administered to the treatment groups. GSNORi or GSNO are given at 24 and 48 hours-post their initial administration to the treatment groups. Mice are observed for signs of clinical toxicity and blood was collected at 6, 24, and 72 hours post-ACAP administration for liver function tests: Alkaline phosphatase (ALK); Alanine aminotransferase (ALT); Aspartate aminotransferase (AST); Gamma glutamyltransferase (GGT) and Total bilirubin (TBILI). Livers are collected at 72 hours for histopathologic examination.

Study Outline

| Group | Treatment | Dose | Drug Concentration | N |
|---|---|---|---|---|
| 1 | ACAP PO | 300 mg/kg | 10 ml/kg | 5 |
| 2 | Saline PO | 0 mg/kg | 10 ml/kg | 5 |
| 3 | GSNORi IV | 10 mg/kg | 1 mg/mL | 5 |
| 4 | GSNO IV | 5 mg/kg | 1 mg/mL | 5 |
| 5 | GSNORiIV + ACAP | 10 m/k/300 m/k | 1 mg/mL | 5 |
| 6 | GSNO IV + ACAP | 5 m/k/300 m/k | 1 mg/mL | 5 |

Study Calendar:

| | |
|---|---|
| Day-6 | Receive mice and place in regular cages |
| Day-1 | Fast animals overnight |
| Day 0 | Weigh, PO ACAP time = 0, time = 2 IV GSNO or GSNORi bleed all groups at at 6 hr post-ACAP |
| Day 1 | Weigh, bleed all groups for 24 hr LFTs, IV GSNO or GSNORi |
| Day 2 | Weigh, IV GSNO or GSNORi |
| Day 3 | Bleed for 72 hr LFTs, collect livers for weight and histology |

Vehicle, GSNO and GSNORi Preparation

The vehicle control article is Phosphate Buffered Saline (PBS) (not containing calcium, potassium, or magnesium) adjusted to pH 7.4. The vehicle components are weighed into a container on a tared balance and brought to volume with purified water (w/v). The 10× stock solution is mixed using a magnetic stirrer, as necessary. Thereafter, the 10× stock solution is diluted with deionized water at a ratio of 1:9 (v/v). GSNO is warmed to room temperature before preparation of solutions. Prior to use, the PBS solution is nitrogen sparged. 1 mg/mL GSNO solutions are kept cold (i.e., kept on an ice bath) and protected from light and used within 4 hours of preparation. GSNORi Preparation, the 1 mg/mL concentration is reconstituted in phosphate buffered saline (PBS), pH 7.4. GSNORi is administered to mice (10 mL/kg) as a single (IV) daily dose. Dosing is performed 2 hours post-ACAP administration and then 26 and 50 hours later. Effects of GSNO or GSNORi are compared to ACAP and saline vehicle dosed in the same manner.

Calculations:

Mean body weights, mean liver organ weights and clinical pathology endpoints (+/−SD) with T-test and ANOVA (alpha=0.05) comparison to vehicle control group. The clinical pathology data are prepared as mean values unless the data are not normally distributed, in which case, median values can be presented with the minimum and maximum value range.

Example 64: An Exploratory Study to Assess the Anti NASH Fibrotic Activity of GSNORi in STAM Mice S-nitrosoglutathione reductase (GSNOR) inhibition has been previously shown in our hands to ameliorate the negative manifestations of gastrointestinal injury and ACAP injury in mouse models. As an extension of these observations, the effects of GSNOR inhibitors (GSNORi) ability to reverse fibrotic activity in nonalcoholic steatohepatitis (NASH)-induced liver disease is evaluated in STAM (signal transducing adaptor molecule) mice. In these mice sequential changes are seen from liver steatosis to fibrosis within two weeks and there are close similarities to human NASH histopathology.

Materials and Methods

GSNORi, Telmisartan, Vehicles (½ cc syringes for dosing), Isoflurane, 18 1 cc syringes w/26 g needles for blood collection, 90 serum separator tubes for clinical chemistry.

General Study Design:

Animals (6/group) are acclimated prior to beginning the Study. At 4 weeks of age the animals are put on a diet, group 1 (normal mice) receives a normal diet while groups 2-4 (STAM mice) are put on a high fat diet for the duration of the Study. At Study Week 7 the mice begin oral daily dosing with GSNORi and are sacrificed at Study Week 9. Mice are observed for signs of clinical toxicity and blood/tissue is collected for liver analyses: Plasma triglycerides (TG); Alanine aminotransferase (ALT); Aspartate aminotransferase (AST); Gene Expression: Timp-1, α-SMA, collagen 3, TNF-α and MCP-1 as well as histopathologic examination using HE staining for (NAFLD) activity score and Sirius-red staining (fibrosis area).

Study Outline

| Group | Treatment | Diet | Dose | Drug Concentration | N |
|---|---|---|---|---|---|
| 1 | normal | ND | 0 mg/kg | 0 ml/kg | 6 |
| 2 | STAM + vehicle | HFD | 10 mg/kg | 1 mg/mL | 6 |
| 3 | STAM + GSNORi IV | HFD | 10 mg/kg | 1 mg/mL | 6 |
| 4 | STAM + Telmisarten | HFD | 10 mg/kg | 1 mg/mL | 6 |

ND: normal diet,
HFD: high fat diet

Calculations:

Mean body weights, mean liver organ weights and clinical pathology endpoints (+/−SD) with T-test and ANOVA (alpha=0.05) comparison to vehicle control group. The clinical pathology data are prepared as mean values unless the data are not normally distributed, in which case, median values were presented with the minimum and maximum value range.

It will be apparent to those skilled in the art that various modifications and variations can be made in the methods and compositions of the present invention without departing from the spirit or scope of the invention.

What is claimed is:

1. A method of treatment of a disorder selected from the group consisting of asthma, chronic obstructive pulmonary disease (COPD), cystic fibrosis, and inflammatory diseases, which comprises administering to a patient in need thereof, a therapeutically effective amount of a compound of Formula (I)

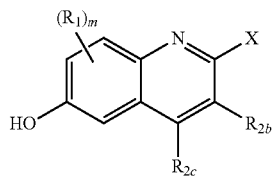

Formula I wherein
m is selected from the group consisting of 0, 1, 2, or 3;
$R_1$ is independently selected from the group consisting of chloro, fluoro, bromo, cyano, and methoxy;
$R_{2b}$ and $R_{2c}$ are independently selected from the group consisting of hydrogen, halogen, $C_1$-$C_3$ alkyl, fluorinated $C_1$-$C_3$ alkyl, cyano, $C_1$-$C_3$ alkoxy, and $N(CH_3)_2$;
X is selected from the group consisting of

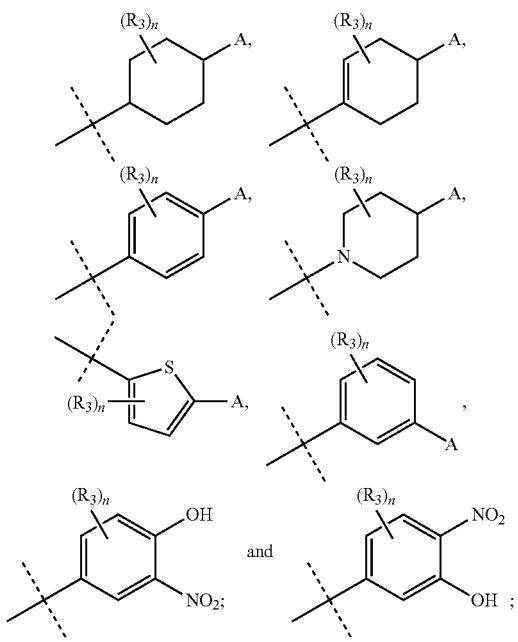

n is selected from the group consisting of 0, 1, and 2;
$R_3$ is independently selected from the group consisting of halogen, $C_1$-$C_3$ alkyl, fluorinated $C_1$-$C_3$ alkyl, cyano, $C_1$-$C_3$ alkoxy, and $NR_4R_{4'}$ where $R_4$ and $R_{4'}$ are independently selected from the group consisting of $C_1$-$C_3$ alkyl, or $R_4$ when taken together with $R_{4'}$ form a ring with 3 to 6 members; and
A is selected from the group consisting of or a pharmaceutically acceptable salt, stereoisomer, or N-oxide thereof, and
wherein the compound is administered with a secondary active agent administered for treatment of same said disorder.

2. The method of claim 1 wherein the secondary active agent is selected from the group consisting of an NO donor, other NO bioactivity generating compounds, an NO releaser, a chemotherapeutic agent, an agent that imposes nitrosative or oxidative stress, a phosphodiesterase inhibitor, a β-agonist, a steroid, an anti-muscarinics, or a leukotriene antagonist (LTD-4).

3. The method of claim 1 wherein
$R_1$ is independently selected from the group consisting of chloro, fluoro, and bromo;
X is selected from the group consisting of

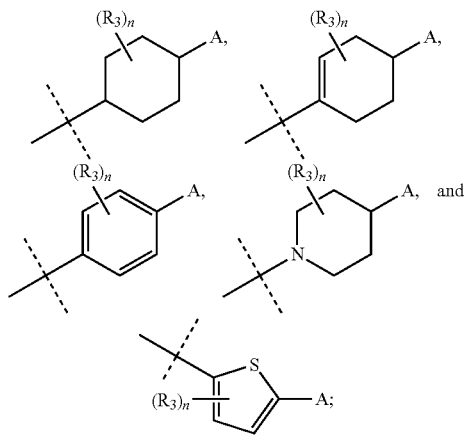

and
$R_3$ is independently selected from the group consisting of halogen, $C_1$-$C_3$ alkyl, fluorinated $C_1$-$C_3$ alkyl, cyano, $C_1$-$C_3$ alkoxy, and $NR_4R_{4'}$ where $R_4$ and $R_{4'}$ are independently selected from the group consisting of $C_1$-$C_3$ alkyl, or $R_4$ when taken together with $R_{4'}$ form a ring with 3 to 6 members.

4. The method of claim 1 wherein m is selected from the group consisting of 0 and 1; $R_{2b}$ and $R_{2c}$ are independently selected from the group consisting of hydrogen, chloro, fluoro, methyl, trifluoromethyl, cyano, methoxy, and $N(CH_3)_2$; n is selected from the group consisting of 0 and 1; and $R_3$ is independently selected from the group consisting of fluoro, chloro, bromo, methyl, trifluoromethyl, cyano, methoxy, and $N(CH_3)_2$.

5. The method of claim 4 wherein X is

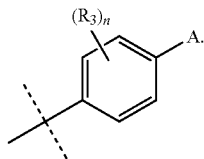

6. The method of claim 5 wherein A is COOH.
7. The method of claim 1 wherein the compound of Formula I is selected from the group consisting of
4-(6-hydroxy-3-methylquinolin-2-yl)benzoic acid;
2-(4-(1H-tetrazol-5-yl)phenyl)-3-methylquinolin-6-ol;
4-(6-hydroxyquinolin-2-yl)benzoic acid;
2-(4-(1H-tetrazol-5-yl)phenyl)quinolin-6-ol;
1-(6-hydroxyquinolin-2-yl)piperidine-4-carboxylic acid;
(1r,4r)-4-(6-hydroxyquinolin-2-yl)cyclohexanecarboxylic acid;
(1s,4s)-4-(6-hydroxyquinolin-2-yl)cyclohexanecarboxylic acid;
3-chloro-4-(6-hydroxyquinolin-2-yl)benzoic acid;
2-chloro-4-(6-hydroxyquinolin-2-yl)benzoic acid;
2-fluoro-4-(6-hydroxyquinolin-2-yl)benzoic acid;
2-(4-(2H-tetrazol-5-yl)phenyl)-4-chloroquinolin-6-ol;
3-(4-(6-hydroxyquinolin-2-yl)phenyl)-1,2,4-oxadiazol-5(2H)-one;
3-fluoro-4-(6-hydroxyquinolin-2-yl)benzoic acid;
4-(6-hydroxyquinolin-2-yl)-3-methoxybenzoic acid;
5-(6-hydroxyquinolin-2-yl)thiophene-2-carboxylic acid;
4-(6-hydroxyquinolin-2-yl)cyclohex-3-enecarboxylic acid;
4-(3-fluoro-6-hydroxyquinolin-2-yl)benzoic acid;
4-(4-chloro-3-fluoro-6-hydroxyquinolin-2-yl)benzoic acid;
4-(3-chloro-6-hydroxyquinolin-2-yl)benzoic acid;
3-(2-fluoro-4-(6-hydroxyquinolin-2-yl)phenyl)-1,2,4-oxadiazol-5(4H)-one;
3-(3-fluoro-4-(6-hydroxyquinolin-2-yl)phenyl)-1,2,4-oxadiazol-5(4H)-one;
4-(4-chloro-6-hydroxyquinolin-2-yl)benzoic acid;
2-(2-chloro-4-(2H-tetrazol-5-yl)phenyl)quinolin-6-ol;
5-(4-(6-hydroxyquinolin-2-yl)phenyl)-1,3,4-oxadiazol-2(3H)-one;
3-(dimethylamino)-4-(6-hydroxyquinolin-2-yl)benzoic acid;
4-(4-fluoro-6-hydroxyquinolin-2-yl)benzoic acid;
4-(6-hydroxyquinolin-2-yl)-3-methylbenzoic acid;
4-(3-chloro-6-hydroxyquinolin-2-yl)-3-fluorobenzoic acid;
3-(4-(6-hydroxyquinolin-2-yl)phenyl)-1,2,4-thiadiazol-5(2H)-one;
4-(6-hydroxyquinolin-2-yl)-3-(trifluoromethyl)benzoic acid;
4-(6-hydroxy-3-(trifluoromethyl)quinolin-2-yl)benzoic acid;
2-(4-carboxyphenyl)-6-hydroxyquinoline 1-oxide;
5-(4-(6-hydroxyquinolin-2-yl)phenyl)-1,3,4-thiadiazol-2(3H)-one;
5-(4-(6-hydroxyquinolin-2-yl)phenyl)-1,2,4-oxadiazol-3(2H)-one;
(1r,4r)-4-(3-chloro-6-hydroxyquinolin-2-yl)cyclohexanecarboxylic acid;
(1s,4s)-4-(3-chloro-6-hydroxyquinolin-2-yl)cyclohexanecarboxylic acid;
3-chloro-4-(4-fluoro-6-hydroxyquinolin-2-yl)benzoic acid;
2-(5-(2H-tetrazol-5-yl)thiophen-2-yl)quinolin-6-ol;
5-(4-(6-hydroxyquinolin-2-yl)phenyl)-1,2,4-thiadiazol-3(2H)-one;
3-fluoro-4-(4-fluoro-6-hydroxyquinolin-2-yl)benzoic acid;
1-(6-hydroxy-3-(trifluoromethyl)quinolin-2-yl)piperidine-4-carboxylic acid;
4-(5-chloro-6-hydroxyquinolin-2-yl)benzoic acid;
(1r,4r)-4-(6-hydroxy-3-(trifluoromethyl)quinolin-2-yl)cyclohexanecarboxylic acid;
(1s,4s)-4-(6-hydroxy-3-(trifluoromethyl)quinolin-2-yl)cyclohexanecarboxylic acid;
4-(5-bromo-6-hydroxyquinolin-2-yl)benzoic acid;
3-bromo-4-(6-hydroxyquinolin-2-yl)benzoic acid;
4-(4-(dimethylamino)-6-hydroxyquinolin-2-yl)benzoic acid;

4-(4-fluoro-6-hydroxyquinolin-2-yl)-3-methoxybenzoic acid;
3-cyano-4-(6-hydroxyquinolin-2-yl)benzoic acid;
2-(4-carboxy-2-chlorophenyl)-6-hydroxyquinoline 1-oxide;
4-(3-cyano-6-hydroxyquinolin-2-yl)benzoic acid;
4-(5-fluoro-6-hydroxyquinolin-2-yl)benzoic acid;
4-(8-fluoro-6-hydroxyquinolin-2-yl)benzoic acid; and
3-fluoro-4-(5-fluoro-6-hydroxyquinolin-2-yl)benzoic acid.

8. The method of claim 7 wherein the compound is 3-chloro-4-(6-hydroxyquinolin-2-yl)benzoic acid.

9. The method of claim 7 wherein the compound is 3-fluoro-4-(6-hydroxyquinolin-2-yl)benzoic acid.

10. The method of claim 7 wherein the compound is 4-(6-hydroxyquinolin-2-yl)-3-methylbenzoic acid.

11. The method of claim 1 wherein the disorder is selected from the group consisting of pulmonary disorders, inflammatory diseases, and functional bowel disorders.

12. The method of claim 11 wherein the pulmonary disorder is selected from the group consisting of asthma, chronic obstructive pulmonary disease (COPD), and cystic fibrosis.

13. The method of claim 12 wherein the pulmonary disorder is cystic fibrosis.

14. The method of claim 11 wherein the inflammatory disorder is inflammatory bowel disease (IBD).

* * * * *